(12) United States Patent
Sharma et al.

(10) Patent No.: US 10,221,415 B2
(45) Date of Patent: Mar. 5, 2019

(54) MICRORNAS 206 AND 21 COOPERATE TO PROMOTE RAS-EXTRACELLULAR SIGNAL-REGULATED KINASE SIGNALING BY SUPPRESSING THE TRANSLATION OF RASA1 AND SPRED1

(71) Applicant: West Virginia University, Morgantown, WV (US)

(72) Inventors: Sriganesh B. Sharma, Morgantown, WV (US); Chen-Chung Lin, Morgantown, WV (US); Mark K. Farrugia, Morgantown, WV (US); J. Michael Ruppert, Bruceton Mills, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 15/252,865

(22) Filed: Aug. 31, 2016

(65) Prior Publication Data
US 2017/0067049 A1 Mar. 9, 2017

Related U.S. Application Data

(60) Provisional application No. 62/214,631, filed on Sep. 4, 2015.

(51) Int. Cl.
| | |
|---|---|
| *A61K 31/713* | (2006.01) |
| *C12N 15/113* | (2010.01) |
| *A61K 9/00* | (2006.01) |
| *A61K 35/13* | (2015.01) |

(52) U.S. Cl.
CPC .......... *C12N 15/113* (2013.01); *A61K 9/0019* (2013.01); *A61K 31/713* (2013.01); *A61K 35/13* (2013.01); *C12N 2310/113* (2013.01); *C12N 2310/14* (2013.01); *C12N 2310/141* (2013.01); *C12N 2310/531* (2013.01); *C12N 2320/31* (2013.01)

(58) Field of Classification Search
CPC .............. A61K 31/713; A61K 2300/00; C12N 15/113; C12N 2310/113; C12N 2310/141; C12N 2320/31
See application file for complete search history.

(56) References Cited

U.S. PATENT DOCUMENTS

| | | | | |
|---|---|---|---|---|
| 2012/0122953 A1* | 5/2012 | Moorwood | ........ | C07K 14/4708 514/44 A |
| 2014/0005251 A1* | 1/2014 | Weijzen | ............... | C12N 15/113 514/44 A |

OTHER PUBLICATIONS

Parasramka et al, Clin. Epigenetics 4:16, pp. 1-10, 2012.*
Meza-Sosa et al, PLoS ONE 9(9):e103987, pp. 1-13; Sep. 2, 2014.*
Dong et al, Int. J. Oncology 41:1005-1012, 2012.*
Dong et al, Med. Oncol. 31: 57, pp. 1-10, 2014; available online Jun. 15, 2014.*
Radojicic et al, Cell Cycle 10(3): 507-517, 2011.*
Sharma, S.B. et al., MicroRNAs 206 and 21 Cooperate to Promote RAS-Extracellular Signal-Regulated Kinase Signaling by Suppressing the Translation of RASA1 and SPRED1, Molecular and Cellular Biology, 2014, 4143-4164, vol. 34, No. 22.
Johnson Gary L. et al., Mitogen-Activated Protein Kinase Pathways Mediated by ERK, JNK, and p38 Protein Kinases, Science, 2002, 1911-1912, vol. 298.
Downward, Julian, Targeting RAS Signalling Pathways in Cancer Therapy, Nature Reviews/Cancer, 2003, 11-22, vol. 3, Nature Publishing Group.
Kolch, Walter, Coordinating ERK/MAPK Signalling Through Scaffolds and Inhibitors, Nature Reviews/Molecular Cell Biology, 2005, 827-838, vol. 6.
McCubrey, James A. et a., Roles of the RAF/MEK/ERK and PI3K/PTEN/AKT Pathways in Malignant Transformation and Drug Resistance, Advan. Enzyme, Regul, 2016, 249-279, vol. 46, Elsevier Ltd.
Roberts, P.J., et al., Targeting the Raf-MEK-ERK Mitogen-activated Protein Kinase Cascade for the Treatment of Cancer, Oncogene, 2007, 3291-3310, vol. 26, Nature Publishing Group.
Mebratu, Yohannes et al., How ERK1/2 Activation Controls Cell Proliferation and Cell Death is Subcellular Localization the Answer?, Cell Cycle, 2009, 1168-1175, vol. 8, Issue 8, Landes Bioscence.
Young, Amy, et al., Ras Signaling and Therapies, Advances in Cancer Research, 2009, 1-17, Elsevier Inc.
Pylayeva-Gupta, Yuliya et al., RAS oncogenes: weaving a tumorigenic web, Nature Reviews/Cancer, 2011, 761-774, vol. 11, Macmillan Publishers Limited.
Boguskl, Mark S. et al., Proteins regulating Ras and its relatives, Nature, 1993, 643-654, vol. 366, Nature Publishing Group.
Yoshimura A., Regulation of Cytokine Signaling by the SOCS and Spred Family Proteins, J. Med, 2009, 73-83, 58(2).
Vigil, D. et al., Ras Superfamily GEFs and GAPs: Validated and Tractable Targets for Cancer Therap?, Nature Reviews/Cancer, 2010, 842-857, vol. 10, Macmillan Publishers Limited.
Stowe, I.B., A Shared Molecular Mechanism Underlies the Human Rasopathies Legius Syndrome and Neurofibromatosis-1, Genes & Development, 2012, 1421-1426, vol. 26, Cold Spring Harbor Laboratory Press.

(Continued)

*Primary Examiner* — Kevin K Hill
(74) *Attorney, Agent, or Firm* — Buchanan Ingersoll & Rooney PC; Craig G. Cochenour, Esq.

(57) ABSTRACT

The present invention provides a method for inhibiting the RAS-ERK pathway by upregulation of RASA1 and SPRED1 mRNAs in tumor cells by anti-miR treatment. The method includes wherein an anti-miR-206 binds to a nucleotide comprising the sequence UAGCUUAUCAGACU (SEQ ID NO: 21), or to a nucleotide comprising the sequence UGGAAUGUAAGGAAGUGUGUGG (SEQ ID NO: 9). A method of re-expression of RAS-ERK pathway inhibitory proteins in triple negative cancer cells by administering to a patient having cancer an effective amount of an antagonist of KLF4-dependent microRNAs.

1 Claim, 29 Drawing Sheets

Specification includes a Sequence Listing.

(56) References Cited

OTHER PUBLICATIONS

Brems, H. et al., Germline Loss-of-Function Mutations in SPRED1 Cause a Neurofibromatosis 1-like Phenotype, Nature Genetics, 2007, 1120-1126, vol. 39, No. 9, Nature Publishing Group.
Schubbert S. et al., 2007. Hyperactive Ras in developmental disorders and cancer. Nat Rev Cancer 7:295-308.
Tidyman W.E. et al., 2009, The RASopathies: developmental syndromes of Ras/MAPK pathway dysregulation. Curr Opin Genet Dev 19:230-236.
Bos J.L. 1989. RAS oncogenes in human cancer: a review. Cancer Res 49:4682-4689.
Davies H. et al., 2002. Mutations of the BRAF gene in human cancer. Nature 417:949-954.
Prior I.A. et al., 2012. A comprehensive survey of Ras mutations in cancer. Cancer Res 72:2457-2467.
Garnett M.J. et al., 2004. Guilty as charged: B-RAF is a human oncogene. Cancer Cell 6:313-319.
Santen R.J. et al., 2002. The role of mitogen-activated protein (MAP) kinase in breast cancer. J Steroid Biochem Mol Biol 80:239-256.
Whyte J. et al., 2009. Key signalling nodes in mammary gland development and cancer. Mitogen-activated protein kinase signalling in experimental models of breast cancer progression and in mammary gland development. Breast Cancer Res 11:209.
Mirzoeva O.K., et al., 2009. Basal subtype and MAPK/ERK kinase (MEK)-phosphoinositide 3-kinase feedback signaling determine susceptibility of breast cancer cells to MEK inhibition. Cancer Res 69:565-572.
Hoeflich K.P. et al., 2009. In vivo antitumor activity of MEK and phosphatidylinositol 3-kinase inhibitors in basal-like breast cancer models. Clin Cancer Res 15:4649-4664.
Prat A. et al., 2011. Deconstructing the molecular portraits of breast cancer. Mol Oncol 5:5-23.
van Beers E.H. et al., 2005. Comparative genomic hybridization profiles in human BRCA1 and BRCA2 breast tumors highlight differential sets of genomic aberrations. Cancer Res 65:822-827.
Herschkowitz J.I. et al., 2007. Identification of conserved gene expression features between murine mammary carcinoma models and human breast tumors. Genome Biol 8:R76.
Rakha E.A. et al., 2008. Basal-like breast cancer: a critical review. J Clin Oncol 26:2568-2581.
Hu X. et al., 2009. Genetic alterations and oncogenic pathways associated with breast cancer subtypes. Mol Cancer Res 7:511-522.
Cancer Genome Atlas Network. 2012. Comprehensive molecular portraits of human breast tumours. Nature 490:61-70.
Balko J.M. et al., 2012. Profiling of residual breast cancers after neoadjuvant chemotherapy identifies DUSP4 deficiency as a mechanism of drug resistance. Nat Med 18:1052-1059.
Gysin S. et al., 2011. Therapeutic strategies for targeting ras proteins. Genes Cancer 2:359-372.
Duncan J.S. et al., 2012. Dynamic reprogramming of the kinome in response to targeted MEK inhibition in triple-negative breast cancer. Cell 149:307-321.
Takahashi K. et al., 2006. Induction of pluripotent stem cells from mouse embryonic and adult fibroblast cultures by defined factors. Cell 126:663-676.
Rowland B.D. et al., 2006. KLF4, p21 and context-dependent opposing forces in cancer. Nat Rev Cancer 6:11-23.
McConnell B.B. et al., 2010. Mammalian Kruppel-like factors in health and diseases. Physiol Rev 90:1337-1381.
Ghaleb A.M., 2007 Haploinsufficiency of Kruppel-like factor 4 promotes adenomatous polyposis *coli* dependent intestinal tumorigenesis. Cancer Res 67:7147-7154.
McCormick S.M. et al., 2001. DNA microarray reveals changes in gene expression of shear stressed human umbilical vein endothelial cells. Proc Natl Acad Sci U S A 98:8955-8960.
Yoon H.S. et al., 2003. Kruppel-like factor 4 mediates p53-dependent G1/S cell cycle arrest in response to DNA damage. J Biol Chem 278:2101-2105.

Pedersen T.X. et al., 2003. Laser capture microdissection-based in vivo genomic profiling of wound keratinocytes identifies similarities and differences to squamous cell carcinoma Oncogene 22:3964-3976.
Liu Y, Sinha S, McDonald OG, Shang Y, Hoofnagle MH, and Owens GK. 2005. Kruppel-like factor 4 abrogates myocardin-induced activation of smooth muscle gene expression. J Biol Chem 280:9719-9727.
Liu Y. et al., 2006. Induction of KLF4 in response to heat stress. Cell Stress Chaperones 11:379-389.
Ghaleb A.M. et al., 2007. Kruppel-like factor 4 exhibits antiapoptotic activity following gamma-radiation-induced DNA damage. Oncogene 26:2365-2373.
Hamik A. et al., 2007. Kruppel-like factor 4 regulates endothelial inflammation. J Biol Chem 282:13769-13779.
Liao X. et al., 2010. Kruppel-like factor 4 regulates pressure-induced cardiac hypertrophy. J Mol Cell Cardiol 49:334-338.
Lai J.K. et al., 2012. Kruppel-like factor 4 is involved in cell scattering induced by hepatocyte growth factor. J Cell Sci 125:4853-4864.
Foster K.W. et al., 1999. Oncogene expression cloning by retroviral transduction of adenovirus E1A-immortalized rat kidney RK3E cells: transformation of a host with epithelial features by c-MYC and the zinc finger protein GKLF. Cell Growth Differ 10:423-434.
Foster K.W. et al., 2005. Induction of KLF4 in basal keratinocytes blocks the proliferation-differentiation switch and initiates squamous epithelial dysplasia. Oncogene 24:1491-1500.
Rowland B.D. et al., 2005. The KLF4 tumour suppressor is a transcriptional repressor of p53 that acts as a context-dependent oncogene. Nat Cell Biol 7:1074-1082.
Leng Z. et al., 2013. Kruppel-like factor 4 acts as an oncogene in colon cancer stem cell-enriched spheroid cells. PLoS One 8:e56082.
Pandya AY et al., 2004. Nuclear localization of KLF4 is associated with an aggressive phenotype in early-stage breast cancer. Clin Cancer Res 10:2709-2719.
Chu P.Y. et al., 2011. Elevated Kruppel-like factor 4 transcription factor in canine mammary carcinoma. BMC Vet Res 7:58.
Kamalakaran S. et al., 2011. DNA methylation patterns in luminal breast cancers differ from non-luminal subtypes and can identify relapse risk independent of other clinical variables. Mol Oncol 5:77-92.
Chen C.J. et al., 2012. Association of expression of Kruppel-like Factor 4 and Kruppel-like Factor 5 with the clinical manifestations of breast cancer. Pathol Oncol Res 18:161-168.
Lin C.C. et al., 2011. A KLF4-miRNA-206 autoregulatory feedback loop can promote or inhibit protein translation depending upon cell context. Mol Cell Biol 31:2513-2527.
Kasinski A.L. et al., 2011. Epigenetics and genetics. MicroRNAs en route to the clinic: progress in validating and targeting microRNAs for cancer therapy. Nat Rev Cancer 11:849-864.
Iorio M.V. et al., 2012. MicroRNA dysregulation in cancer: diagnostics, monitoring and therapeutics. A comprehensive review. EMBO Mol Med 4:143-159.
Iorio MV et al., 2005. MicroRNA gene expression deregulation in human breast cancer. Cancer Res 65:7065-7070.
Meng F. et al., 2007. MicroRNA-21 regulates expression of the PTEN tumor suppressor gene in human hepatocellular cancer. Gastroenterology 133:647-658.
Thum T. et al., 2008. MicroRNA-21 contributes to myocardial disease by stimulating MAP kinase signalling in fibroblasts. Nature 456:980-984.
Sayed D. et al., 2008. MicroRNA-21 targets Sprouty2 and promotes cellular outgrowths. Mol Biol Cell 19:3272-3282.
Asangani I.A. et al., 2008. MicroRNA-21 (miR-21) post-transcriptionally downregulates tumor suppressor Pdcd4 and stimulates invasion, intravasation and metastasis in colorectal cancer. Oncogene 27:2128-2136.
Wickramasinghe N.S. et al., 2009. Estradiol downregulates miR-21 expression and increases miR-21 target gene expression in MCF-7 breast cancer cells. Nucleic Acids Res 37:2584-2595.
Hatley M.E. et al., 2010. Modulation of K-Ras-dependent lung tumorigenesis by MicroRNA-21. Cancer Cell 18:282-293.

(56) References Cited

OTHER PUBLICATIONS

Zuker M. 2003. Mfold web server for nucleic acid folding and hybridization prediction. Nucleic Acids Res 31:3406-3415.
Mathelier A. et al., 2014. JASPAR 2014: an extensively expanded and updated open-access database of transcription factor binding profiles. Nucleic Acids Res 42:D142-D147.
Boyd K.E. et al., 1999. Coexamination of site-specific transcription factor binding and promoter activity in living cells. Mol Cell Biol 19:8393-8399.
Littlewood T.D. et al., 1995. A modified oestrogen receptor ligand-binding domain as an improved switch for the regulation of heterologous proteins. Nucleic Acids Res 23:1686-1690.
Zhang W. et al.,., 2000. The gut-enriched Kruppel-like factor (Kruppel-like factor 4) mediates the transactivating effect of p53 on the p21WAF1/Cip1 promoter. J Biol Chem 275:18391-18398.
Geiman D.E. et al., 2000. Transactivation and growth suppression by the gut-enriched Krüppel-like factor (Krüppel-like factor 4) are dependent on acidic amino acid residues and protein-protein interaction. Nucleic Acids Res 28:1106-1113.
Evans P.M. et al., 2007. Kruppel-like factor 4 is acetylated by p300 and regulates gene transcription via modulation of histone acetylation. J Biol Chem 282:33994-34002.
Yang X. et al., 2000. Transcriptional activation of estrogen receptor alpha in human breast cancer cells by histone deacetylase inhibition. Cancer Res 60:6890-6894.
Sharma D. et al., 2005. Release of methyl CpG binding proteins and histone deacetylase 1 from the Estrogen receptor alpha (ER) promoter upon reactivation in ER-negative human breast cancer cells. Mol Endocrinol 19:1740-1751.
Lewis B.P. et al., 2005. Conserved seed pairing, often flanked by adenosines, indicates that thousands of human genes are microRNA targets. Cell 120:15-20.
Fukazawa H. et al., 2002. Mitogen-activated protein/extracellular signal-regulated kinase kinase (MEK) inhibitors restore anoikis sensitivity in human breast cancer cell lines with a constitutively activated extracellular-regulated kinase (ERK) pathway. Mol Cancer Ther 1:303-309.
Turner N. et al., 2010. Integrative molecular profiling of triple negative breast cancers identifies amplicon drivers and potential therapeutic targets. Oncogene 29:2013-2023.
Infante J.R. et al., 2013. A phase 1b study of trametinib, an oral Mitogen-activated protein kinase kinase (MEK) inhibitor, in combination with gemcitabine in advanced solid tumours. Eur J Cancer 49:2077-2085.
Britten C.D. 2013. PI3K and MEK inhibitor combinations: examining the evidence in selected tumor types. Cancer Chemother Pharmacol 71:1395-1409.
Kondo N. et al., 2008. miR-206 Expression is down-regulated in estrogen receptor □-positive human breast cancer. Cancer Res 68:5004-5008.

Williams A.H. et al., 2009. MicroRNA-206 delays ALS progression and promotes regeneration of neuromuscular synapses in mice. Science 326:1549-1554.
Dey B.K et al., 2011. miR-206 and -486 induce myoblast differentiation by downregulating Pax7. Mol Cell Biol 31:203-214.
Liu N. et al., 2012. microRNA-206 promotes skeletal muscle regeneration and delays progression of Duchenne muscular dystrophy in mice. J Clin Invest 122:2054-2065.
Guttilla I.K. et al., 2009. Coordinate regulation of FOXO1 by miR-27a, miR-96, and miR-182 in breast cancer cells. J Biol Chem 284:23204-23216.
Fujita S. et al., 2008. miR-21 Gene expression triggered by AP-1 is sustained through a double-negative feedback mechanism. J Mol Biol 378:492-504.
Armstrong J.A. et al., 1998. A SWI/SNF-related chromatin remodeling complex, E-RC1, is required for tissue-specific transcriptional regulation by EKLF in vitro. Cell 95:93-104.
Kadam S. et al., 2003. Transcriptional specificity of human SWI/SNF BRG1 and BRM chromatin remodeling complexes. Mol Cell 11:377-389.
Wu J.I. et al., 2009. Understanding the words of chromatin regulation. Cell 136:200-206.
Gaspar-Maia A. et al., 2011. Open chromatin in pluripotency and reprogramming. Nat Rev Mol Cell Biol 12:36-47.
Clark G.J. et al., 1993. Differential antagonism of Ras biological activity by catalytic and Src homology domains of Ras GTPase activation protein. Proc Natl Acad Sci U S A 90:4887-4891.
Huang D.C. et al., 1993. Plasma membrane-targeted ras GTPase-activating protein is a potent suppressor of p21ras function. Mol Cell Biol 13:2420-2431.
Wakioka T. et al., 2001. Spred is a Sprouty-related suppressor of Ras signalling. Nature 412:647-651.
Fotiadou P.P. et al., 2007. Wild-type NRas and KRas perform distinct functions during transformation. Mol Cell Biol 27:6742-6755.
Young A. et al., 2013. Oncogenic and wild-type Ras play divergent roles in the regulation of mitogen-activated protein kinase signaling. Cancer Discov 3:112-123.
Grabocka E. et at., 2014. Wild-type H- and N-ras promote mutant K-ras-driven tumorigenesis by modulating the DNA damage response. Cancer Cell 25:243-256.
Vlachos IS et al., 2012. DIANA miRPath v.2.0: investigating the combinatorial effect of microRNAs in pathways. Nucleic Acids Res 40:W498-W504.
Lu TP et al., 2012. miRSystem: an integrated system for characterizing enriched functions and pathways of microRNA targets. PLoS One 7:e42390.
Lee Y.S. et al., 2009. MicroRNAs in cancer. Annu Rev Pathol 4:199-227.
Jeng H.H. et al., 2012. Sos-mediated cross-activation of wild-type Ras by oncogenic Ras is essential for tumorigenesis. Nat Commun 3:1168.

* cited by examiner

D

MICRORNAS 206 AND 21 COOPERATE TO PROMOTE RAS-EXTRACELLULAR SIGNAL-REGULATED KINASE SIGNALING BY SUPPRESSING THE TRANSLATION OF RASA1 AND SPRED1

CROSS-REFERENCE TO RELATED APPLICATION

This utility patent application claims the benefit of priority to U.S. Provisional Patent Application Ser. No. 62/214,361, filed on Sep. 4, 2015. The entire contents of U.S. Provisional Patent Application Ser. No. 62/214,361 is incorporated by reference into this utility patent application as if fully rewritten herein.

STATEMENT REGARDING FEDERALLY SPONSORED RESEARCH OR DEVELOPMENT

This invention was made with government support under Grant No. RO1 CA127405 awarded by the National Cancer Institute, under equipment Grant No. RR020866 awarded by the National Institute of Health, under Grant Nos. P30GM103488 (CoBRE) and P20GM103434 (INBRE) awarded by the Institutional Development Award (IDeA) from the National Institute of General Medical Sciences, and under Grant Nos. P20 RR016440, P30 RR032138/GM103488 and S10 RR026378 awarded by the National Institute of Health. The government has certain rights in this invention.

SEQUENCE LISTING

Following the Abstract Of The Disclosure is set forth a paper copy of the SEQUENCE LISTING in written form (.PDF format) having SEQ ID NO:1 through SEQ ID NO: 49. The paper copy of the SEQUENCE LISTING is incorporated by reference into this application. A SEQUENCE LISTING in computer-readable form (.txt file) also accompanies this application with A Statement Of Identity Of Computer Readable Form and Written Sequence Listing.

BACKGROUND OF THE INVENTION

1. Field of the Invention

In triple-negative breast cancer (TNBC) there is recurrent genetic alteration of pathway components. Using shRNA methods, we observed that the zinc finger transcription factor Kruppel-like factor 4 (KLF4) can promote RAS-ERK signaling in TNBC cells. Endogenous KLF4 bound to the promoter regions and promoted the expression of two microRNAs (miRs), miR-206 and miR-21 (miR-206/21). Anti-sense-mediated knockdown (anti-miR) revealed that miR-206/21 coordinately promote RAS-ERK signaling and the corresponding cell phenotypes by inhibiting translation of the pathway suppressors RASA1 and SPRED1. The present invention identifies RASA1 and SPRED1 mRNAs as latent RAS-ERK pathway suppressors that can be upregulated in tumor cells by anti-miR treatment. Consequently, KLF4-regulated miRs are important for the maintenance of RAS-ERK pathway activity in TNBC cells. The present invention provides a method of treating a patient having cancer comprising providing an upregulation of RASA1 and SPRED1 by anti-microRNA (anti-miR) treatment. The pronounced inhibitory effect of anti-miR-206/21 on the level of activated ERK 1/2 identifies the enhanced translation of RASA1 and SPRED1 as an attractive therapeutic modality.

Further, this invention provides suppression of KLF4 or the anti-sense mediated silencing of miR-206 and/or miR-21 to be used in combination with MEK inhibitors or other pathway antagonists to attenuate drug resistance in cancer patients.

2. Background of the Invention

In comparison to simpler organisms, the evolution of metazoans required adaptations for the proper regulation of cell fate (1). One such adaptation is the mitogen-activated protein kinase (MAPK) pathway composed of RAS, RAF, MEK, and ERK, which regulates a variety of cell physiologic processes (2-9). Diverse stimuli including growth factors, interaction with extracellular components, and cell stress can signal through receptor tyrosine kinases (RTKs), integrins, or ion channels to regulate signaling through the RAS GTPases. GTP-bound RAS (RAS-GTP) can activate MAP3Ks (i.e., the RAF family of protein kinases), leading to sequential phosphorylation and activation of MAP2Ks (i.e., MEK 1/2) and the extracellular signal-regulated kinases (ERK 1/2).

Inhibitory proteins play important roles in RAS-ERK pathway regulation. These include the RAS p21 protein activator (GTPase activating protein [GAP]) 1 (RASA1), the GAP neurofibromin 1 (NF1), the sprouty homologs SPRY1 and SPRY2, and the sprouty-related, EVH1 domain containing (SPRED) proteins, SPRED1 and SPRED2 (10-12). SPRED1 associates with NF1 to mediate its membrane localization, implicating GAP activity as a shared molecular mechanism among pathway inhibitory proteins (13). Congenital disorders that deregulate this kinase cascade include Neurofibromatosis type I, Legius syndrome, Noonan syndrome, Costello syndrome, and cardiofaciocutaneous syndrome (8,9,14-16).

In addition, somatic alteration of this pathway is critical for the initiation and progression of a variety of cancers. Activating point mutation of RAS genes or BRAF occur in approximately 15-30% and 7% of all human cancers, respectively (3,17-20). In human breast cancer, point mutation of these genes is rare, but activated ERK 1/2 levels are frequently elevated and contribute to the aggressive behavior of cancer cells (21,22).

RAS-ERK pathway activity appears particularly critical in triple-negative breast cancers (TNBCs), tumors that are deficient in estrogen receptor (ER) a, HER2, and progesterone receptor (23,24). This group of clinically aggressive tumors overlaps extensively with the basal-like and claudin-low molecular subtypes (25). Genomic analysis of human basal-like breast tumors indicates frequent copy number gain of KRAS (32%) and BRAF (30%), and reduced gene copy number for pathway inhibitors such as RASA1 and DUSP4 (26-31). For RASA1, the correlation of mRNA levels, genomic copy number and clinical outcome supports a functional role in TNBC (29). Consistent with these results, basal-like breast tumors have a high RAS-ERK pathway activity signature (24,30). Despite this insight, therapeutic targeting of the pathway is hindered by cellular mechanisms of escape, including dynamic reprogramming of the kinome and PI 3-kinase activation, and improved strategies for inhibiting the pathway are needed (32,33).

The zinc-finger transcription factor Kruppel-like factor 4 (KLF4) is a pluripotency factor that functions in tumors in a context-dependent fashion, capable of exerting both pro-tumorigenic and anti-tumorigenic effects (34-36). Supporting a tumor suppressor role, its expression is reduced during development of tumors such as colorectal cancer, and endogenous Klf4 suppresses tumorigenesis in the Apc$^{Min}$ mouse model (37). In normal cells, KLF4 is often induced in response to cell stress or wounding, and protumorigenic influences may reflect its role in the stress response (38-46). Loss- or gain-of-function studies show that KLF4 can promote malignant properties, including epithelial transformation in vitro, escape from RAS-induced senescence, enhanced cell survival following γ-radiation-induced DNA damage, increased tumorigenicity of colorectal cancer stem cell-enriched spheroid cells, and skin tumor initiation in transgenic mice (43,47-50).

In human breast cancers, there is typically higher expression of KLF4 in tumor cells compared with the adjacent, uninvolved epithelium. This elevated protein level, or else demethylation of the KLF4 promoter, portends a poor prognosis (51-54). We previously identified microRNA (miR)-206 as a potential downstream effector of KLF4 that, in turn, directly regulates KLF4 translation, constituting a feedback loop (55). miRs associate with the RNA-induced silencing complex (RISC) to regulate the translation of cognate mRNAs. miR deregulation occurs in multiple cancer types and can promote or inhibit tumorigenesis (56-58).

SUMMARY OF THE INVENTION

The present invention provides a method of treating a patient having cancer comprising transfecting cancerous cells in vitro with either anti-miR-206, or anti-miR-21, or both said anti-miR-206 and said anti-miR-21, and injecting a therapeutically effective amount of the transfected cells into a tumor of the patient, and achieving an upregulation of RASA1 and SPRED1 for treating the cancer of the patient. Preferably, this method includes wherein the cancer is a triple negative breast cancer. In another embodiment of this method, as described herein, the injection is an orthotopic injection. Another embodiment of this method of this invention, as described herein, further includes administering a therapeutically effective amount of one or more of a MEK inhibitor or one or more of an antagonist of a RAS-ERK pathway.

Another embodiment of this invention provides a method of treating a patient having cancer comprising crippling the expression of micro RNA-206 and micro RNA-21.

Another embodiment of this invention provides a method of treating a patient having breast cancer by administering to the patient a therapeutically effective amount of an anti-microRNA 206 and a therapeutically effective amount of an anti-microRNA 21.

Another embodiment of this invention includes a compound comprising an antagonist of KLF4 dependent microRNAs.

Another embodiment of this invention includes a compound comprising transcripts of RASA1 and SPRED1.

Another embodiment of this invention includes a compound comprising anti-microRNA 206 knockdown and anti-microRNA 21 knockdown.

Another embodiment of this invention provides the method, as described herein, wherein the anti-miR-206 is capable of binding to (binds to) a nucleotide comprising the sequence

UAGCUUAUCAGACU.       (SEQ ID NO: 21)

Another embodiment of this invention provides the method, as described herein, wherein the anti-miR-206 is capable of binding to (binds to) a nucleotide comprising the sequence

UGGAAUGUAAGGAAGUGUGUGG.       (SEQ ID NO: 9)

BRIEF DESCRIPTION OF THE DRAWINGS

FIG. 1A shows that TNBC cells were transduced with lentiviral vectors expressing KLF4 shRNA or a non-targeting control (Ctl). Endogenous miR-206 levels in stably selected cells were measured by stem-loop reverse transcriptase real time quantitative PCR. miR-206 levels were measured relative to U6 snRNA (columns, mean; bars, SE; *, P<0.05; , P<0.01; *, P<0.001).

FIG. 1B is a schematic of the MIR206 locus (left panel) indicating KLF4 consensus binding sites that were analyzed by ChIP analysis of MDA-MB-231 cells (right panel).

FIG. 1C shows KLF4 protein levels (upper panels), and the KLF4-MIR206 ChIP Intensity levels (lower panels) were analyzed in MDA-MB-231 cells expressing shKLF4, a KLF4 transgene, or controls. β-actin served as a loading control for immunoblot analysis.

FIG. 2A shows the indicated proteins, including phospho-ERK 1/2 (pERK 1/2) and ERK2, were analyzed by immunoblot analysis of TNBC cells expressing shKLF4 or shCtl. Column data indicates the average of three independent experiments (bars, SD).

FIG. 2B shows the levels of GTP-bound (active) HRAS, NRAS, and KRAS in cell extracts were analyzed by affinity precipitation using the RAS binding domain of Raf-1 (RBD). RAS proteins were analyzed by immunoblot. Levels of each RAS isoform in the whole cell lysate (WCL) served as the loading control.

FIG. 2C shows that KLF4-deficient MDA-MB-231 cells were transduced with retroviral vector expressing hemagglutinin (HA) epitope-tagged KLF4 or empty vector (Ctl). miR-206 levels (left panel) and levels of the indicated proteins (right panel) were analyzed.

FIG. 2D shows KLF4-deficient MDA-MB-231 cells were transduced with a 4-hydroxytamoxifen (4-OHT) dependent transgene, KLF4-ER, or else empty vector. KLF4 and KLF4-ER levels were analyzed by immunoblot.

FIG. 2E shows miR-206 levels (left panel) and levels of the indicated proteins (right panel) were analyzed. CDKN1A is regulated by KLF4 and $p21^{Cip1/Waf1}$ therefore served as an indicator of KLF4 activity.

FIG. 3A shows that RASA1 and SPRED1 levels were determined by immunoblot analysis of KLF4-deficient cells and control cells.

FIG. 3B shows TNBC cells were transfected with either anti-miR-206 or a non-targeting anti-miR (Ctl) and miR-206 levels were determined.

FIG. 3C shows that TNBC cells were transfected with the indicated anti-miR or miR-mimic. RASA1 and SPRED1 levels were analyzed by immunoblot.

FIG. 4A and FIG. 4B show schematics of the RASA1 3' UTR (FIG. 4A) and the SPRED1 3' UTR (FIG. 4B) indicating potential miR-206 binding sites. The portion of each 3' UTR that was cloned into the translational reporter is indicated relative to the stop codon and poly-adenylation signal. The sequence of the miR-206 candidate binding site is indicated below each schematic for several mammals (underline, seed sequence complement).

FIG. 4A includes the sequences UAGCACACUUUUC-CACAUUCCA (SEQ ID NO:1) (*Homo sapiens* origin); UAGCACACUUUUCCACAUUCCA (SEQ ID NO: 2) (Pan troglodytes); UAGCACACUUUCCCACAUUCCA (SEQ ID NO: 3) (*Mus musculus*); and UAGCACAC-CUUUCCACAUUCCA (SEQ ID NO: 4) (*Bos taurus*).

FIG. 4B includes the sequences AUAUCUACUGUCA-CAUUCCA (SEQ ID NO: 5) (*Homo sapiens*); AUAUC-UACUGUCACAUUCCA (SEQ ID NO: 6) (Pan troglodytes); AUAUCUGCCACCACAUUCCA (SEQ ID NO: 7) (*Mus musculus*); and AUAUCUACUGUCACAUUCCA (SEQ ID NO: 8) (*Bos taurus*).

FIG. 4C and FIG. 4D show analyses of protein translation, WT and mutant versions of the RASA1 3' UTR (FIG. 4C) or SPRED1 3' UTR (FIG. 4D) were inserted into the 3' UTR of firefly luc (upper panels, 3' UTR WT and 3' UTR Mut). MDA-MB-231 cells were co-transfected with reporters in combination with either anti-miR (middle panel) or miR-mimic (lower panel). The normalized activity of the reporters relative to empty luc vector was analyzed at 24 hours post-transfection.

FIG. 4C includes UAGCACACUUUUCCACAUUCCA (SEQ ID NO: 1); UGGAAUGUAAGGAAGUGUGUGG (SEQ ID NO: 9); and UAGCACACUUUUCCAACUCUCA (SEQ ID NO: 10);

FIG. 4D includes the sequences AUAUAUCUACUGU-CACAUUCCA (SEQ ID NO: 49); UGGAAU-GUAAGGAAGUGUGUGG (SEQ ID NO: 9); and AUAUAUCUACUGUCAACUCUCA (SEQ ID NO: 11).

FIG. 5A show that miR-21 levels were analyzed in KLF4-deficient or control TNBC cells.

FIG. 5B shows a schematic of the MIR21 locus (left panel) indicating a KLF4 consensus binding site that was analyzed in MDA-MB-231 cells by ChIP (right panel).

FIG. 5C shows, similarly as shown in FIG. 1C, the KLF4-MIR21 ChIP Intensity levels were analyzed in MDA-MB-231 cells expressing shKLF4, a KLF4 transgene, or controls.

FIG. 5D shows that TNBC cells were transduced with empty vector or with vector encoding KLF4 or KLF4-ER. Where indicated, cells were treated with 4-OHT, and the levels of the indicated miRs were analyzed.

FIG. 5E shows, similarly as shown in FIG. 2C-2E, miR-21 levels were analyzed in KLF4-deficient TNBC cells following rescue with exogenous KLF4 (left panel) or KLF4-ER (right panel).

FIG. 5F shows that TNBC cells were transduced with the indicated shRNA vector. Proteins were analyzed by immunoblot (left panels) and miR levels were determined (right panels).

FIG. 5G shows that TNBC cells were treated with 5-aza-2'-deoxycytidine (AZA; 96 hours) or trichostatin A (TSA; 12 hours). ESR1 mRNA levels were analyzed as a positive control for drug activity (right panel).

FIG. 6A shows that MDA-MB-231 cells were transfected with the indicated anti-miR or miR-mimic, and RASA1 and SPRED1 levels were determined by immunoblot. PDCD4 is encoded by a miR-21 targeted transcript and was analyzed in parallel.

FIG. 6B shows construction of a WT translational reporter, wherein a portion of the RASA1 3' UTR (B) containing an established miR-21 binding site was inserted into the 3' UTR of firefly luc (64). The sequence of the miR-21 binding site is indicated for several vertebrates (underline, seed sequence complement).

FIG. 6B includes the sequences AUGCCAGCAACCUU-GUAAGCUA (SEQ ID NO: 12) (*Homo sapiens*); AUGC-CAGCAACCUUGUAAGCUA (SEQ ID NO: 13) (Pan troglodytes); CUGCCAGCACCUUUGUAAGCUA (SEQ ID NO: 14) (*Mus musculus*); and GUACCAGCAGC-UUUUUAAGCUA (SEQ ID NO: 15) (*Gallus gallus*).

FIG. 6C shows a schematic of the SPRED1 3' UTR indicating potential miR-21 binding sites.

FIG. 6C includes the sequences UUUUUUUAAGUCU-CUAAGCUA (SEQ ID NO: 16) (*Homo sapiens*); AUUUUUUAAGUCUCUAAGCUA (SEQ ID NO: 17) (Pan troglodytes); UAACAUGUUGCAGCUAAGCUA (SEQ ID NO: 18) (*Homo sapiens*); and UAACAU-GUUGCAGCUAAGCUA (SEQ ID NO: 19) (Pan troglodytes).

FIG. 6D and FIG. 6E show analyses of protein translation, WT or mutant versions of the indicated 3' UTR were inserted into the 3' UTR of firefly luc (upper panels). MDA-MB-231 cells were co-transfected with reporters in combination with either anti-miR or miR-mimic. The normalized activity of the reporters relative to empty luc vector was analyzed at 24 hours post-transfection.

FIG. 6D includes the sequences AACCUUGUAAGCUA (SEQ ID NO: 20) and UAGCUUAUCAGACU (SEQ ID NO: 21).

FIG. 6E includes the sequences UUUUUUUAAGUCU-CUAAGCUA (SEQ ID NO: 16); ACAUGUUGCAGC-UAAGCUA (SEQ ID NO: 22); UAGCUUAUCA-GACUGAUGUU (SEQ. ID NO: 23); UAGCUUAUCAGACUGAUGU (SEQ ID NO: 24); AAGUCUCUAGAUCA (SEQ ID NO: 25); and ACAU-GUUGCAGCUACCCUA (SEQ ID NO: 26).

FIG. 7A shows that cells were transduced with the indicated shRNA vector. Stably selected cells were analyzed for the indicated proteins by immunoblot.

FIG. 7B shows that miR levels were analyzed in the indicated cells. For MDA-MB-468 cells, the miR-206 cycle threshold exceeded 40 and the expression level was therefore designated as not detected (n.d.).

FIG. 8A shows MDA-MB-231cells and FIG. 8B shows HCCC1143 cells (TNBC cells) that were transfected with the indicated anti-miR and proteins levels were analyzed by immunoblot (pMEK 1/2: phospho-MEK 1/2; tMEK 1/2: total MEK 1/2). Transfections were performed using 12.5 nM of the indicated anti-miR, with 25 nM as the final concentration of all species combined, using anti-miR-Ctl where indicated (−).

FIG. 9A shows that TNBC cells were transfected with the indicated anti-miR and plated 24 hours post transfection (i.e., Day 0). Cell proliferation was measured using an ATP based luminescence assay (N=3; bars, SE).

FIG. 9B shows the migration of anti-miR transfected TNBC cells was measured in a Boyden chamber transwell assay (N=3; bars, SE).

FIG. 9C shows that anti-miR transfected cells were analyzed in an anoikis assay. After 24 hours in suspension, cell death was analyzed by trypan blue staining (N=3; bars, SE). In parallel, cells were treated with MEK inhibitor U0126.

FIG. 9D shows the results of three experiments that were performed independently of those in (9C), and anoikis was assessed by Annexin V-PI staining. The percent of Annexin V+ cells, representing both early and late apoptotic cells, is depicted in the right panel for each treatment group (N=3; bars, SD).

FIG. 10A shows that TNBC cells were stably transduced with shRNA vector targeting RASA1 (R1 or R2) or with a nontargeting Ctl. The indicated proteins were analyzed by immunoblot.

FIG. 10B shows that TNBC cells were stably transduced with shRNA vector targeting SPRED1 (S1 or S2) or with a nontargeting Ctl. The indicated proteins were analyzed by immunoblot.

FIG. 10C shows that RAS-GTP levels were analyzed by the RBD pulldown assay in RASA1 and SPRED1 knockdown cells and control cells.

FIG. 10D shows that SUM159PT TNBC cells were stably transduced with the indicated shRNA expression vector and the indicated proteins and RAS-GTP levels were analyzed.

FIG. 11A shows that TNBC cells expressing the indicated shRNAs were treated with anti-miR-206 and anti-miR-21 in combination (anti-miR-206/21), or with anti-miR-Ctl. Whole cell extracts were prepared and the indicated proteins were analyzed by immunoblot. Two distinct cell culture models were analyzed (MDA-MB-231 vs. HCC1143) using independent shRNAs (R1, S1, R2 and S2). For pERK 1/2 both short (S) and long (L) exposures are indicated.

FIG. 11B show that, absent any anti-miR transfection (Untransfected), baseline cell proliferation was analyzed for cells expressing the indicated shRNA and for the untransduced, parental cells (P). Following anti-miR transfection, cell proliferation was measured for control TNBC cells (shCtl) or cells deficient in RASA1 (shR1, shR2) or SPRED1 (shS1, shS2). Assays were performed following transfection of anti-miR-Ctl (AC) or anti-miR-206/21 (A+).

FIG. 11C shows MDA-MB-231 cells expressing the indicated shRNAs were transfected with either anti-miR-206/21 or anti-miR-Ctl. $2 \times 10^6$ cells were orthotopically injected into the left fourth mammary gland of athymic mice. Biweekly tumor measurements were made by using calipers. For each treatment group, the number of mice in which tumor initiation occurred by day 28 is indicated (Initiated/Total).

FIG. 12A shows KLF4-depleted TNBC cells were transfected with the indicated miR-mimic, and protein levels were analyzed by immunoblot.

FIG. 12B shows that anoikis assays were performed following transfection of the indicated miR-mimic into KLF4-depleted TNBC cells. For MDA-MB-231, cells transduced with KLF4 vector or empty vector were analyzed in parallel.

FIG. 13 is a schematic that shows the organization of the RAS-ERK pathway. miR-206/21 co-targeted repressors of RAS-ERK signaling are shown in the elongated shaded ovals. The GAP protein NF1 is indicated as a likely catalytic partner of SPRED1 (13).

DETAILED DESCRIPTION OF THE INVENTION

Figure 1A:
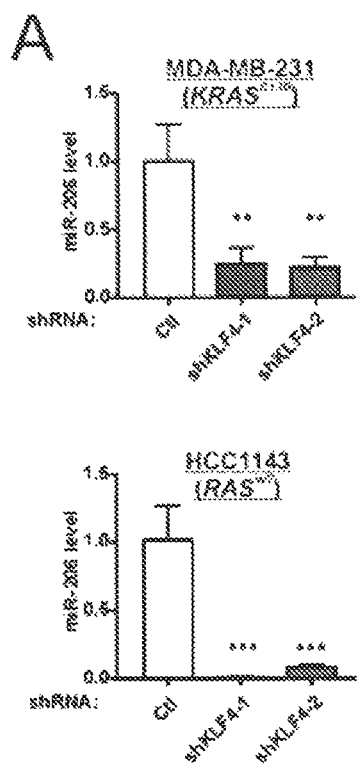
FIGS. 1A, 1B, and 1C show: KLF4 is bound to the MIR206 promoter region and induces miR-206 expression.

As used herein, the term "patient" includes any member of the animal kingdom, including but not limited to *homo sapiens*.

As used herein, the term "an effective amount" or "a therapeutically effective amount" refers to that amount of a substance that is needed to bring about a desired result, such as for example that amount of a substance that is needed to treat a patient having a disease.

The natural progression of breast cancer, HER2-enriched specifically, can be difficult to determine. Furthermore, drug resistance is nearly inevitable for the current selected therapies towards this disease. Gaining a better understanding of the intrinsic nature of a patient's tumor will help direct future treatments and inform, likely clinical outcome. Scientifically, characterizing what makes an aggressive tumor more lethal will also provide insight to tumor biology and potential drug targets. Molecular markers are attractive solutions to these problems, as they provide critical information towards the nature of the cancer, ultimately providing the physician and the patients with a more tailored approach to their disease.

The expression, of KLF4 and KLF5 in HER2-enriched breast cancer substantially stratifies the risk for distant metastasis. Patients with tumors that have lower than median expression of both KLF4 and KLF5 exhibit prolonged distant metastasis free survival (DMFS). In fact, in this cohort no deaths were seen after ~5 years. This would suggest that patients with this expression profile may be essentially cured if they survived past the fives post diagnosis. Likewise, patients with tumors that exhibit higher than median expression of both KLF4 and KLF5 have dramatically reduced DMFS and poor clinical outcome.

Using KLF4 and KLF5 as predictive markers may aid in the treatment of individuals with HER2-enriched breast cancer. If a patient were to have elevated levels of both these genes, then a physician may opt for a more aggressive treatment course due to the increased likelihood of developing distant metastasis. On the other hand, if patients were to have tumors with less KLF4 and KLF5, doctors may opt for a more conservative treatment regime thus sparing the patient money and the potential burdens of medical intervention. Furthermore, if a patient lived 5 years past their initial diagnosis with this molecular profile, this assay would provide the information to them that they may be cured.

We have also characterized the relationship between KLF4 and microRNAs (miRs)-206 and -21, downstream effectors of KLF4's functions. MicroRNAs are short, non-coding RNAs which regulate gene expression by impacting RNA translation or stability. Inhibition of these microRNAs perturbs many of the pro-tumorigenic functions KLF4 exerts, thus improving a patients length of survival.

We have evidence that KLF4 can promote drug resistance, likely through its prosurvival signals mediated by miRs. The miRs target two pathways by which HER2 and related receptor tyrosine kinases (RTKs) promote tumorigenesis in breast cancer, for example, HER2-PI3K-AKT and EGFR-RAS-RAF-MEK-ERK.

Current technology focuses on traditional molecular markers such as HER2 amplification and ER status. While these genes certainly are useful for prognosis, many times two tumors which contain the same HER2 and ER profile can progress quite differently. Therefore, for clinical decision making (e.g., radiotherapy, aggressive chemotherapy) there is a need for additional markers to further describe these tumors, as well as their likely clinical progression. KLF4 and KLF5 have been shown to stratify' a patient's DMFS interval, with lower than median expression of both genes correlating with prolonged DMFS and positive patient outcome. Likewise, tumors with higher than median expression of KLF4 and KLF5 are associated with reduced DMFS and an aggressive clinical course. The expression of these two factors has several clinical applications: Oncotype Dx, a current test available clinically, only is applicable for HER2 negative, ER positive, node-negative patients. Another available molecular test, Mammoprint only has limited utility in the HER2-enriched group and is not clinically justified. KLF4 and KLF5 levels in HER2-enriched tumors provide prognostic information to the length of DMFS independent of ER status, thus informing the physician and patient on the likely progression of their disease where a current test could not. Furthermore, the expression of KLF4 and KLF5 may enhance the prognostic capabilities for the Mammoprint test, making said analysis clinically applicable. If a physician has better understanding of the likely progression of the disease, he/she would be better able to optimize a patient's treatment regimen (i.e a more aggressive treatment course for tumors likely to reoccur distally). If a patient has a better understanding of the likely progression of their disease, it will better able them to mentally prepare for the future. Furthermore, if a patient's tumor expresses low levels of KJLF4 and KLF5 and they survive 5 years post diagnosis, current data suggests that their risk for distal reoccurrence is negligible, providing rational to curtail excessive scans and check ups as well as peace of mind. This last factor, peace of mind, would factor greatly into future clinical application and commercial usefulness. It is possible therapeutic inhibition of KLF4 and KLF5 in tumors which highly express the two genes results in dramatically prolonged DMFS. This may be accomplished by inhibiting downstream targets of the KLFs (eg. microRNA-206, microRNA-21) thus abrogating many of KLF4's protumorigenic functions. The present invention provides the use of miR-206 antagonists to sensitize tumor cells to HER2 inhibitors such as Flerceptin or lapatinib, both of which are clinically approved already, but for which initial response rates appears similar to 30% and development of resistance is nearly inevitable.

If the expression of KLF4 and KLF5 can improve prognostic capabilities in prospective studies, the clinical application can almost be immediate. Therefore, the observation of KLF4, KLF5 and DMFS may be linked to initial response to these treatments, as well as the interval of time required for the development of resistance. Furthermore, it is possible that the downstream effectors of KLF4 (miR-206 and miR-21) contribute to acquired resistance given their importance in Ras-Erk signaling, one of the main pathways HER2 signaling goes through. Therefore, therapeutic inhibition of these miRs may disrupt Ras-Erk signaling and reduce the development of resistance.

In the short term, patients will want to know if they have the "safe" form of HER2+ cancers and clinicians would use the prognostic risk in deciding if more aggressive therapy is warranted.

Despite the low prevalence of activating point mutation of RAS or RAF genes, the RAS-ERK pathway is implicated in breast cancer pathogenesis. Indeed, in triple-negative breast cancer (TNBC) there is recurrent genetic alteration of pathway components. Using shRNA methods, we observed that the zinc finger transcription factor Kruppel-like factor 4 (KLF4) can promote RAS-ERK signaling in TNBC cells. Endogenous KLF4 bound to the promoter regions and promoted the expression of two microRNAs (miRs), miR-206 and miR-21 (miR-206/21). Antisense-mediated knockdown (anti-miR) revealed that miR-206/21 coordinately promote RAS-ERK signaling and the corresponding cell phenotypes by inhibiting translation of the pathway suppressors RASA1 and SPRED1. In TNBC cells, including cells with mutation of RAS, the suppression of either RASA1 or SPRED1 increased the levels of GTP-bound, wild-type RAS and activated ERK 1/2. Unlike the control cells, treatment of RASA1- or SPRED1-suppressed cells with anti-miR-206/21 had little or no impact on the level of activated ERK 1/2 or on cell proliferation, and failed to suppress tumor initiation. These results identify RASA1 and SPRED1 mRNAs as latent RAS-ERK pathway suppressors that can be upregulated in tumor cells by anti-miR treatment. Consequently, KLF4-regulated miRs are important for the maintenance of RAS-ERK pathway activity in TNBC cells.

In this invention, we suppressed KLF4 in TNBC cells and observed a decrease in miR-206 levels, attributed to the reduced association of KLF4 with a MIR206 promoter-proximal consensus site. Pathway analysis of putative miR-206 regulated genes identified this miR as a likely regulator of MAPK signaling, and in KLF4-deficient cells we observed marked downregulation of activated ERK 1/2 regardless of the RAS mutational status. As miRs can function in a combinatorial fashion, we sought additional miR effectors of KLF4 signaling to RAS-ERK. The protumorigenic miR-21 is upregulated in breast cancer and was previously validated to target RAS-ERK pathway inhibitory proteins (59-65). Furthermore, pathway enrichment identified MAPK signaling as likely to be co-targeted by miR-206 and miR-21 (miR-206/21). We subsequently observed reduced levels of miR-21 in KLF4-deficient cells, attributed to a direct interaction of KLF4 with the MIR21 promoter. These results identified a pathway by which a pluripotency factor can signal through two distinct miRs to impact RAS-ERK signaling.

The loss of activated ERK 1/2 upon KLF4 depletion corresponded to a decrease in the level of GTP-bound wild-type (WT) RAS, and we found that miR-206 and miR-21 co-target both RASA1 and SPRED1 to repress their translation. Although each miR alone had only modest effects on the level of activated ERK 1/2, simultaneous inhibition of both miRs led to marked downregulation of activated ERK 1/2, similarly as observed for KLF4-deficient cells. In RAS-WT and RAS-mutant cells alike, depletion of either RASA1 or SPRED1 promoted RAS-ERK pathway activity by modulating the levels of WT RAS-GTP. Knockdown of either RASA1 or SPRED1 conferred resistance to antisense miR (anti-miR) mediated inhibition of RAS-ERK signaling and promoted in vivo tumor initiation. These studies identify miR-206/21 as protumorigenic outputs of KLF4 signaling in TNBC cells, identify RASA1 and SPRED1 transcripts as latent RAS-ERK suppressors, and point to antagonists of KLF4-dependent miRs as potential agents for the therapeutic re-expression of RAS-ERK pathway inhibitory proteins.

The present invention provides a method of treating a patient having cancer comprising transfecting cancerous cells in vitro with either anti-miR-206, or anti-miR-21, or both said anti-miR-206 and said anti-miR-21, and injecting a therapeutically effective amount of the transfected cells into a tumor of the patient, and achieving an upregulation of RASA1 and SPRED1 for treating the cancer of the patient. Preferably, this method includes wherein the cancer is a triple negative breast cancer. In another embodiment of this method, as described herein, the injection is an orthotopic injection. Another embodiment of this method of this invention, as described herein, further includes administering a therapeutically effective amount of one or more of a MEK inhibitor or one or more of an antagonist of a RAS-ERK pathway. Another embodiment of this invention provides a method of treating a patient having cancer comprising crippling the expression of micro RNA-206 and micro RNA-21.

Another embodiment of this invention provides a method of treating a patient having breast cancer by administering to the patient a therapeutically effective amount of an anti-microRNA 206 and a therapeutically effective amount of an anti-microRNA 21.

Another embodiment of this invention includes a compound comprising an antagonist of KLF4 dependent microRNAs.

Another embodiment of this invention includes a compound comprising transcripts of RASA1 and SPRED1.

Another embodiment of this invention includes a compound comprising anti-microRNA 206 knockdown and anti-microRNA 21 knockdown.

Another embodiment of this invention provides a method for treating a patient having breast cancer comprising providing for the therapeutic re-expression of RAS-extracellular signal-regulated kinase signaling pathway inhibitory proteins.

Another embodiment of this invention provides the method, as described herein, wherein the anti-miR-206 is capable of binding to (binds to) a nucleotide comprising the sequence

UAGCUUAUCAGACU.    (SEQ ID NO: 21)

Another embodiment of this invention provides the method, as described herein, wherein the anti-miR-206 is capable of binding to (binds to) a nucleotide comprising the sequence

UGGAAUGUAAGGAAGUGUGUGG.    (SEQ ID NO: 9)

Materials and Methods

Cell Lines, Cell Culture, and Drug Treatments.

MDA-MB-231, HCC1143, HCC1937, MDA-MB-468, and Hs578t breast cancer cell lines were obtained from ATCC. MCF10A and MCF10AT cells were provided by Steven M. Frisch (West Virginia University). SUM159PT cells were provided by Gary L. Johnson (University of North Carolina at Chapel Hill) and M6 cells were provided by Jeffrey E. Green (National Cancer Institute). MDA-MB-231 and M6 cells were cultured in DMEM supplemented with 10% (v/v) FBS. HCC1143 cells were cultured in RPMI-1640 supplemented with 10% FBS. Hs578t cells were cultured in DMEM supplemented with 5 µg/ml insulin and 10% FBS. HCC1937 and MDA-MB-468 cells were cultured in RPMI-1640 supplemented with 5 µg/ml insulin and 10% FBS. SUM159PT cells were cultured in 50:50 DMEM/F12 supplemented with 5 µg/ml insulin, 1 µg/ml hydrocortisone, and 5% horse serum. MCF10A and MCF10AT cells were cultured in 50:50 DMEM/F12 supplemented with 10 µg/ml insulin, 0.5 µg/ml hydrocortisone, 20 ng/ml EGF, 100 ng/ml cholera toxin, and 5% horse serum. Cell culture media was also supplemented with penicillin and streptomycin. 4-hydroxytamoxifen (4-OHT) was dissolved in ethanol and used at 0.3 µM. U0126 (Sigma) was dissolved in DMSO and used at 20 µM. 5-aza-2'-deoxycytidine/decitabine (AZA; Selleck Chemicals) and trichostatin A (TSA; Selleck Chemicals) were dissolved in DMSO and used at 10 µM and 400 nM respectively. Subconfluent cell cultures were treated with AZA for 96 hours or TSA for 12 hours. For the AZA treatment, the drug containing media was replenished every 24 hours.

Retroviral Transduction.

Suppression studies utilized pGIPZ lentiviral shRNAmir plasmids (V2LHS_28277—shKLF4-1, V3LHS_410934—shKLF4-2, V2LHS_28349—shKLF4-3, V3LHS_376638—shKLF4-4, V3LHS_410935—shKLF4-5, V2LHS_149857—shRASA1-1, V2LHS_203287—shRASA1-2, V2LHS_49151—shSPRED1-1, or V3LHS_634744—shSPRED1-2; Open Biosystems). The retroviral vector pLJD-HA-KLF4 was previously described (51). pLJD-KLF4-ER was generated by transfer of the insert from pBpuro-KLF4-ER to pLJD (48). Viral transduction was performed as described previously, and pGIPZ and pLJD-transduced cells were selected using puromycin (0.5 µg/ml: HCC1937, MDA-MB-468; 1 µg/ml: MCF10A, MCF10AT, MDA-MB-231, Hs578t, SUM159PT, HCC1143; 5 µg/ml: M6) or Geneticin (200 µg/ml), respectively (55).

Plasmid Construction.

pMIR-REPORT firefly luciferase (luc) vector was purchased from Ambion/Invitrogen. pRL-TK *Renilla* luc reporter was obtained from Promega (Madison, Wis.). cDNA clones containing full length RASA1 (clone ID BC033015) and a 1.2 kb fragment of the 3' untranslated region (3' UTR) of SPRED1 (clone ID BG167687) were purchased from Open Biosystems. To construct a WT RASA1 translational reporter, a 926 by fragment of the RASA1 3' UTR region was generated by sequential treatment with BamHI, Klenow fragment, and XbaI. This fragment was inserted into pMIR-REPORT vector that was prepared by sequential treatment with HindIII, Klenow fragment, and SpeI. To construct a WT SPRED1 reporter containing the putative miR-206 binding site, the 1.2 kb SPRED1 3' UTR from clone BG167687 was excised by treatment with MluI and inserted into the same site of pMIR-REPORT. Finally, a 744 by fragment of the SPRED1 3' UTR containing two putative miR-21 binding sites was amplified by PCR from MDA-MB-231 cDNA using the oligonucleotides 5'-cccacgcgtTGAAAAACTGTTTAACT-CATGT-3' (SEQ ID NO: 27) and 5'-cccacgcgtT-GAAAAACCTGTAAATAAGCAC-3' (SEQ ID NO: 28) (SPRED1 sequence indicated in uppercase). Following MluI digestion, the product was cloned into the same site of pMIR-REPORT vector.

To generate RASA1 and SPRED1 reporters with mutation of miR seed complementary regions, the WT reporter sequence was altered so as to conserve the predicted secondary structure of the WT 3' UTR, as indicated by the mfold Web Server (66). Oligonucleotides (forward, reverse; mutated bases in lowercase) for PCR mutagenesis included RASA1—miR-206 site: 5'-AAAAATAGCACACTTTTC-CAacTctCAGTGATGTGTGAGCTATGC-3' (SEQ ID NO: 29), 5'-GCATAGCTCACACATCACTGagAgtTG-GAAAAGTGTGCTATTTTT-3' (SEQ ID NO: 30); SPRED1—miR-206 site: 5'-ATATATATATCTACTGT-CAacTctCATATATTTTGAATATTTAAC-3' (SEQ ID NO: 31); 5'-GTTAAATATTCAAAATATATGagAgtTGACAG-TAGATATATATAT-3' (SEQ ID NO: 32); SPRED1—miR-21 Site 1: 5'-GTATTCAGATTTTTTTTAAGTCTCTAgat-cAATAATGTTATATTTATTG-3' (SEQ ID NO: 33), 5'-CAATAAATATAACATTATTgatcTAGAGACT-TAAAAAAAAATCTGAATAC-3' (SEQ ID NO: 34); and SPRED1—miR-21 Site 2: 5'-TTGGTAACATGTTGCAGC-TAccCTAATGACCTTAAGTGGCAATTG-3' (SEQ ID NO: 35), 5'-CAATTGCCACTTAAGGTCATTAGggTAGCTG-CAACATGTTACCAA-3' (SEQ ID NO: 36). Cloned PCR products were confirmed by sequence analysis.

Transient Transfection and Translational Reporter Assays.

Anti-miR inhibitors (AM) and miR-mimics (PM) were obtained from Ambion/Invitrogen including, hsa-miR-206 (AM10409, PM10409), hsa-miR-21-5p (AM17000, PM17100), AM Negative Control #1 (AM17010), and PM Negative Control #1 (AM17110). Inhibitors and mimics were diluted to 20 µM in nuclease free water and where indicated, transfected either singly or in combination into cells at a final total concentration of 25 nM. Where two miR reagents were cotransfected, the final concentration was 12.5 nM each. For analysis of endogenous protein or miR levels, two sequential transfections were performed. Cells were subjected to reverse transfection and, 24 hours later, forward transfection was performed as described (55). At 24 hours after the start of the forward transfection, cell extracts were prepared for expression studies, or cells were used for phenotypic studies. Translational reporter assays were performed after only a single transfection, and extracts were prepared at 24 hours after the start of the reverse transfection. Inhibitors or mimics were cotransfected with reporter plasmids, including the pRL-TK control, and Dual-Luciferase® Reporter Assays (DLR Assay, Promega) were performed as described (55).

In Vitro Cell Proliferation, Transwell Migration, and Anoikis Assays.

Cells were plated for the respective assay at 24 hours following the final transfection with AM or PM. To measure cell proliferation, $1 \times 10^3$ cells/well were transferred to 96-well plates and cultured for the indicated interval. Cell proliferation was determined using the ATPlite Luminescence ATP Detection Assay System (PerkinElmer). Cell number was calculated by constructing a standard curve and correlating cell number with the luminescence signal. In parallel, 2D cell viability was measured by trypan blue exclusion.

For transwell migration assays, $1 \times 10^4$ cells were plated in the top chamber using growth medium containing 0.5% FBS (24 well plates, pore size, 8 µm; BD Biosciences). Growth medium containing 10% FBS was used as chemoattractant in the lower chamber. After 24 hours, cells on the lower surface of the membrane were stained using the Diff-Quik™ Stain Set (Siemens) and counted.

To quantitate cell death (anoikis), $1 \times 10^5$ cells/well in DMEM complete growth medium containing 1% (w/v) methylcellulose were added to a 6-well Ultra-Low Attachment Cluster Dish (Costar). After 24 hours in suspension, the cells were washed twice with PBS and suspended in 200 µL of AccuMax (Innovative Cell Tech). Cell death was measured by trypan blue exclusion. Alternatively, suspended cells were analyzed for cell death by flow cytometry.

Flow Cytometry.

Flow cytometric analysis of apoptosis was performed using Alexa Flour® 488 Annexin V/Dead Cell Apoptosis Kit (Invitrogen). Samples were analyzed on a BD Fortessa flow cytometer using BD FACSDiva 7.0 software (BD Biosciences). 10,000 events were collected per sample. Data analysis was performed using FCS Express 4 Research Edition software (De Novo Software).

Immunoblot Analysis and Antibodies.

Cells were maintained as subconfluent monolayers in complete growth medium. For analysis of protein levels, including the levels of phosphorylated MEK 1/2 and ERK 1/2, cells were fed with complete growth medium 18-24 hours prior to extraction. Cells were washed twice in PBS and then lysed in ice-cold RIPA buffer (150 mM NaCl, 1% [w/v] sodium deoxycholate, 1% [v/v] Triton X-100, 5 mM EDTA, 50 mM Tris-HCl, pH 7.5, 0.25 mM PMSF, 1 mM benzamidine, 1 mM pepstatin, 1 µg/mL leupeptin, 1 µg/mL aprotinin, 0.4 mM sodium orthovanadate, 40 mM β-glycerophosphate, and 20 mM NaF). Extracts were centrifuged at 15,000×g and protein concentration was determined using the Bradford Assay (Bio-Rad). Following electrophoresis, proteins were transferred onto nitrocellulose membranes and probed with the indicated antibody. Antibodies included phospho-ERK 1/2 (pERK 1/2; Thr202/Tyr204; Cell Signaling, 9101), ERK2 (Santa Cruz, C-14), phospho-MEK 1/2 (pMEK 1/2; Cell Signaling, 9154), total MEK 1/2 (tMEK 1/2; Cell Signaling, 9126), anti-hemagglutinin (HA) (Roche, 3F10), KLF4 (Santa Cruz, H-180), β-actin (Santa Cruz, C-4), p21$^{Cip1/Waf1}$ (Santa Cruz, C-19), RASA1 (Santa Cruz, B4F8), SPRED1 (Abcam, 77079), PDCD4 (Rockland Immunochemicals, 600-401-965), HRAS (Santa Cruz, C-20), NRAS (Santa Cruz, F155), and KRAS (Santa Cruz, F234). Bound antibodies were detected using Pierce ECL Western Blotting Substrate (Thermo Scientific). Scanned images were quantitated using ImageJ software, with normalization to the loading control. Column data indicates the average of three independent experiments.

RAS-GTP Affinity Precipitation.

Affinity precipitation of active RAS (RAS-GTP) utilized the RAS Assay Reagent, a GST-fusion protein corresponding to the RBD (residues 1-149) of Raf-1 (Millipore). For analysis of RAS-GTP levels, cells were fed with complete growth medium 18-24 hours prior to protein extraction. Cells were washed twice in PBS and then lysed in ice-cold magnesium-containing lysis buffer (MLB; 25 mM HEPES, pH 7.5, 150 mM NaCl, 1% Igepal CA-630, 0.25% sodium deoxycholate, 10% glycerol, 10 mM MgCl$_2$, 1 mM EDTA, 25 mM NaF, 1 mM sodium orthovanadate, 10 µg/ml leupeptin, and 10 µg/ml aprotinin). Whole cell lysates (WCL) were centrifuged at 15,000×g for 15 minutes and the protein concentration was determined using the Bradford Assay (Bio-Rad). WCLs were diluted to 1 mg/ml and 1 ml of the lysate was precleared with glutathione agarose and used for affinity precipitation with 10 µg of the Raf-1 RBD agarose conjugate. The agarose beads were collected by centrifugation at 15,000×g and washed three times with MLB. Beads were resuspended in 2× Laemmli sample buffer and boiled at 95° C. for 5 minutes. Samples were diluted to 1× Laemmli buffer and subjected to SDS-PAGE and immunoblot analysis.

Reverse Transcription and Real-Time PCR Detection of miRs.

Total RNA was extracted using mirVana™ miRNA Isolation Kit (Ambion/Invitrogen). For mRNA analysis, total RNA was reverse transcribed using SuperScript II reverse transcriptase (Invitrogen). ESR1 transcripts were analyzed using the Brilliant II SYBR® Green QPCR Master Mix (Agilent) with the following primers: 5'-AGGTGGACCT-GATCATGGAG-3' (SEQ ID NO: 37), 5'-AAGCTTCGAT-GATGGGCTTA-3' (SEQ ID NO: 38). Reactions were normalized to B2M: 5'-TCTCTGCTGGATGACGTGAG-3' (SEQ ID NO: 39), 5'-TAGCTGTGCTCGCGCTACT-3' (SEQ ID NO: 40). Individual miRs were analyzed by stem-loop reverse transcription followed by quantitative real-time PCR (qPCR) detection using TaqMan MicroRNA Assays (Applied Biosystems) and normalized to U6 snRNA: hsa-miR-206 (#000510), hsa-miR-21-5p (#000397), U6 snRNA (#001973). PCR reactions were performed on a Mx3005P™ Real-Time PCR System (Stratagene). mRNA and miR levels were determined by the $\Delta\Delta C_T$ method. Three independent experiments were performed in duplicate fashion.

Chromatin Immunoprecipitation (ChIP).

Potential KLF4 binding sites were identified using JASPAR (67). Chromatin from $4\times10^7$ cells was prepared as described (68) and used as input for each immunoprecipitation (IP). Chromatin was sonicated in ice water using a Bioruptor (Diagenode) set at high energy, cycling on/off at 30 second intervals for 6 cycles of 10 minutes each. IP was performed using 1 μg of the indicated antibody. Following IP, elution, reversal of crosslinks, and proteinase K digestion, DNA was purified using Qiaquick spin columns (Qiagen) and then eluted in 50 μl of 10 mM Tris-HCl (pH 8.0). 2% of the ChIP yield was used as input for each PCR reaction. ChIP Intensity levels were determined by use of the $\Delta C_T$ method to compare the yield obtained using anti-KLF4 or normal IgG. The sequences of oligonucleotides are: miR-21 site 1, 5'-CTTAGATTGAGAAAGACCGC-3' (SEQ ID NO: 41) and 5'-ACTTATGCTTGTGTCATCCC-3' (SEQ ID NO: 42); miR-21 site 2, 5'-GCAACCTCCACTTC-CTGGGT-3' (SEQ ID NO: 43) and 5'-CCAACACAGT-GAAACCCTGT-3' (SEQ ID NO: 44); miR-206 site 1, 5'-CATCAACAACACCCCAAGCG-3' (SEQ ID NO: 45) and 5'-GGCACAGTTTTGGATCAACCC-3' (SEQ ID NO: 46); miR-206 site 2, 5'-TGCAAAGCACAGA-GAAACGTG-3' (SEQ ID NO: 47) and 5'-ACCTTCTTC-CCATTTTCCTGGAC-3' (SEQ ID NO: 48).

Animal Studies.

Female Athymic Nude mice (Crl:NU(NCr)-Foxn1$^{nu}$, Charles River) were obtained at 6-8 weeks of age. $2\times10^6$ cells in in 100 μl of DMEM were injected into the 4th mammary fat pad. Caliper measurements were performed twice a week and tumor initiation was defined as >4 mm for both $L_1$ and $L_2$ ($L_1$, long axis; $L_2$, short axis). All animal procedures were performed under an approved protocol.

Statistical Analysis.

Data were analyzed using the unpaired t-test (two-tailed), or else one-way analysis of variance (ANOVA) followed by Tukey's multiple comparison ad hoc post-test. Growth curves were analyzed using non-linear regression curve fitting. Tumor initiation was analyzed using a 2×2 contingency table with Fisher's exact test. Statistical analyses were performed in GraphPad Prism 5 (GraphPad Software). Except where noted, assays were performed three times in duplicate fashion. Cell proliferation assays were performed in three independent experiments, each containing 5 replicates. Differences were considered significant when the analysis yielded P<0.05.

Results

KLF4 Regulates miR-206 and ERK Signaling in TNBC Cells.

Figure 1B:
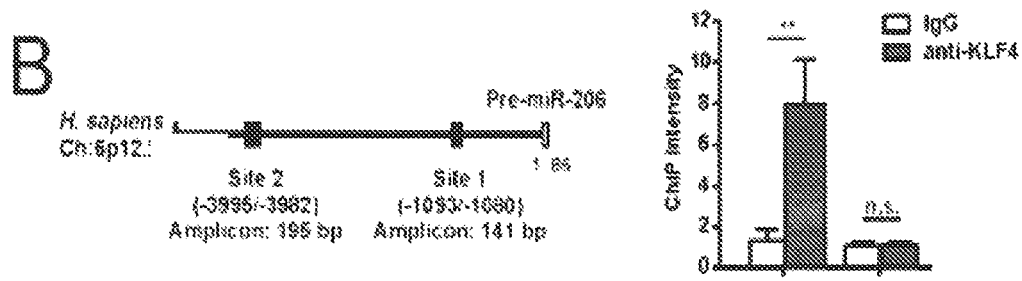
Figure 1C:
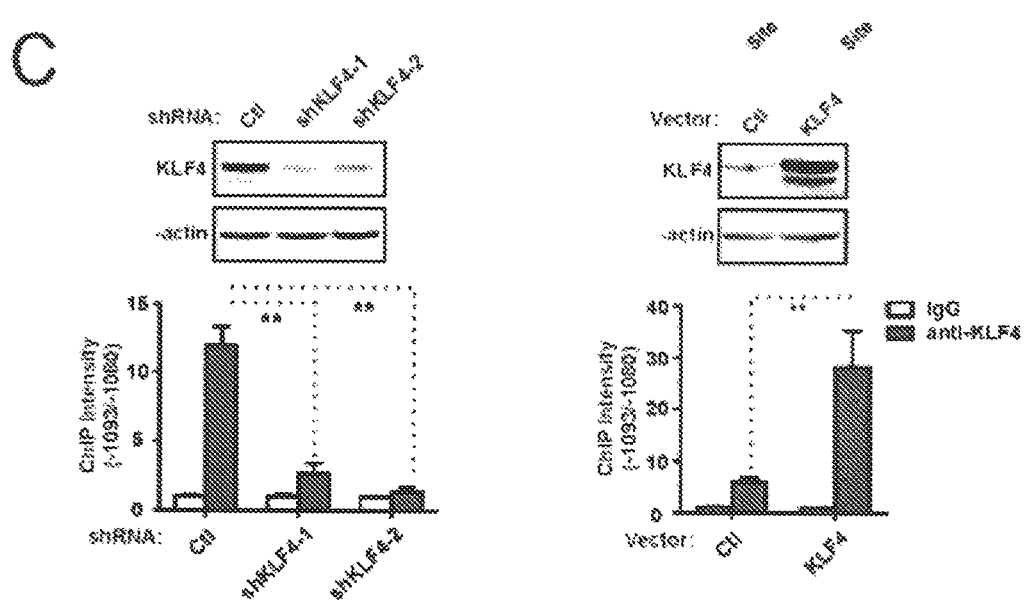

Consistent with our previous study, miR-206 levels were markedly repressed in KLF4-depleted cells (FIG. 1A) (55). Similar results were obtained in the RAS-mutant (KRAS$^{G13D}$) and claudin-low tumor line MDA-MB-231, and the RAS-WT and basal-like HCC1143 cells. ChIP analysis of KLF4 at consensus sites in the MIR206 locus identified enrichment of site 1, located within the promoter-proximal region (FIG. 1B). Supporting specificity, this enrichment was reduced in KLF4-deficient cells and increased in cells with exogenous KLF4 (FIG. 1C).

Figure 2A:
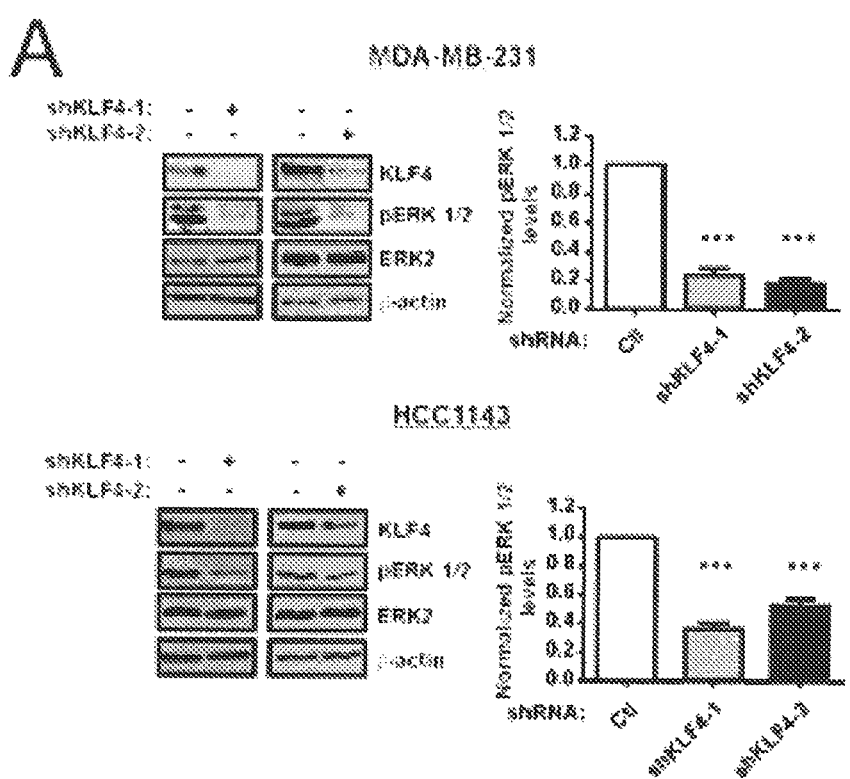
FIGS. 2A, 2B, 2C, 2D, and 2E show: KLF4 rapidly induces miR-206 and RAS-ERK signaling.
Figure 2B:
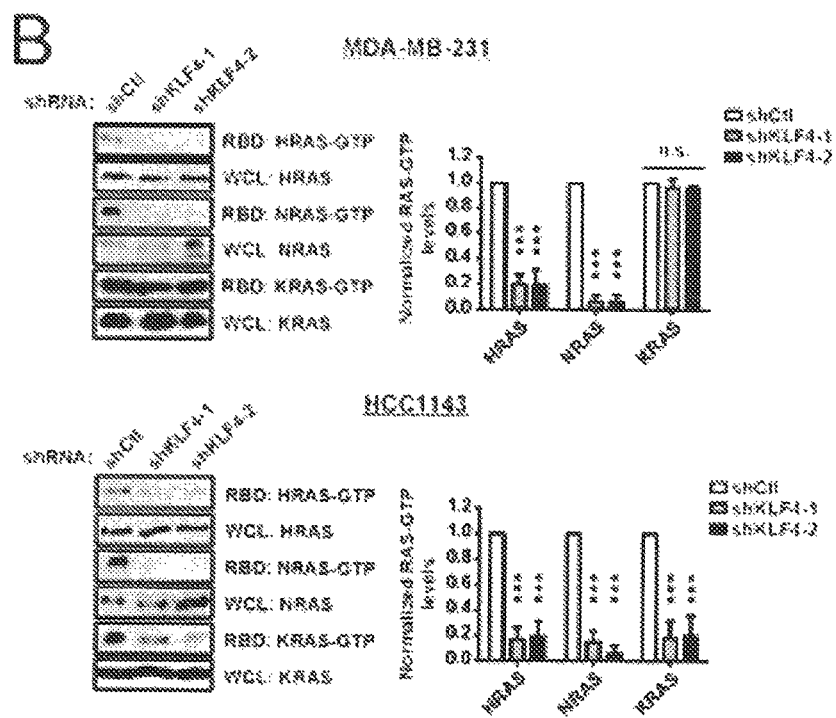
Figure 2C:
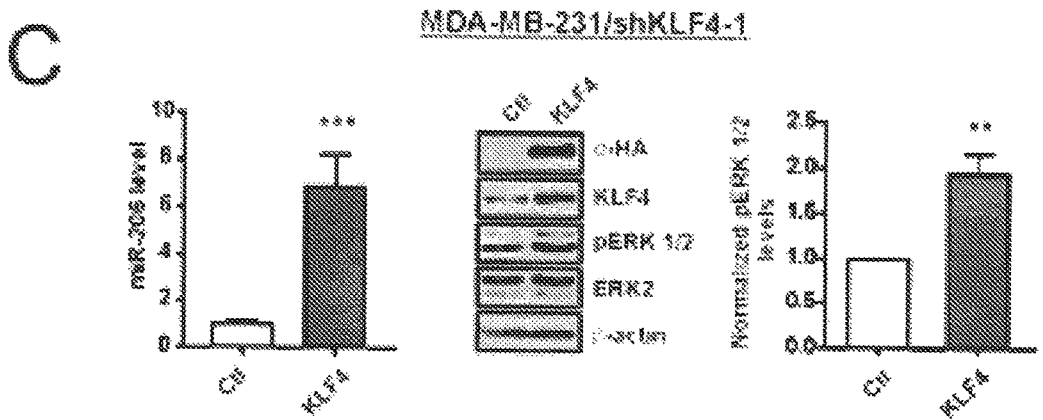

As protumorigenic mechanisms of KLF4 signaling remain poorly understood, we sought potential effectors of miR-206. In silico enrichment analysis identified MAPK signaling as likely to be regulated by miR-206, which has the potential to target 17 genes in this pathway (p=1.24× $10^{-2}$, Table 1). Because of its ability to regulate miR-206, we first determined whether endogenous KLF4 can regulate steady state RAS-ERK activity in TNBC cells by analyzing ERK 1/2 activation loop phosphorylation (i.e., activated ERK 1/2 or pERK 1/2). In KLF4-deficient cells the pERK 1/2 levels were suppressed (FIG. 2A). In these cell lines, the reduction of pERK 1/2 reflected lower levels of WT RAS-GTP, whereas mutant RAS-GTP levels were unaffected by KLF4 knockdown (FIG. 2B). In KLF4-deficient MDA-MB-231 cells, introduction of HA-tagged KLF4 rescued the levels of miR-206 and pERK 1/2 (FIG. 2C).

Figure 2D:
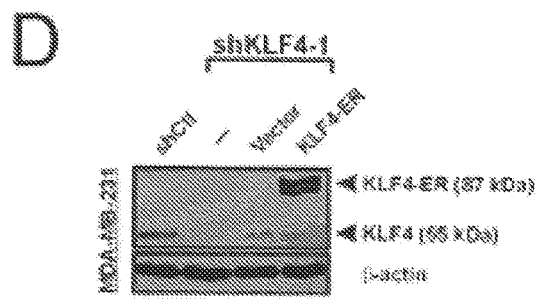
Figure 2E:
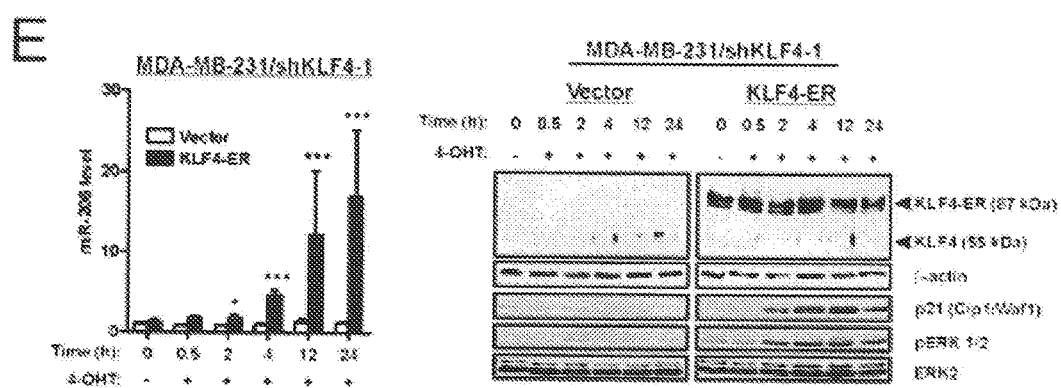

To temporally correlate the induction of miR-206 and pERK 1/2 by KLF4, we transduced KLF4-depleted MDA-MB-231 cells with KLF4-ER or empty vector (FIG. 2D). The KLF4-ER fusion protein is constitutively expressed but functionally inactive until treatment of cells with 4-hydroxytamoxifen (4-OHT) (48,69). As previously reported, addition of 4-OHT to KLF4-ER cells resulted in upregulation of miR-206 between 0.5 and 2 hours post-treatment (FIG. 2E, left panel) (55). In this experiment the induction of pERK 1/2 was apparent by 2 hours (FIG. 2E, right panel). KLF4-ER activity was supported by the induction of cyclin-dependent kinase inhibitor 1A (p21$^{Cip1/Waf1}$) in these cells (70) (FIG. 2E, right panel). The modest induction of activated ERK 1/2 by exogenous KLF4 (FIGS. 2C and 2E) was in contrast to the larger fold effect of endogenous KLF4 (FIG. 2A), identifying a discordance between the two approaches.

miR-206 Suppresses the Translation of the RAS-ERK Pathway Inhibitors RASA1 and SPRED1.

Figure 3A:
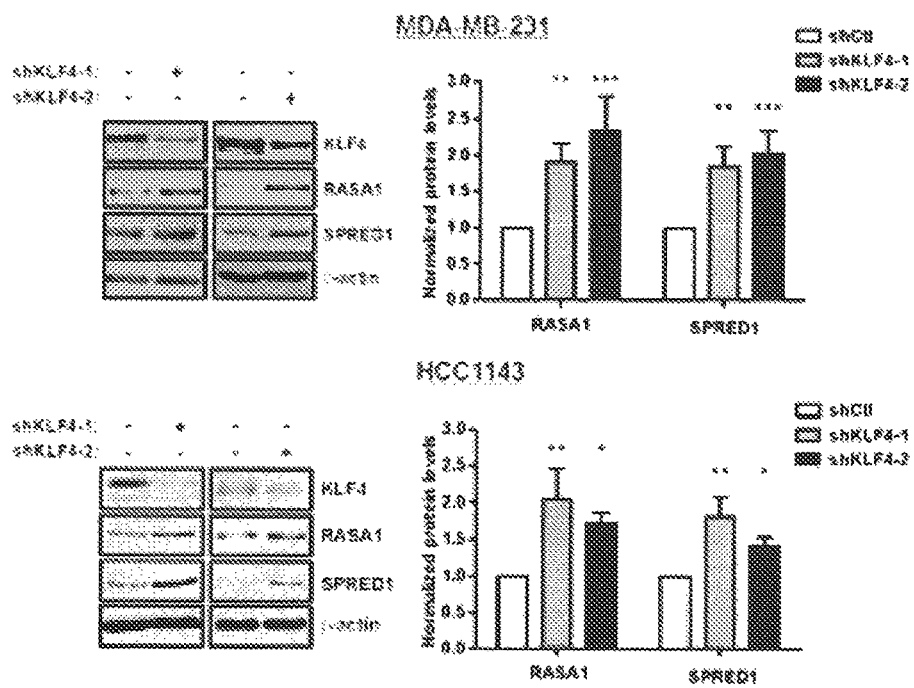
FIGS. 3A, 3B, and 3C show: KLF4 and miR-206 regulate the levels of two RAS-ERK pathway suppressors, RASA1 and SPRED1.
Figure 3B:
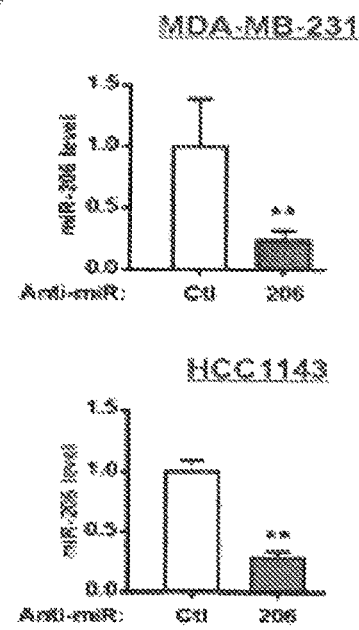
Figure 3C:
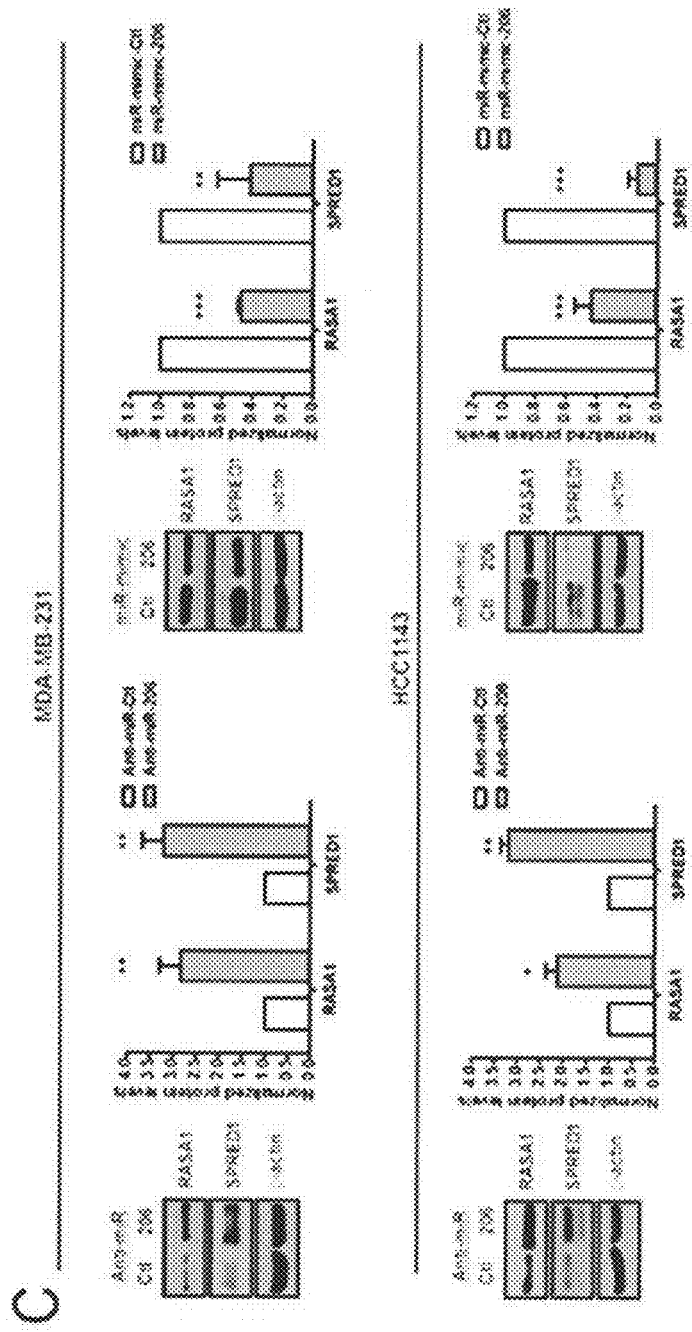

Consistent with the mutual dependence of both miR-206 and RAS-ERK activity upon KLF4, we sought to identify specific components of the RAS-ERK pathway that are regulated by this miR. The two RAS-ERK pathway suppressors RASA1 and SPRED1 were consistently identified as likely miR-206 targets across multiple miR algorithms (Table 2). Consistent with regulation by miR-206, KLF4 depletion was associated with higher levels of RASA1 and SPRED1 (FIG. 3A). To examine a role for endogenous miR-206 we utilized antisense inhibitor specific to the mature miR (anti-miR). As compared to the control, anti-miR-206 depleted the miR levels in TNBC cells (FIG. 3B). This suppression of miR-206 activity was sufficient to increase the levels of the two pathway inhibitors (FIG. 3C, left panels). Conversely, transfection of exogenous miR-206 (miR-206-mimic) decreased the level of each protein (FIG. 3C, right panels). These results identified miR-206 as a potential link between KLF4 and RAS-ERK signaling.

Figure 4A:
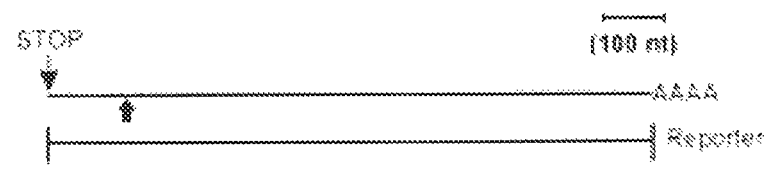
FIGS. 4A, 4B, 4C, and 4D show: miR-206 represses the translation of RASA1 and SPRED1 by directly targeting the 3' UTRs.
Figure 4B:
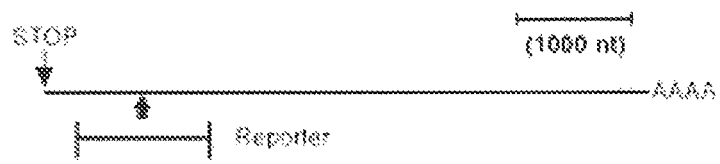
Figure 4C:
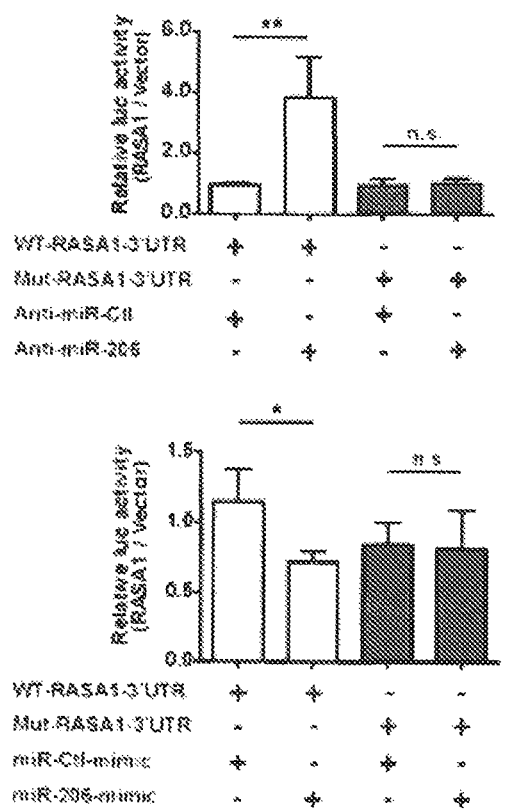
Figure 4D:
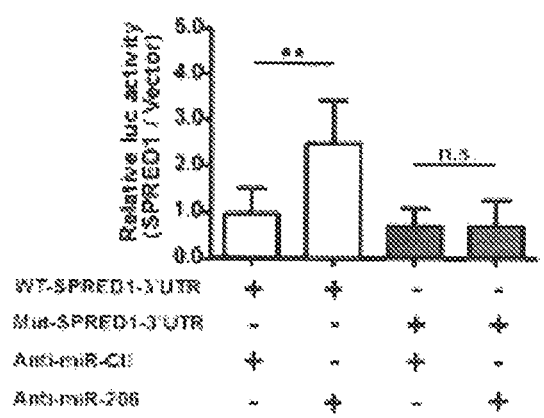
Figure 4D:
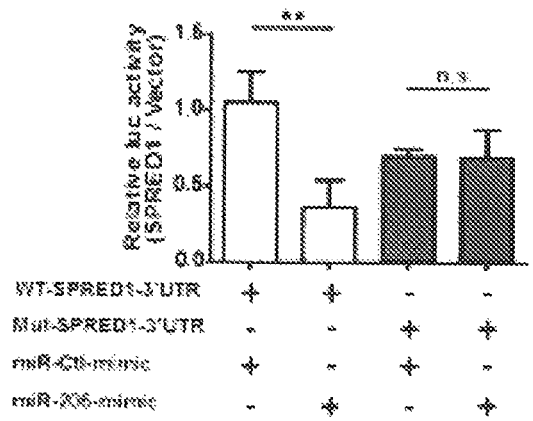

To analyze the regulation of protein translation by miR-206, we utilized translational reporter assays. Fragments of the 3' UTRs containing putative miR-206 binding sites were cloned downstream of the open reading frame of firefly luc (FIGS. 4A-4B). Relative to the control anti-miR, in MDA-MB-231 cells transfected with anti-miR-206, the luc activity was 3.9 fold induced for the WT RASA1 reporter and 2.4 fold induced for the WT SPRED1 reporter (FIGS. 4C-4D, upper and middle panels). Conversely, transfection of each reporter with miR-206-mimic decreased luc activity by 32% for the RASA1 reporter and by 64% for the SPRED1 reporter (FIGS. 4C-4D, lower panels). Reporter regulation by miR-206 was abolished by mutation of RASA1 or SPRED1 sequences important for miR-206 binding (FIGS. 4C-4D). These results identify miR-206 as a direct regulator of these transcripts, supporting a role for KLF4 in promotion of RAS-ERK signaling through miR-206 mediated suppression of RASA1 and SPRED1.

miR-21 is a KLF4-Dependent miR that Represses the Translation of Both RASA1 and SPRED1.

As modulation of miR-206 alone was not sufficient to recapitulate the effects of KLF4 on pERK 1/2 levels, we therefore sought additional downstream effectors. Similarly to miR-206, miR-21 is upregulated in breast cancer and is predicted by pathway enrichment analysis to regulate MAPK signaling ($p=2.09\times10^{-3}$; Table 3) (59). Furthermore, miR-21 has been validated to directly regulate the translation of several RAS-ERK-activator protein 1 (AP-1) inhibitory components, including RASA1, SPRY1, SPRY2, and PDCD4 (56-58). These common features suggested the possibility of shared signaling by these two miRs. Providing compelling support for this idea, MAPK signaling was ranked first among the pathways likely to be co-regulated by miR-206/21 ($p=3.00\times10^{-4}$; Table 4).

Figure 5A:
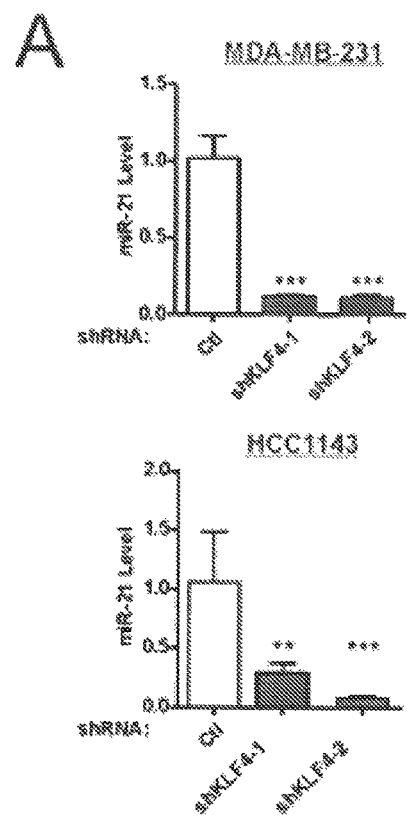
FIGS. 5A, 5B, 5C, 5D, 5E, 5F, and 5G show: Endogenous KLF4 is bound to the MIR21 promoter region and maintains miR-21 expression in TNBC cells.
Figure 5B:
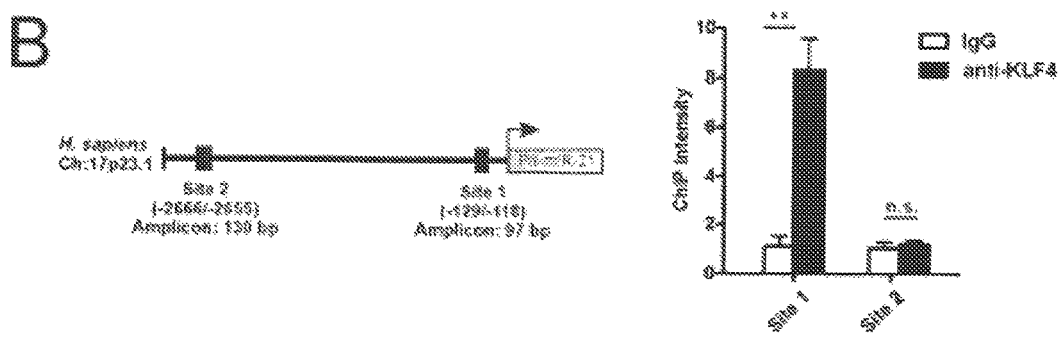
Figure 5C:
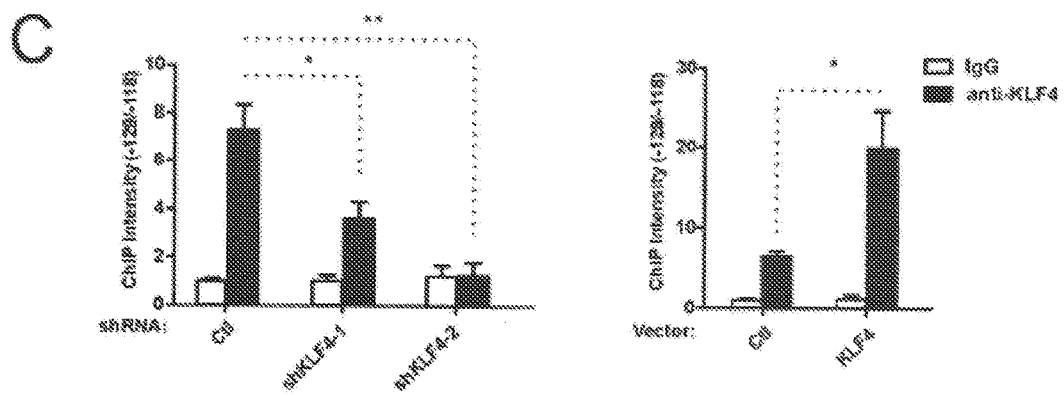
Figure 5D:
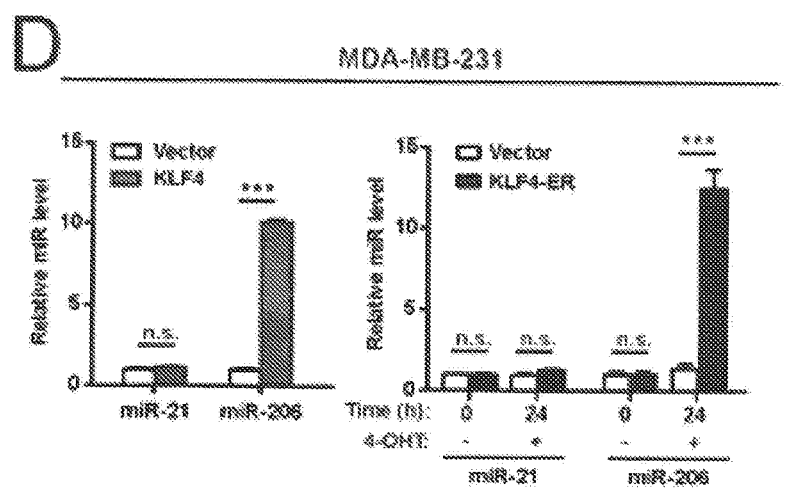
Figure 5E:
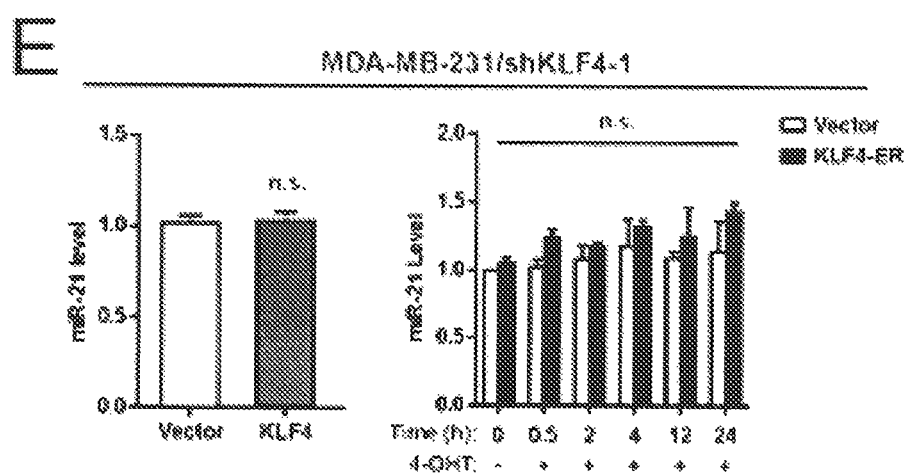

The ability of KLF4 to regulate RAS-ERK signaling, and the established role of miR-21 in regulation of this pathway identified KLF4 as a potential regulator of miR-21. To determine whether KLF4 might signal through miR-21, we assayed KLF4-deficient TNBC cells for miR-21 levels, observing marked suppression (FIG. 5A). ChIP analysis of KLF4 at consensus sites in the MIR21 locus of MDA-MB-231 cells identified enrichment of site 1, located within the promoter region (FIG. 5B). This enrichment was reduced in KLF4-deficient cells and increased in cells with exogenous KLF4 (FIG. 5C). In contrast to the enhanced ChIP intensity signal in cells with exogenous KLF4, miR-21 levels were not enhanced (FIG. 5D). Restoration of KLF4 in MDA-MB-231/shKLF4 cells was likewise insufficient to increase miR-21 (FIG. 5E). As a control, miR-206 levels were induced by exogenous KLF4 in these experiments (FIG. 5D), suggesting different modes of miR regulation by KLF4.

Figure 5F:
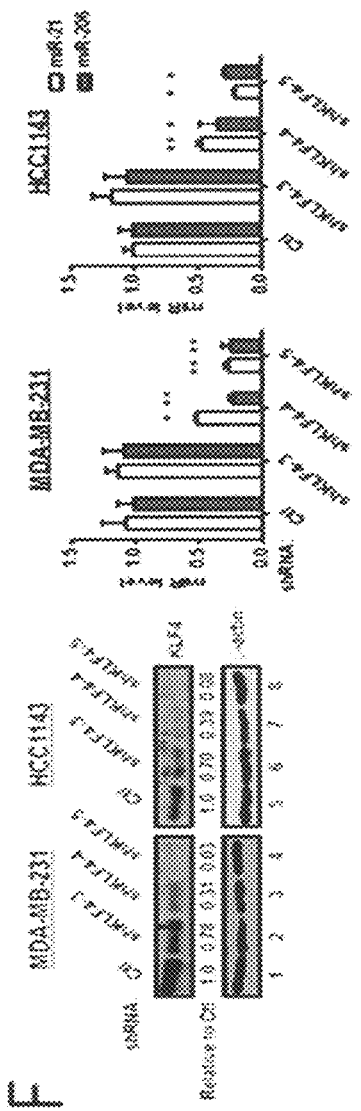

To address possible off-targeting by KLF4 shRNAs (shKLF4), we analyzed additional shKLF4 constructs. We observed only weak activity of shKLF4-3, but more efficient KLF4 suppression by shKLF4-4 and shKLF4-5 (FIG. 5F, left panels). Compared to shCtl and shKLF4-3, cells transduced with the active constructs had consistently reduced levels of miR-21 (FIG. 5F, right panels). Consequently, the regulation of miR-21 by endogenous KLF4 was supported by a total of four active shRNAs (FIGS. 5A and 5F).

Figure 5G:
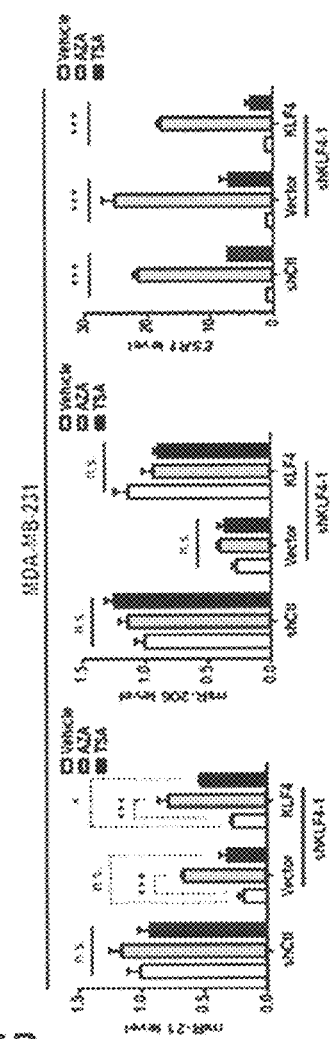

The failure of exogenous KLF4 to restore miR-21 levels appeared consistent with a stable alteration of MIR21 chromatin in KLF4-deficient cells (71,72). To examine this possibility we treated shCtl cells or shKLF4-1 cells with the DNA methyltransferase inhibitor AZA or the histone deacetylase inhibitor TSA (FIG. 5G). Unlike TSA, AZA largely restored miR-21 levels (FIG. 5G, left panel). Neither AZA nor TSA significantly altered miR-206 levels, whereas ESR1 served as a positive control and was induced by both agents (FIG. 5G, middle and right panels respectively) (73,74). These results show that endogenous KLF4 is permissive for the expression of miR-21 in TNBC cells, and support a role for chromatin modification in the suppression of miR-21 following KLF4 depletion.

Figure 6A:
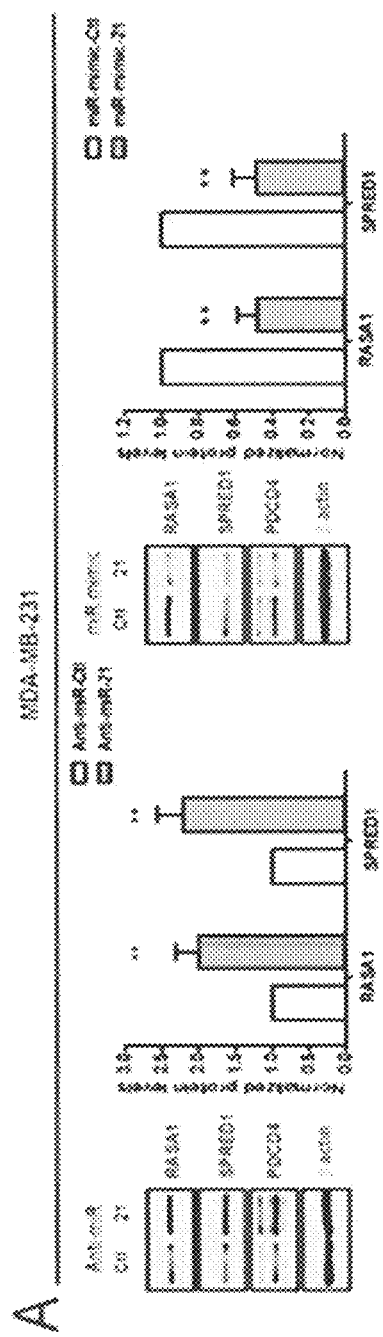
FIGS. 6A, 6B, 6C, 6D, and 6E show: miR-21 directly represses the translation of RASA1 and SPRED1.
Figure 6B:
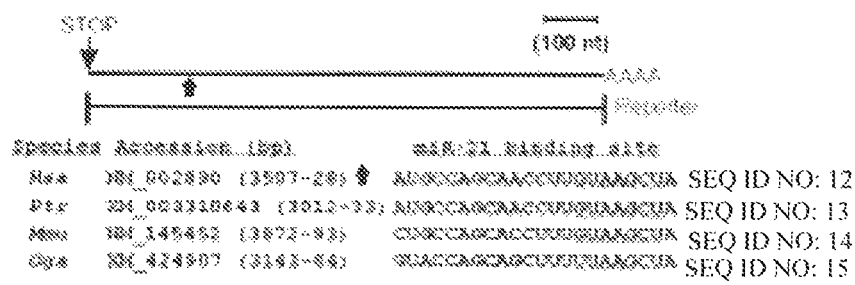
Figure 6C:
Figure 6D:
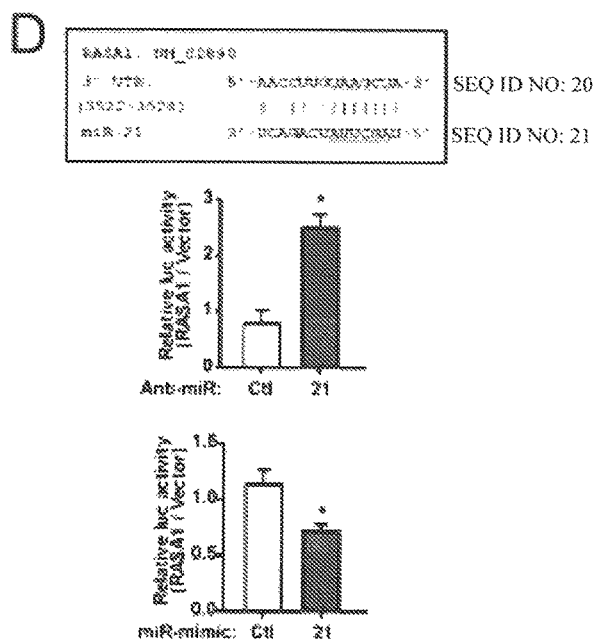
Figure 6E:
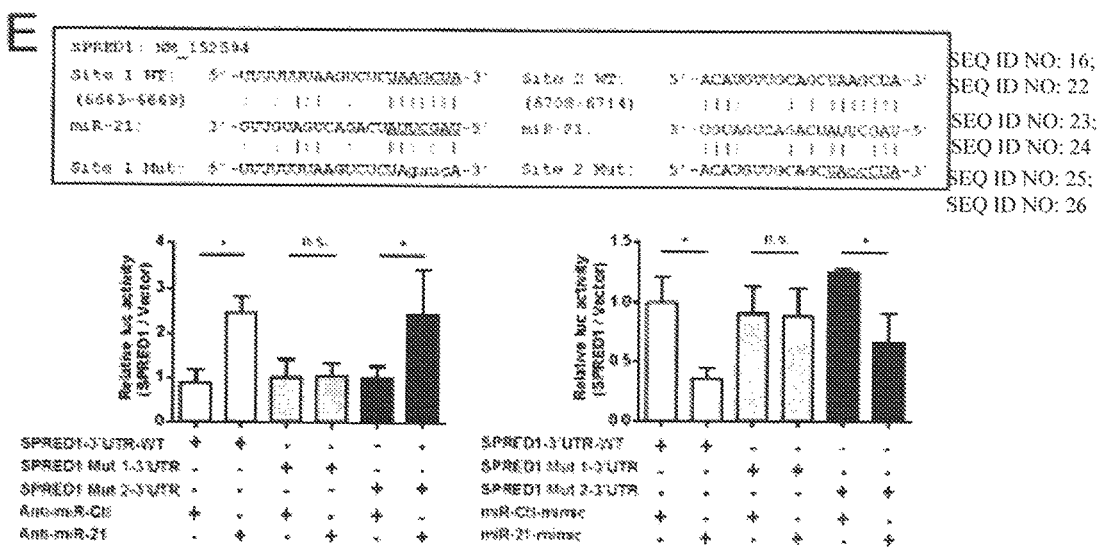

The regulation of RASA1 by miR-21 is well established (64). Our results above indicate that RASA1 is co-targeted by miR-206/21, suggesting a broader role for this pair as co-regulators of RAS-ERK pathway components (FIG. 4). Although miR-206 was predicted to regulate SPRED1 and this was subsequently validated, whether miR-21 can likewise regulate this factor was unknown. Nevertheless, transfection of anti-miR-21 into MDA-MB-231 cells increased the protein levels of both RASA1 and SPRED1, whereas exogenous miR-21 was suppressive (FIG. 6A). Unlike the well-conserved miR-21 sites in RASA1, analysis in TargetScan revealed that SPRED1 contains two candidate binding sites for miR-21 with only limited species conservation (FIGS. 6B-6C) (75). Translational reporter assays identified only one of these sites as functional, and supported the direct regulation of both RASA1 and SPRED1 transcripts by miR-21 (FIGS. 6D-6E). As a control, transfection of anti-miR-21 led to reduced miR-21 activity, as indicated by immunoblot analysis of PDCD4, a well-established target of this miR (FIG. 6A) (63). These results validate SPRED1 as a miR-21 targeted transcript. Therefore, the miR-206/21 pair can indeed co-target distinct RAS-ERK pathway components, validating the idea that MAPK signaling represents an important signaling intersection for these two miRs (Table 4).

Consistent KLF4 Regulation of miR-206/21 Levels and RAS-ERK Signaling in RAS-WT and RAS-Mutant Tumor Cells.

Figure 7A:
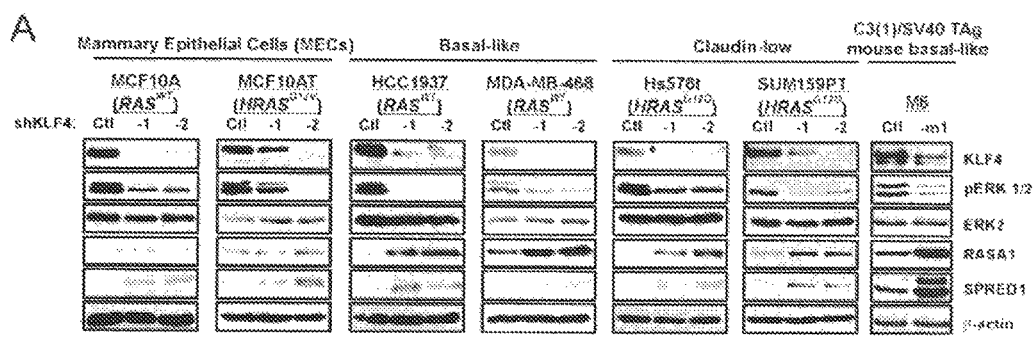
FIGS. 7A and 7B show: KLF4 promotes activated ERK 1/2 levels, miR-206, and miR-21 expression in a panel composed of human mammary epithelial cells and TNBC cell lines.
Figure 7B:
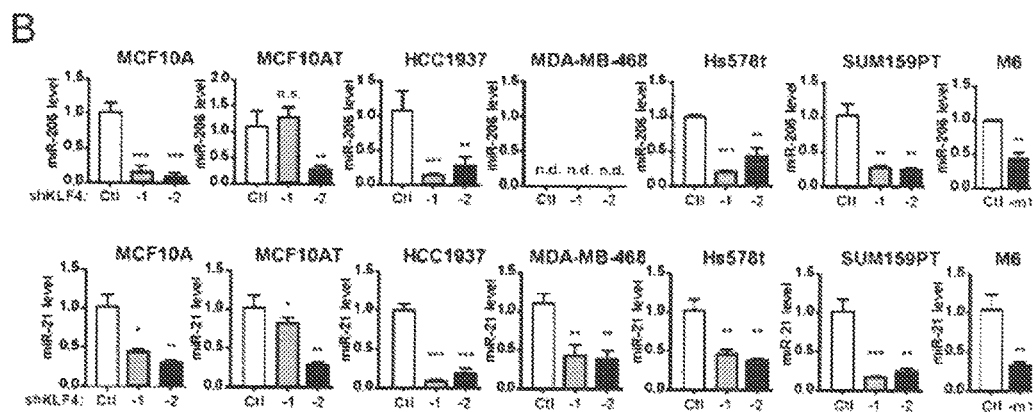

The results observed for MDA-MD-231 and HCC1143 cells suggested a functional relationship between the KLF4-miR-206/21 axis and the RAS-ERK pathway. We analyzed this signaling in a broader panel of mammary epithelial cells (MECs) and cancer cells (FIG. 7A). KLF4 depletion in nontumorigenic MCF10A cells, in HRAS-mutant MCF10AT cells, or in a variety of human or mouse TNBC lines led to consistently reduced levels of activated ERK 1/2 and to increased levels of RASA1 and/or SPRED1. In the KLF4-deficient TNBC cells, RASA1 and SPRED1 were concordantly upregulated. However, in MECs, the RASA1 levels were not appreciably altered, and reduced pERK 1/2 levels were associated with increased SPRED1 alone. KLF4 depletion was likewise associated with reduced miR-206/21 levels, except in MDA-MB-468 cells where miR-206 was undetected (FIG. 7B). In this miR-206-deficient cell line, the overall effect of KLF4 on pERK 1/2 appeared more modest. In summary, KLF4-miR-206/21 signaling appears to generally regulate the RAS-ERK pathway in TNBC cells, with similar effects in RAS-WT (HCC1143, HCC1937, and MDA-MB-468) and RAS-mutant cells (MDA-MB-231, Hs578t, and SUM159PT).

miR-206 and miR-21 Cooperate to Promote RAS-ERK Signaling and ERK 1/2 Dependent Phenotypes.

Figure 8A:
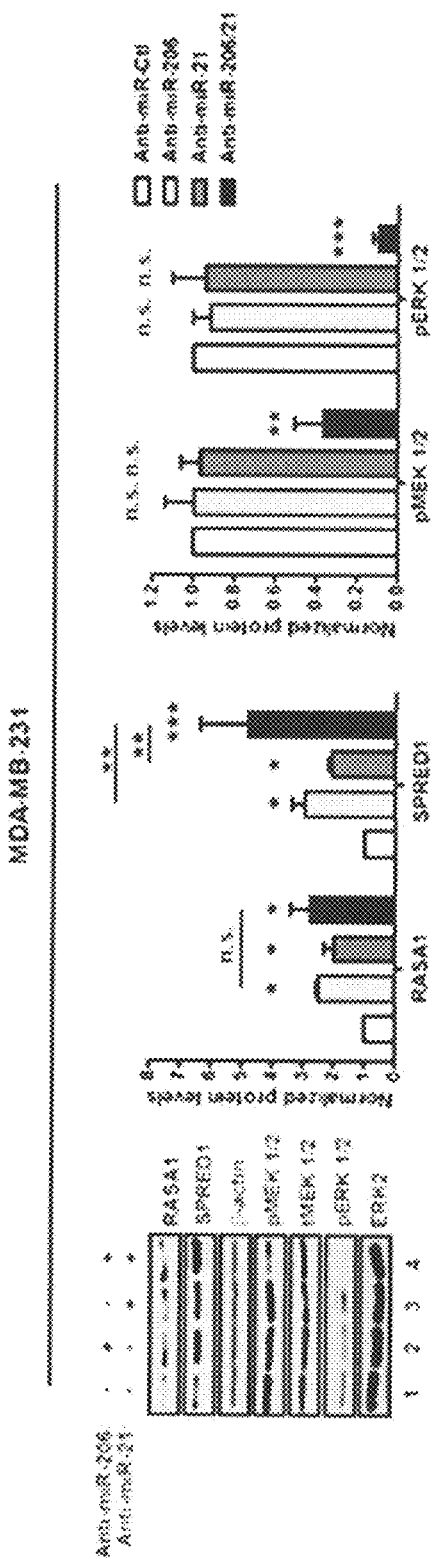
FIGS. 8A and 8B show: Endogenous miR-206 and miR-21 cooperate to promote RAS-ERK signaling.
Figure 8B:
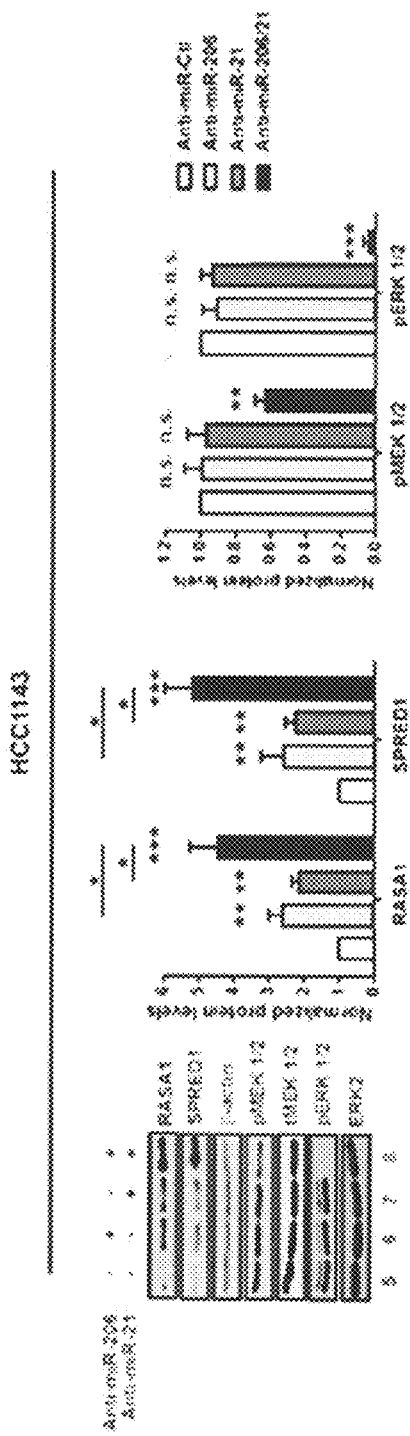

Transfection of anti-miR-206 or anti-miR-21 alone did not have prominent effects on pERK 1/2 levels (FIG. 8, lanes 2, 3, 6, and 7). To test for cooperativity, we inhibited both miRs in TNBC cells (i.e., anti-miR-206/21), and then assayed for RASA1 and SPRED1 levels (FIG. 8, lanes 4 and 8). Compared to the individual anti-miRs, SPRED1 was consistently induced to a greater extent by anti-miR-206/21. In contrast, RASA1 levels responded to each of the anti-miRs (FIG. 8, lanes 2 and 6), but anti-miR-206/21 cooperativity was only apparent in HCC1143 cells (FIG. 8, lanes 4 and 8). Nevertheless, anti-miR-206/21 transfection of TNBC cells reduced the levels of pMEK 1/2 and pERK 1/2 to a greater extent than did either anti-miR when used alone. These findings identify two KLF4-dependent miRs as maintenance factors for RAS-ERK signaling in TNBC cells, potentially through cooperativity for regulation of SPRED1 and/or other pathway regulators.

Figure 9A:
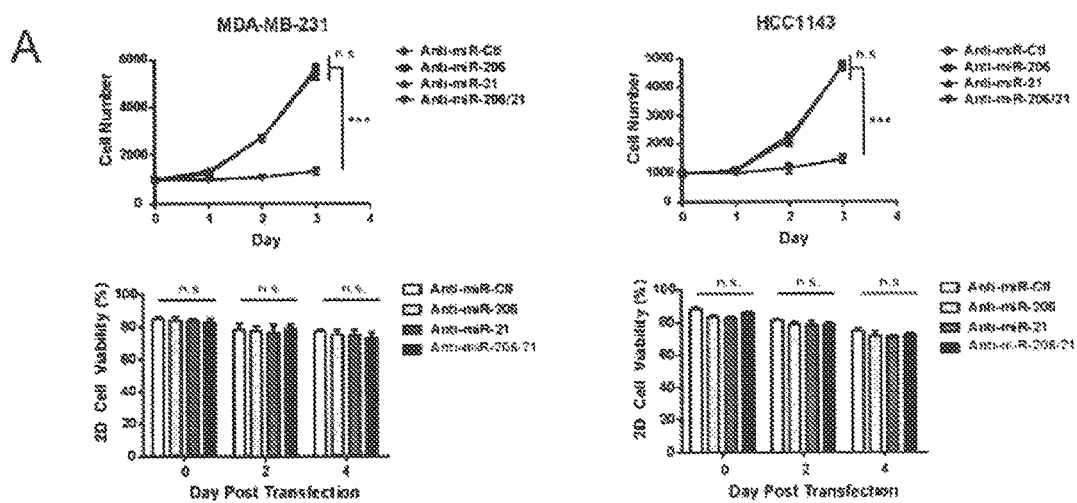
FIGS. 9A, 9B, 9C and 9D show: Inhibition of miR-206 and miR-21 cooperatively suppresses ERK 1/2 dependent phenotypes in TNBC cells.

In breast cancer cells the RAS-ERK pathway promotes cell proliferation, migration, and resistance to cell death (21,22). TNBC cells transfected with both anti-miRs displayed slower growth over a three day time course than did control or single anti-miR transfected cells (FIG. 9A, upper panels). This marked attenuation of proliferation was not explained by changes in cell viability as measured by trypan blue exclusion (FIG. 9A, lower panels).

Figure 9B:
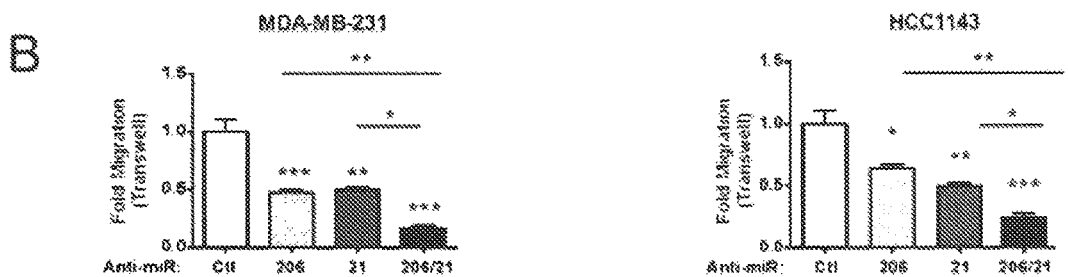
Figure 9C:
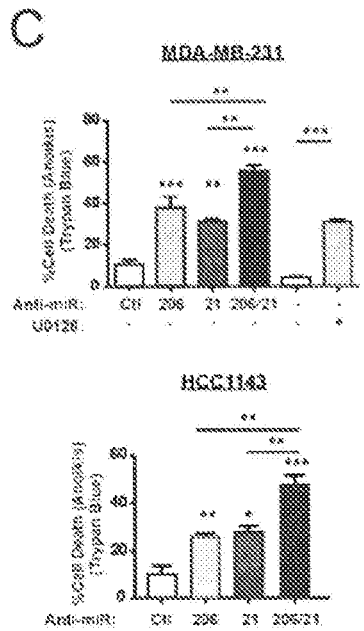
Figure 9D:
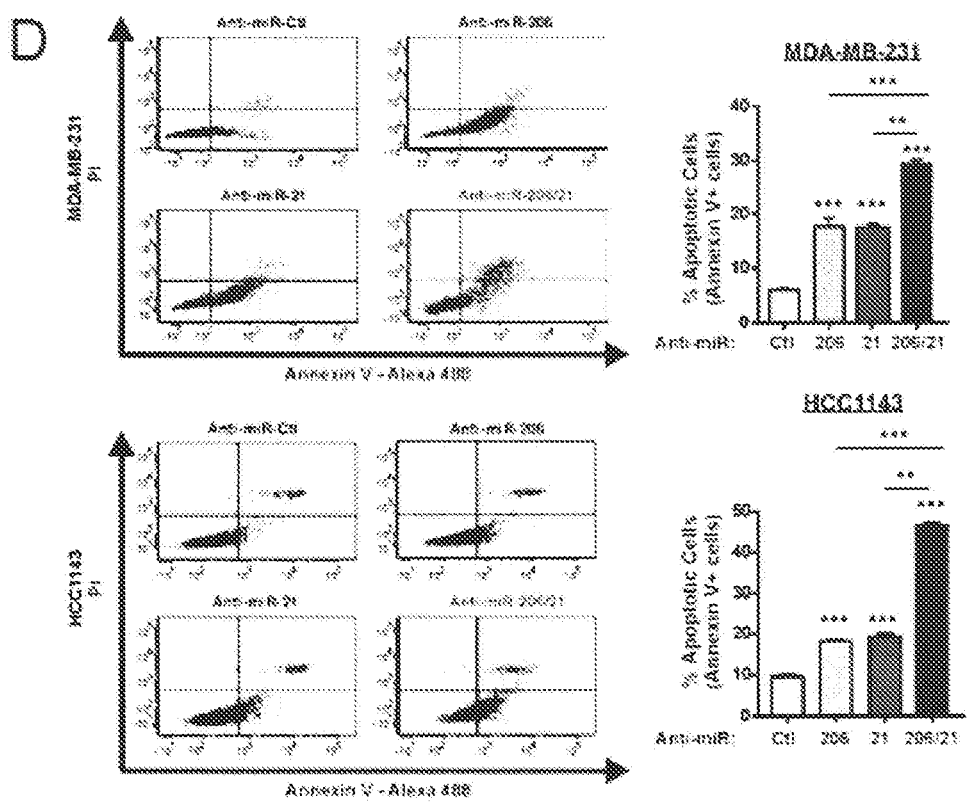

Similarly to cell proliferation, inhibition of both miRs abrogated TNBC cell migration in transwell chambers to a greater extent than the inhibition of either miR alone (FIG. 9B). Finally, anti-miR-206/21 rendered TNBC cells more susceptible to cell death in anoikis assays (FIG. 9C-9D). As a control, treatment of matrix-deprived MDA-MB-231 cells with the MEK 1/2 inhibitor U0126 yielded a higher rate of cell death (76). These results indicate that miR-206/21 can cooperate to promote RAS-ERK pathway signaling as well as pathway dependent phenotypes.

miR-206 and miR-21 Promote RAS-ERK Signaling by Repression of RASA1 and SPRED1.

Figure 10A:
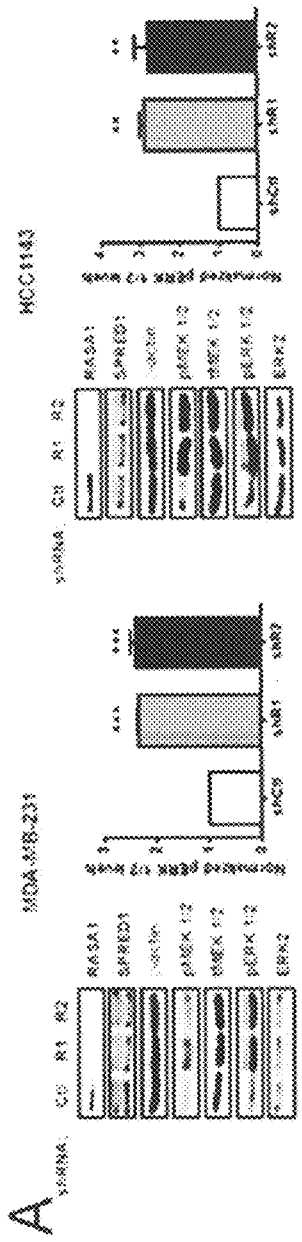
FIGS. 10A, 10B, 10C, and 10D show: RASA1 and SPRED1 are limiting factors for RAS-ERK signaling in TNBC cells.
Figure 10B:
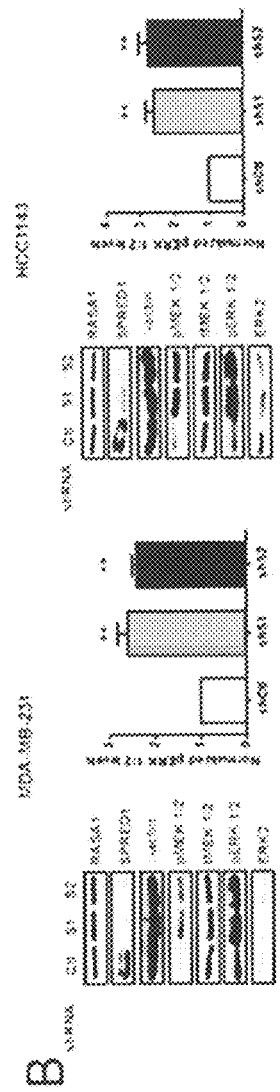
Figure 10C:
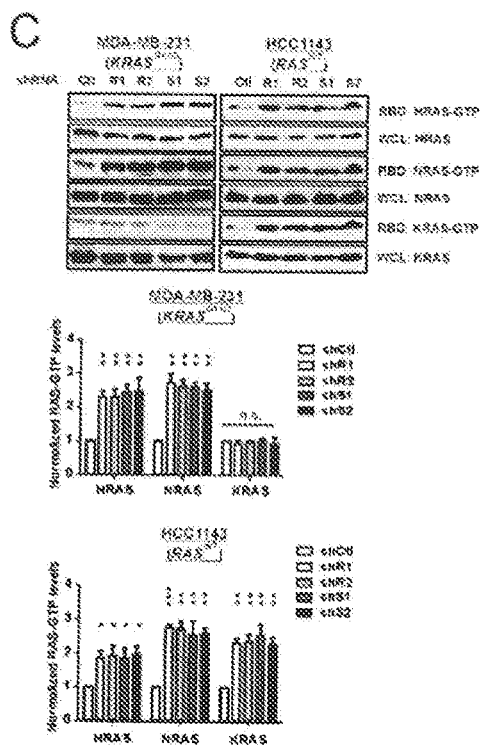
Figure 10D:
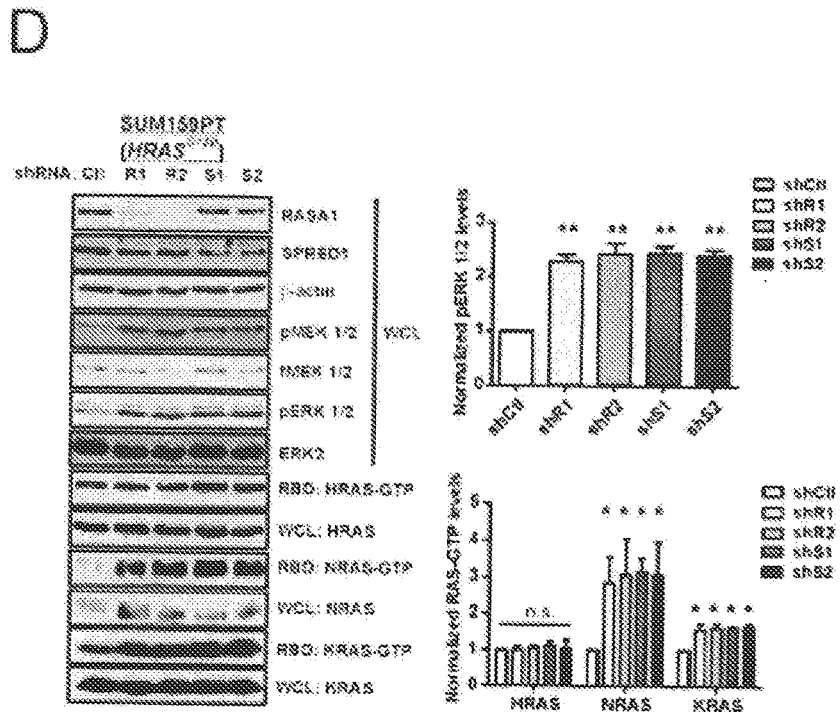

To determine whether miR-206/21 impact RAS-ERK signaling through their co-regulation of RASA1 and/or SPRED1, we depleted either RASA1 (FIG. 10A) or SPRED1 (FIG. 10B). Knockdown of either factor had little effect upon the other protein. Regardless of the RAS mutational status, knockdown of RASA1 or SPRED1 led to increased steady-state levels of pERK 1/2 relative to control cells. This increase in pathway activity was associated with elevated levels of WT RAS-GTP (FIG. 10C). In contrast to the results obtained for WT RAS proteins, the KRAS-GTP levels in MDA-MB-231 cells (KRAS$^{G13D}$) were not appreciably altered by suppression of RASA1 or SPRED1. Similarly, the HRAS-GTP levels in SUM159PT cells (HRAS$^{G12D}$) were unchanged by suppression of either RASA1 or SPRED1, even though pERK 1/2 levels were increased (FIG. 10D). These results suggest that WT RAS proteins mediate the enhanced RAS-ERK pathway activity in RASA1- or SPRED1-deficient TNBC cells.

Figure 11A:
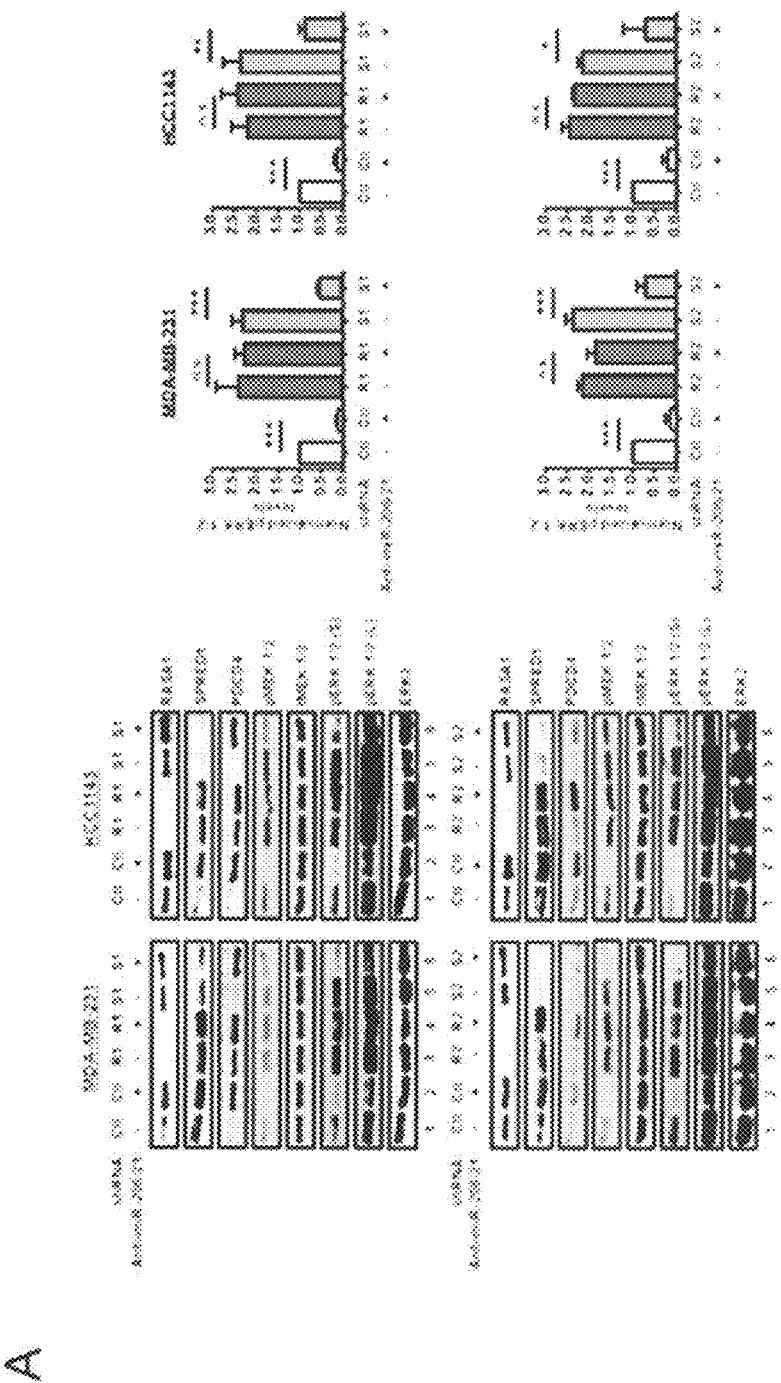
FIGS. 11A, 11B, and 11C show: RASA1 and SPRED1 mediate the regulation of RAS-ERK pathway signaling by miR-206 and miR-21.

To test for a function of RASA1 and SPRED1 as mediators of miR-206/21 effects on RAS-ERK signaling, we delivered anti-miR-206/21 to control cells or cells deficient in either protein (FIG. 11A). As an indicator of successful miR suppression we assayed the protein levels of PDCD4, which is regulated by miR-21. As expected, combined miR-206/21 inhibition in control cells reduced the levels of pERK 1/2 (FIG. 11A; lanes 1-2 in each panel). Suppression of RASA1 rendered cells largely independent of miR-206/21, as pERK 1/2 showed little or no attenuation by anti-miR (lanes 3-4). In SPRED1-suppressed cells, RASA1 and/or some other miR-206/21-dependent component appeared to be limiting for pathway activity, as anti-miRs induced RASA1 and also suppressed the levels of pERK 1/2 (lanes 5-6). In TNBC cells depleted of RASA1 or SPRED1 and then treated with anti-miR-206/21, the residual activated ERK 1/2 was increased relative to control cells (FIG. 11A, lanes 2, 4, and 6). This anti-miR-resistant signaling supports functional roles for both RASA1 and SPRED1 as mediators of the KLF4-dependent miRs.

Figures 11B, 11C:
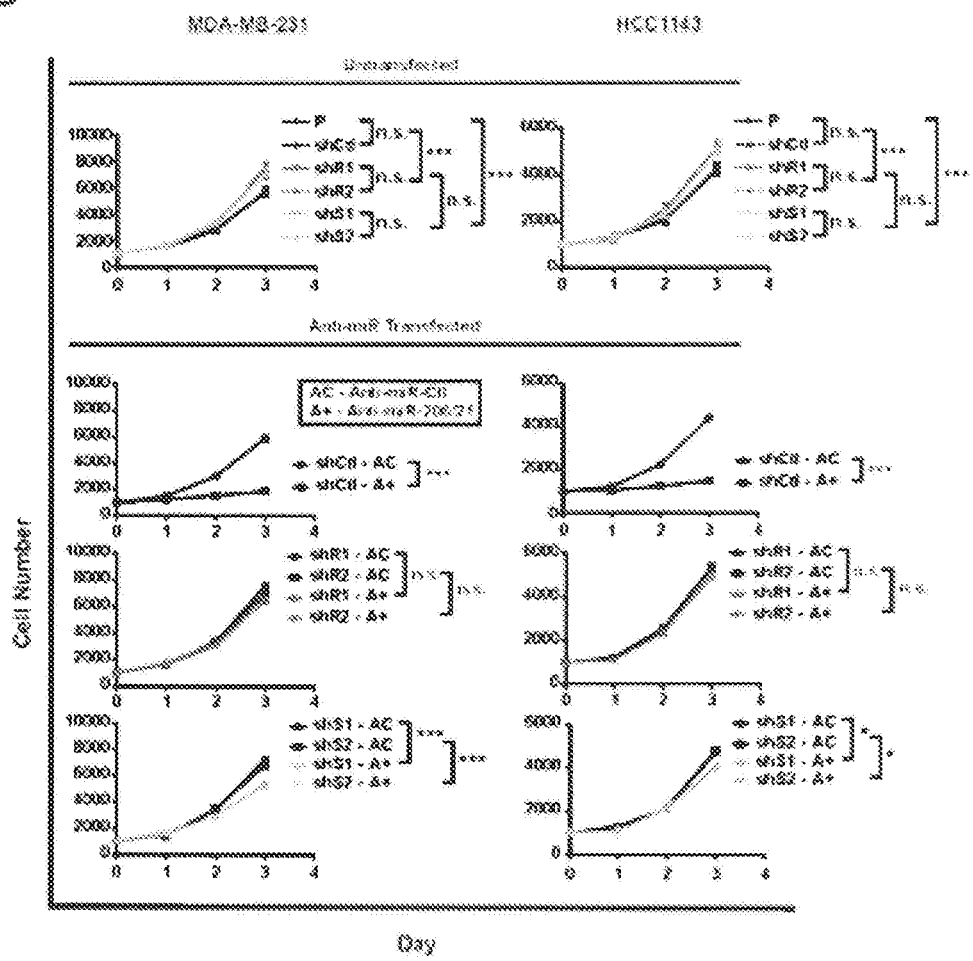

Phenotypic data consistent with these immunoblot results were obtained by analysis of cell proliferation (FIG. 11B). Compared to parental (untransduced and untransfected) TNBC cells or control (shCtl) cells, shRASA1 and shSPRED1 cells proliferated at a rate that was only slightly faster. For each cell line we next measured cell proliferation following treatment with either anti-miR-Ctl or anti-miR-206/21. Whereas shCtl cells transfected with anti-miR-206/21 proliferated much more slowly (p<0.001), shRASA1 cells displayed anti-miR-206/21-resistant cell proliferation (p>0.05; FIG. 11B). shSPRED1 cells had an intermediate phenotype, with a smaller size effect than observed for shCtl cells that were treated with anti-miR-206/21 (p<0.05; FIG. 11B). The effects of anti-miR-206/21 on cell proliferation appeared consistent with the residual levels of activated ERK 1/2 (see FIG. 11A).

Consistent results were obtained when anti-miR-treated TNBC cells were orthotopically injected into the mammary gland of immunodeficient mice (FIG. 11C). Relative to anti-miR-Ctl, anti-miR-206/21 suppressed tumor initiation by the control cells (shCtl), attributed to their decreased proliferation and/or increased cell death following implantation into the mammary gland. In contrast, cells deficient in RASA1 or SPRED1 were competent for tumor initiation. These results support functional roles for both RASA1 and SPRED1 in miR-206/21 signaling.

Restoration of RAS-ERK Signaling by Exogenous miR-206/21 in KLF4-Depleted Cells Promotes Resistance to Cell Death.

Figure 12A:
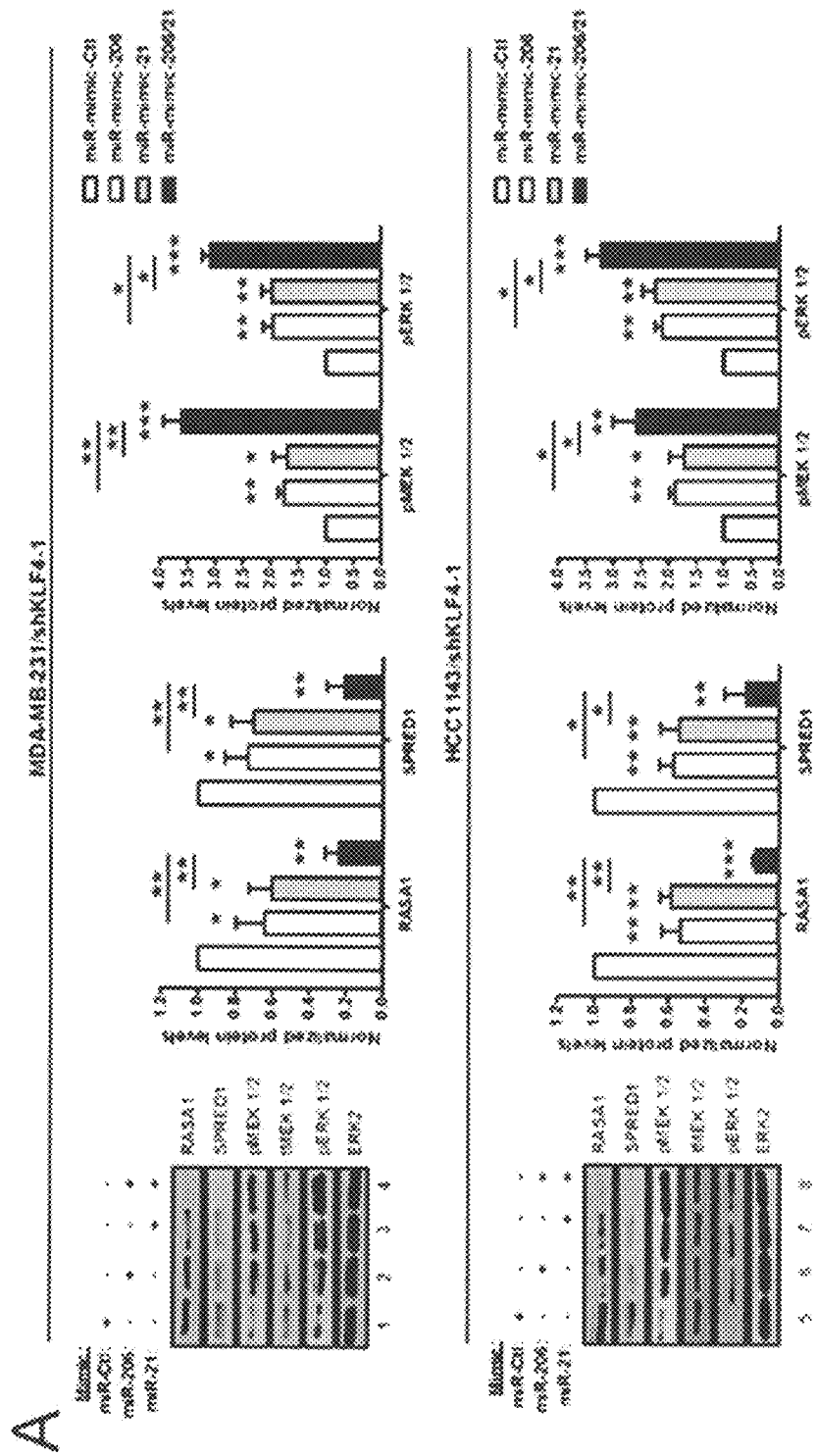
FIGS. 12A and 12B show: Exogenous miR-206 and miR-21 cooperate to promote RAS-ERK signaling and cell survival in KLF4-depleted cells.

To complement the anti-miR data, we delivered exogenous miRs into KLF4-deficient TNBC cells (FIG. 12A). As compared to the individual miR-mimics (FIG. 12A, lanes 2, 3, 6, and 7), more pronounced signaling effects were obtained using the miR-206/21-mimic (lanes 4 and 8). These effects included suppression of RASA1 and SPRED1 and the induction of activated MEK 1/2 and ERK 1/2.

Figure 12B:
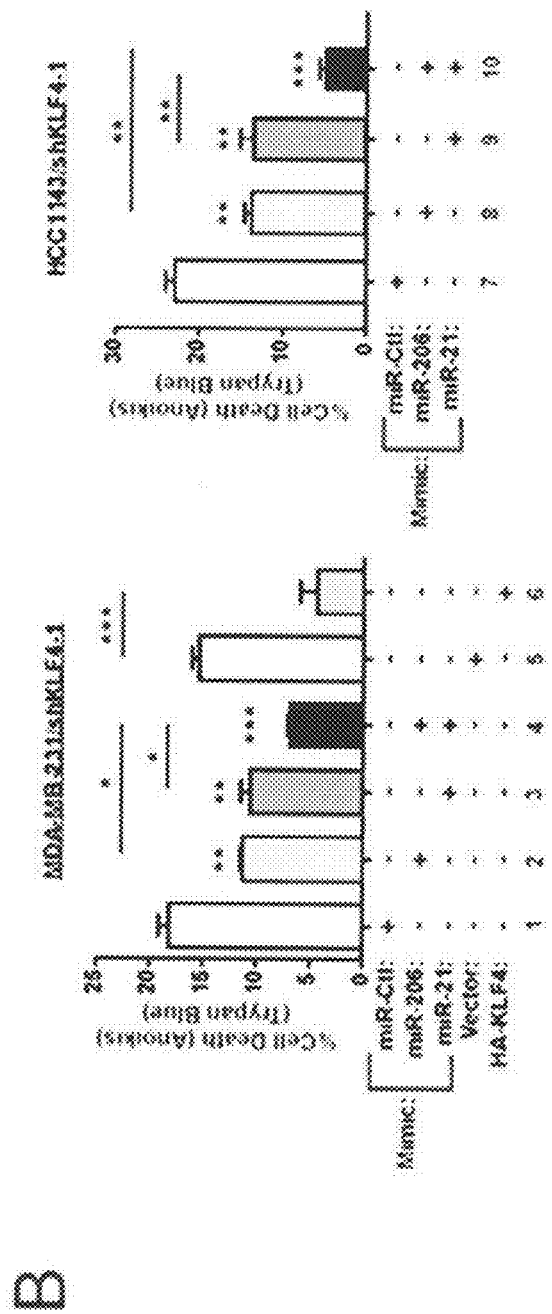
Figure 13:
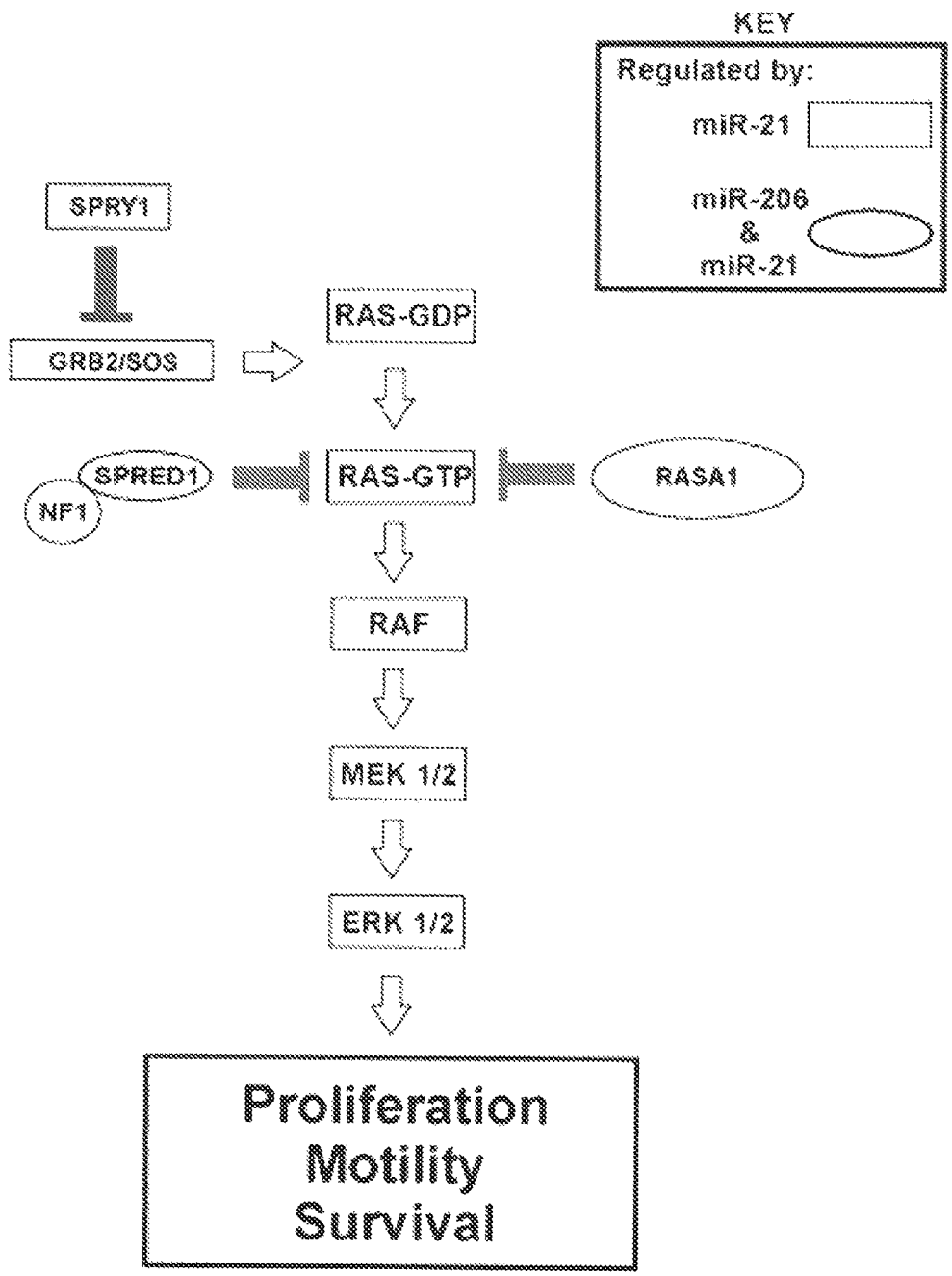
FIG. 13 shows: KLF4-dependent miRs cooperatively promote RAS-ERK pathway activity by co-targeting of pathway inhibitors.

Relative to the control, transfection of either miR-206- or miR-21-mimic into KLF4-depleted cells reduced the cell death following matrix deprivation (FIG. 12B, lanes 2, 3, 8, and 9). Consistent with the cooperative regulation of pERK 1/2 levels (FIG. 12A, lanes 4 and 8), a greater fold effect on cell death was observed for cells treated with both mimics (FIG. 12B, lanes 4 and 10). In these studies, exogenous KLF4 effects were similar to that of the miR-mimics, and suppressed cell death (FIG. 12B, left panel, lanes 5 and 6). These gain-of-function studies provide independent support for the cooperative regulation of RAS-ERK signaling by KLF4-dependent miRs-206/21. In the light of previous studies by others, our results support a model for miR-206/21 co-targeting and co-regulation of RAS-ERK signaling (FIG. 13).

Compared to other breast cancer subtypes, TNBCs express elevated levels of RTKs such as EGFR and FGFRs that represent major regulators of RAS-ERK signaling (30, 77). Although genetic changes in these receptors or the mutational activation of RAS or RAF are rare, these tumors often harbor other genetic alterations that promote RAS-ERK pathway activity (26-31). Supporting the importance of this signaling, TNBC cells are particularly sensitive to drugs such as MEK or PI3K inhibitors, and combination therapies have been analyzed in clinical trials (23,24,78,79).

KLF4 is a major regulator of pluripotency with the potential to either promote or suppress malignant properties, and dissecting the relevant mechanisms has the potential to identify new therapeutic approaches. We previously implicated miR-206 as a potential downstream effector of KLF4 (55). Evidence from the current study supported a direct role of KLF4 in regulation of miR-206. Consistent with a role for this signaling in TNBCs, miR-206 is upregulated in breast cancer and ER-negative tumors express higher levels relative to ER-positive tumors (59,80).

miR-206 has been well characterized in muscle cells, where it promotes skeletal muscle regeneration in response to injury (81-83). An in silico search for cancer-relevant influences of miR-206 identified regulation of MAPK signaling as a likely effector pathway, with potential effects on RASA1 and SPRED1 (Tables 1-2). Subsequently, analysis of KLF4-deficient cells revealed upregulation of these two pathway inhibitors in conjunction with markedly reduced levels of pERK 1/2, and protein translation reporter studies identified direct roles for miR-206 in regulation of RASA1 and SPRED1.

As compared to the pronounced effect of endogenous KLF4 on pERK 1/2 levels, modulation of miR-206 alone revealed only modest effects (FIG. 12A), and we therefore sought additional effectors downstream of KLF4. We evaluated miR-21 as a candidate because of its upregulation in breast cancer and its known role in regulation of RAS-ERK pathway components, including RASA1 (Table 3) (58-65). Strikingly, an intersection approach identified MAPK signaling as the pathway most likely to be co-regulated by miR-206/21 (Table 4). We subsequently observed a critical role for endogenous KLF4 in maintenance of miR-21 levels, and found that both RASA1 and SPRED1 contain binding sites for miR-206/21. These results identified a recurrent regulatory strategy in which two KLF4-regulated miRs can impact the same transcript. As shown by suppression of KLF4 or by the introduction of anti-miR-206/21, this regulation results in pronounced alteration of RAS-ERK signaling in the multiple TNBC models examined.

The protumorigenic miR-21 is abundant in TNBC cells and inhibits the translation of multiple negative regulators of RAS-ERK-AP1 signaling (FIG. 13). Despite extensive interactions with the RAS-ERK pathway, we and others have observed that antisense-mediated inhibition of endogenous miR-21 gives relatively modest effects on overall pathway activity, as indicated by analysis of activated ERK 1/2 (FIG. 8). In the current study, we observed that miR-206/21 function as a pair to co-target RAS-ERK pathway inhibitory proteins, with profound consequences on RAS-ERK signaling. Such co-targeting is not without precedent. For example, miR-27a, miR-96, and miR-182 co-target the tumor suppressor FOXO1 in breast cancer cells (84).

Our analysis of KLF4-depleted TNBC cells indicated that endogenous KLF4 could influence the levels of both miR-206 and miR-21, a response obtained using each of four distinct KLF4 shRNAs (FIGS. 5A and 5F). We also characterized the temporal KLF4 regulation of miR levels using a 4OHT-conditional KLF4-ER fusion protein. In combination with ChIP data that strongly supported direct interaction of KLF4 with the promoter-proximal regions of MIR206 and MIR21, these studies implicated MIR206 and MIR21 as direct transcriptional targets of KLF4, but with distinct modes of regulation.

Unlike for the regulation of MIR206, we observed that endogenous and exogenous KLF4 function discordantly for regulation of MIR21. Previous studies have shown that MIR21 is transcribed as an independent unit located in the intron of the TMEM49 gene (85). Relative to the control cells, in KLF4-deficient cells we observed a decrease of TMEM49 of similar to 35% (not shown). Unlike for miR-206, exogenous KLF4 did not alter miR-21 levels in TNBC cells. Similarly, restoration of KLF4 activity in KLF4-depleted tumor cells induced miR-206 but did not significantly alter miR-21 levels. The insufficiency of exogenous KLF4 for induction of miR-21 suggests an "on-off" mode of regulation, and identifies KLF4 suppression as a potential hit-and-run strategy for the therapeutic silencing of miR-21 in tumors. Also, this lack of regulation of miR-21 by exogenous KLF4 is quite consistent with the more limited effect of exogenous KLF4 on activated ERK 1/2 levels relative to the endogenous transcription factor (FIGS. 2A and 2C).

These results suggested a working model in which endogenous KLF4 maintains an open chromatin structure at MIR21. Initial support for this model was obtained by analyzing a role for DNA methylation. In KLF4-deficient cells, but not in control cells, treatment with the DNA methyltransferase inhibitor AZA was sufficient to upregulate miR-21 levels. Kruppel-like factors such as Erythroid Kruppel-like factor (EKLF or KLF1) can regulate chromatin structure by interacting with chromatin modifying proteins or chromatin remodelers (86-88). The observed regulation of MIR21 by KLF4 is especially interesting given the relationship between open chromatin and pluripotency (89).

KLF4-miR-21 signaling highlights the potential for distinct effects of KLF4 in loss- and gain-of-function experimental settings. As the oncogenic miR-21 is expressed independently of exogenous KLF4, KLF4 gain-of-function phenotypic studies may potentially underestimate protumorigenic signaling by the endogenous transcription factor. It is currently unclear whether KLF4 can regulate other loci in a similar fashion as for MIR21, or whether its regulation of MIR21 extends to other cell types.

Importantly, shRNA studies revealed both RASA1 and SPRED1 to be limiting endogenous factors for steady state RAS-ERK signaling through modulation of WT RAS-GTP levels, identifying these components as potential mediators of miR-206/21 effects (FIG. 10). miR loss- and gain-of-function studies using single anti-miRs or miR-mimics indicated that either miR-21 or miR-206 could individually regulate the level of these pathway inhibitors, but with only subtle effects on pERK 1/2 levels. Indicating cooperativity, larger fold effects were observed when anti-miRs or miR-mimics were combined to modulate both miR-206 and -21. Cooperativity was observed for the expression level of SPRED1, for the levels of pERK 1/2, and for relevant phenotypic parameters including tumor cell proliferation, migration, and survival.

As observed for SPRED1, RASA1 protein levels were dependent upon both miR-206 and miR-21. However, RASA1 did not consistently show cooperative regulation. Strikingly, RASA1 expression was nevertheless critical for miR-206/21 signaling, as anti-miR-206/21 had little or no discernible effect on pERK 1/2 levels in RASA1-deficient cells (FIG. 11). Likewise, cell proliferation and tumor initiation were concordantly anti-miR resistant in RASA1-deficient cells.

Supporting a functional role for SPRED1 in KLF4-miR signaling to RAS-ERK, SPRED1-suppressed cells not only displayed elevated pERK 1/2 levels, but also had resistance to anti-miR-206/21 that was intermediate as compared to shCtl cells and shRASA1 cells. This was shown by analysis of pERK 1/2 and cell proliferation, and tumor initiation in mice was anti-miR-resistant. The failure of anti-miR-206/21 to regulate pERK 1/2 levels in RASA1-deficient cells, despite upregulation of SPRED1, suggests that SPRED1 activity may be somehow limited in this context (FIG. 11). For example, this data would appear consistent with a critical role for RASA1 in signaling by SPRED1 or SPRED1-NF1 (13). On the other hand, in the context of MDA-MB-231 cells where SPRED1 but not RASA1 was cooperatively induced by anti-miR-206/21, the cooperative suppression of pERK 1/2 levels may be largely attributed to SPRED1, with RASA1 serving a more permissive role (FIG. 8).

Of interest in the current study was the similar effect of anti-miR-206/21 on RAS-ERK signaling in RAS-WT and RAS-mutant breast cancer cells alike. In RAS-mutant cells that were analyzed for RAS-GTP levels, only the WT RAS GTP was increased following depletion of either RASA1 or SPRED1. Consistent with our results, previous studies support the potential for these pathway inhibitors to antagonize signaling in cells harboring activated RAS (90-92). The effects of RASA1 and SPRED1 that we observed appear consistent with an important role of WT RAS proteins (i.e., KRAS, NRAS, and/or HRAS) for pathway activation in RAS-mutant TNBC cells. This model is supported by several previous analyses in non-mammary contexts (93-96). For example, suppression of the guanine nucleotide exchange factor SOS1 in a RAS-mutant context results in attenuation of WT RAS-GTP levels and pERK 1/2 levels, and suppresses tumorigenesis (94). In addition to effects on WT RAS proteins, the possibility that RASA1 and/or SPRED1 could suppress signaling by impacting other steps in the pathway is not excluded. Although additional studies are needed, these results support the targeting of RASA1 and SPRED1 for therapy of RAS-mutant as well as RAS-WT cancers.

We have identified a facet of KLF4 signaling that promotes malignant properties in TNBC cells, through miR-mediated activation of RAS-ERK signaling. The results highlight RASA1 and SPRED1 transcripts as latent tumor suppressors in TNBC cells, held at bay through KLF4-dependent miRs. The pronounced inhibitory effect of anti-miR-206/21 on the level of activated ERK 1/2 identifies the enhanced translation of RASA1 and SPRED1 as an attractive therapeutic strategy. In TNBCs the use of MEK 1/2 inhibitors typically induces a rapid compensatory reprogramming of the kinome, leading to drug resistance (33). Suppression of KLF4 or the anti-sense mediated silencing of miR-206 and/or miR-21 might be used in combination with MEK inhibitors or other pathway antagonists to attenuate this drug resistance.

We thank Steven M. Frisch (West Virginia University), Gary L. Johnson (University of North Carolina at Chapel Hill) and Jeffrey E. Green (NIH) for providing cell lines. Flow cytometry experiments were performed in the West Virginia University Flow Cytometry Core Facility. Orthotopic tumor cell injections were performed in the West Virginia University Animal Models & Imaging Facility.

TABLE 1

Pathway enrichment analysis of putative miR-206-regulated genes.

| KEGG pathway | p-value | Predicted targets in |
|---|---|---|
| Dorso-ventral axis formation | 2.58E−06 | 6 |
| Gap junction | 2.58E−06 | 9 |
| Glioma | 1.39E−05 | 9 |
| Long-term potentiation | 5.16E−05 | 9 |
| Transcriptional misregulation in cancer | 8.44E−05 | 16 |
| Thyroid cancer | 2.86E−04 | 4 |
| Chronic myeloid leukemia | 1.06E−03 | 8 |
| Prostate cancer | 1.48E−03 | 9 |
| Pentose phosphate pathway | 2.14E−03 | 4 |
| Neurotrophin signaling pathway | 4.13E−03 | 10 |
| Insulin signaling pathway | 4.13E−03 | 11 |
| Melanoma | 4.13E−03 | 7 |
| Spliceosome | 5.11E−03 | 11 |
| Bacterial invasion of epithelial cells | 5.11E−03 | 7 |
| mRNA surveillance pathway | 6.73E−03 | 7 |
| Alcoholism | 6.73E−03 | 12 |
| Non-small cell lung cancer | 8.82E−03 | 6 |
| MAPK signaling pathway | 1.24E−02 | 17 |
| Regulation of actin cytoskeleton | 1.38E−02 | 13 |
| Endometrial cancer | 1.47E−02 | 5 |
| Lysine degradation | 1.73E−02 | 4 |
| GnRH signaling pathway | 1.73E−02 | 7 |
| Dilated cardiomyopathy | 1.85E−02 | 7 |
| Progesterone-mediated oocyte maturation | 2.25E−02 | 7 |
| Glycosphingolipid biosynthesis - lacto and neolacto series | 2.75E−02 | 1 |

Genes containing potential miR-206 binding sites were analyzed using DIANA miRPath (97).

TABLE 2

Putative miR-206 target genes related to the MAPK/ERK signaling pathway.

| TARGET GENE | DIANA | MIRANDA | MIRBRIDGE | PICTAR | PITA | RNA22 | TARGETSCAN | TOTAL HIT |
|---|---|---|---|---|---|---|---|---|
| RASA1 | V | V | V | V | V | V | V | 7 |
| SPRED1 | V | V |  | V | V | V | V | 6 |
| RIT2 | V | V | V | V | V |  | V | 6 |
| MAP4K3 | V | V | V | V | V |  | V | 6 |
| BDNF | V | V | V | V | V |  | V | 6 |
| NGFR | V | V | V | V |  |  | V | 5 |
| PDGFA | V | V | V |  | V |  | V | 5 |
| PDCD4 | V |  |  | V |  | V | V | 4 |
| MAPK1 | V |  | V |  | V |  | V | 4 |
| CRK | V |  | V | V |  |  |  | 4 |
| MAP3K1 | V | V |  |  | V |  | V | 4 |
| SRC | V | V |  |  |  | V |  | 3 |
| RPS6KA5 | V | V | V |  |  |  |  | 3 |
| RAP1A | V |  |  | V |  |  | V | 3 |
| RALA | V |  | V | V |  |  |  | 3 |
| MAPK3 |  |  |  | V |  | V | V | 3 |

TABLE 2-continued

Putative miR-206 target genes related to the MAPK/ERK signaling pathway.

| TARGET GENE | DIANA | MIRANDA | MIRBRIDGE | PICTAR | PITA | RNA22 | TARGETSCAN | TOTAL HIT |
|---|---|---|---|---|---|---|---|---|
| KRAS | V | | V | | | | V | 3 |
| GNB1 | V | | V | V | | | | 3 |
| IKBKB | V | | V | | | V | | 3 |
| RAPGEF2 | V | | | | | V | V | 3 |
| PRKACB | V | | V | V | | | | 3 |

Candidate miR-206 target genes relevant to MAPK/ERK signaling were identified using KEGG, BIOCARTA, or REACTOME pathway analysis tools. Ranking (Total Hit) was performed using miRSystem (98).

TABLE 3

Pathway enrichment analysis of putative miR-21-regulated genes.

| KEGG pathway | p-value | Predicted targets in |
|---|---|---|
| Cytokine-cytokine receptor interaction | 6.55E−07 | 9 |
| Steroid biosynthesis | 1.26E−03 | 2 |
| Jak-STAT signaling pathway | 1.31E−03 | 7 |
| MAPK signaling pathway | 2.09E−03 | 9 |
| TGF-β signaling pathway | 5.88E−03 | 4 |
| Pancreatic cancer | 6.23E−03 | 4 |
| N-Glycan biosynthesis | 7.71E−03 | 2 |
| Hepatitis B | 1.06E−02 | 5 |
| Neurotrophin signaling pathway | 1.49E−02 | 5 |
| Viral carcinogenesis | 1.49E−02 | 6 |
| Small cell lung cancer | 1.49E−02 | 4 |
| Regulation of actin cytoskeleton | 2.60E−02 | 6 |
| Cell cycle | 2.76E−02 | 5 |
| Pathways in cancer | 3.06E−02 | 9 |

Genes containing potential miR-21 binding sites were analyzed using DIANA miRPath (97).

TABLE 4

Intersection of the pathways targeted by miR-206 and miR-21.

| KEGG pathway | p-value | Predicted targets in |
|---|---|---|
| MAPK signaling pathway | 3.00E−04 | 26 |
| Neurotrophin signaling pathway | 6.59E−04 | 14 |
| Regulation of actin cytoskeleton | 3.19E−03 | 19 |

Analysis was performed using DIANA miRPath (97).

REFERENCES

1. Weinberg R A. 2007. Growth Factors, Receptors, and Cancer, p. 119-158. In: Weinberg R A (ed.), The Biology of Cancer. Garland Science, Taylor and Francis Group, LLC, New York.
2. Johnson G L and Lapadat R. 2002. Mitogen-activated protein kinase pathways mediated by ERK, JNK, and p38 protein kinases. Science 298:1911-1912.
3. Downward J. 2003. Targeting RAS signalling pathways in cancer therapy. Nat Rev Cancer 3:11-22.
4. Kolch W. 2005. Coordinating ERK/MAPK signalling through scaffolds and inhibitors. Nat Rev Mol Cell Biol 6:827-837.
5. McCubrey J A, Steelman L S, Abrams S L, Lee J T, Chang F, Bertrand F E, Navolanic P M, Terrian D M, Franklin R A, D'Assoro A B, Salisbury J L, Mazzarino M C, Stivala F, and Libra M. 2006. Roles of the RAF/MEK/ERK and PI3K/PTEN/AKT pathways in malignant transformation and drug resistance. Adv Enzyme Regul 46:249-279.
6. Roberts P J and Der C J. 2007. Targeting the Raf-MEK-ERK mitogen-activated protein kinase cascade for the treatment of cancer. Oncogene 26:3291-3310.
7. Mebratu Y and Tesfaigzi Y. 2009. How ERK1/2 activation controls cell proliferation and cell death: Is subcellular localization the answer? Cell Cycle 8:1168-1175.
8. Young A, Lyons J, Miller A L, Phan V T, Alarcon I R, and McCormick F. 2009. Ras signaling and therapies. Adv Cancer Res 102:1-17.
9. Pylayeva-Gupta Y, Grabocka E, and Bar-Sagi D. 2011. RAS oncogenes: weaving a tumorigenic web. Nat Rev Cancer 11:761-774.
10. Boguski M S and McCormick F. 1993. Proteins regulating Ras and its relatives. Nature 366:643-654.
11. Yoshimura A. 2009. Regulation of cytokine signaling by the SOCS and Spred family proteins. Keio J Med 58:73-83.
12. Vigil D, Cherfils J, Rossman K L, and Der C J. 2010. Ras superfamily GEFs and GAPs: validated and tractable targets for cancer therapy? Nat Rev Cancer 10:842-857.
13. Stowe I B, Mercado E L, Stowe T R, Bell E L, Oses-Prieto J A, Hernandez H, Burlingame A L, and McCormick F. 2012. A shared molecular mechanism underlies the human rasopathies Legius syndrome and Neurofibromatosis-1. Genes Dev 26:1421-1426.
14. Brems H, Chmara M, Sahbatou M, Denayer E, Taniguchi K, Kato R, Somers R, Messiaen L, De Schepper S, Fryns J P, Cools J, Marynen P, Thomas G, Yoshimura A, and Legius E. 2007. Germline loss-of-function mutations in SPRED1 cause a neurofibromatosis 1-like phenotype. Nat Genet 39:1120-1126.
15. Schubbert S, Shannon K, and Bollag G. 2007. Hyperactive Ras in developmental disorders and cancer. Nat Rev Cancer 7:295-308.
16. Tidyman W E and Rauen K A. 2009. The RASopathies: developmental syndromes of Ras/MAPK pathway dysregulation. Curr Opin Genet Dev 19:230-236.
17. Bos J L. 1989. RAS oncogenes in human cancer: a review. Cancer Res 49:4682-4689.
18. Davies H, Bignell G R, Cox C, Stephens P, Edkins S, Clegg S, Teague J, Woffendin H, Garnett M J, Bottomley W, Davis N, Dicks E, Ewing R, Floyd Y, Gray K, Hall S, Hawes R, Hughes J, Kosmidou V, Menzies A, Mould C, Parker A, Stevens C, Watt S, Hooper S, Wilson R, Jayatilake H, Gusterson B A, Cooper C, Shipley J, Hargrave D, Pritchard-Jones K, Maitland N, Chenevix-Trench G, Riggins G J, Bigner D D, Palmieri G, Cossu A, Flanagan A, Nicholson A, Ho J W, Leung S Y, Yuen S T, Weber B L, Seigler H F, Darrow T L, Paterson H, Marais R, Marshall C J, Wooster R, Stratton M R, and Futreal P A. 2002. Mutations of the BRAF gene in human cancer. Nature 417:949-954.
19. Prior I A, Lewis P D, and Mattos C. 2012. A comprehensive survey of Ras mutations in cancer. Cancer Res 72:2457-2467.
20. Garnett M J and Marais R. 2004. Guilty as charged: B-RAF is a human oncogene. Cancer Cell 6:313-319.

21. Santen R J, Song R X, McPherson R, Kumar R, Adam L, Jeng M H, and Yue W. 2002. The role of mitogen-activated protein (MAP) kinase in breast cancer. J Steroid Biochem Mol Biol 80:239-256.
22. Whyte J, Bergin O, Bianchi A, McNally S, and Martin F. 2009. Key signalling nodes in mammary gland development and cancer. Mitogen-activated protein kinase signalling in experimental models of breast cancer progression and in mammary gland development. Breast Cancer Res 11:209.
23. Mirzoeva O K, Das D, Heiser L M, Bhattacharya S, Siwak D, Gendelman R, Bayani N, Wang N J, Neve R M, Guan Y, Hu Z, Knight Z, Feiler H S, Gascard P, Parvin B, Spellman P T, Shokat K M, Wyrobek A J, Bissell M J, McCormick F, Kuo W L, Mills G B, Gray J W, and Korn W M. 2009. Basal subtype and MAPK/ERK kinase (MEK)-phosphoinositide 3-kinase feedback signaling determine susceptibility of breast cancer cells to MEK inhibition. Cancer Res 69:565-572.
24. Hoeflich K P, O'Brien C, Boyd Z, Cavet G, Guerrero S, Jung K, Januario T, Savage H, Punnoose E, Truong T, Zhou W, Berry L, Murray L, Amler L, Belvin M, Friedman L S, and Lackner M R. 2009. In vivo antitumor activity of MEK and phosphatidylinositol 3-kinase inhibitors in basal-like breast cancer models. Clin Cancer Res 15:4649-4664.
25. Prat A and Perou C M. 2011. Deconstructing the molecular portraits of breast cancer. Mol Oncol 5:5-23.
26. van Beers E H, van Welsem T, Wessels L F, Li Y, Oldenburg R A, Devilee P, Cornelisse C J, Verhoef S, Hogervorst F B, van't Veer L J, and Nederlof P M. 2005. Comparative genomic hybridization profiles in human BRCA1 and BRCA2 breast tumors highlight differential sets of genomic aberrations. Cancer Res 65:822-827.
27. Herschkowitz J I, Simin K, Weigman V J, Mikaelian I, Usary J, Hu Z, Rasmussen K E, Jones L P, Assefnia S, Chandrasekharan S, Backlund M G, Yin Y, Khramtsov A I, Bastein R, Quackenbush J, Glazer R I, Brown P H, Green J E, Kopelovich L, Furth P A, Palazzo J P, Olopade O I, Bernard P S, Churchill G A, Van Dyke T, and Perou C M. 2007. Identification of conserved gene expression features between murine mammary carcinoma models and human breast tumors. Genome Biot 8:R76.
28. Rakha E A, Reis-Filho J S, and Ellis I O. 2008. Basal-like breast cancer: a critical review. J Clin Oncol 26:2568-2581.
29. Hu X, Stern H M, Ge L, O'Brien C, Haydu L, Honchell C D, Haverty P M, Peters B A, Wu T D, Amler L C, Chant J, Stokoe D, Lackner M R, and Cavet G. 2009. Genetic alterations and oncogenic pathways associated with breast cancer subtypes. Mol Cancer Res 7:511-522.
30. Cancer Genome Atlas Network. 2012. Comprehensive molecular portraits of human breast tumours. Nature 490:61-70.
31. Balko J M, Cook R S, Vaught D B, Kuba M G, Miller T W, Bhola N E, Sanders M E, Granja-Ingram N M, Smith J J, Meszoely I M, Salter J, Dowsett M, Stemke-Hale K, Gonzalez-Angulo A M, Mills G B, Pinto J A, Gomez H L, and Arteaga C L. 2012. Profiling of residual breast cancers after neoadjuvant chemotherapy identifies DUSP4 deficiency as a mechanism of drug resistance. Nat Med 18:1052-1059.
32. Gysin S, Salt M, Young A, and McCormick F. 2011. Therapeutic strategies for targeting ras proteins. Genes Cancer 2:359-372.
33. Duncan J S, Whittle M C, Nakamura K, Abell A N, Midland A A, Zawistowski J S, Johnson N L, Granger D A, Jordan N V, Darr D B, Usary J, Kuan P F, Smalley D M, Major B, He X, Hoadley K A, Zhou B, Sharpless N E, Perou C M, Kim W Y, Gomez S M, Chen X, Jin J, Frye S V, Earp H S, Graves L M, and Johnson G L. 2012. Dynamic reprogramming of the kinome in response to targeted MEK inhibition in triple-negative breast cancer. Cell 149:307-321.
34. Takahashi K and Yamanaka S. 2006. Induction of pluripotent stem cells from mouse embryonic and adult fibroblast cultures by defined factors. Cell 126:663-676.
35. Rowland B D and Peeper D S. 2006. KLF4, p21 and context-dependent opposing forces in cancer. Nat Rev Cancer 6:11-23.
36. McConnell B B and Yang V W. 2010. Mammalian Kruppel-like factors in health and diseases. Physiol Rev 90:1337-1381.
37. Ghaleb A M, McConnell B B, Nandan M O, Katz J P, Kaestner K H, and Yang V W. 2007. Haploinsufficiency of Kruppel-like factor 4 promotes adenomatous polyposis coli dependent intestinal tumorigenesis. Cancer Res 67:7147-7154.
38. McCormick S M, Eskin S G, McIntire L V, Teng C L, Lu C M, Russell C G, and Chittur K K. 2001. DNA microarray reveals changes in gene expression of shear stressed human umbilical vein endothelial cells. Proc Natl Acad Sci USA 98:8955-8960.
39. Yoon H S, Chen X, and Yang V W. 2003. Kruppel-like factor 4 mediates p53-dependent G1/S cell cycle arrest in response to DNA damage. J Biol Chem 278:2101-2105.
40. Pedersen T X, Leethanakul C, Patel V, Mitola D, Lund L R, Dano K, Johnsen M, Gutkind J S, and Bugge T H. 2003. Laser capture microdissection-based in vivo genomic profiling of wound keratinocytes identifies similarities and differences to squamous cell carcinoma. Oncogene 22:3964-3976.
41. Liu Y, Sinha S, McDonald O G, Shang Y, Hoofnagle M H, and Owens G K. 2005. Kruppel-like factor 4 abrogates myocardin-induced activation of smooth muscle gene expression. J Biol Chem 280:9719-9727.
42. Liu Y, Wang J, Yi Y, Zhang H, Liu J, Liu M, Yuan C, Tang D, Benjamin I J, and Xiao X. 2006. Induction of KLF4 in response to heat stress. Cell Stress Chaperones 11:379-389.
43. Ghaleb A M, Katz J P, Kaestner M I, Du J X, and Yang V W. 2007. Kruppel-like factor 4 exhibits antiapoptotic activity following gamma-radiation-induced DNA damage. Oncogene 26:2365-2373.
44. Hamik A, Lin Z, Kumar A, Balcells M, Sinha S, Katz J, Feinberg M W, Gerzsten R E, Edelman E R, and Jain M K. 2007. Kruppel-like factor 4 regulates endothelial inflammation. J Biol Chem 282:13769-13779.
45. Liao X, Haldar S M, Lu Y, Jeyaraj D, Paruchuri K, Nahori M, Cui Y, Kaestner K H, and Jain M K. 2010. Kruppel-like factor 4 regulates pressure-induced cardiac hypertrophy. J Mol Cell Cardiol 49:334-338.
46. Lai J K, Wu H C, Shen Y C, Hsieh H Y, Yang S Y, and Chang C C. 2012. Kruppel-like factor 4 is involved in cell scattering induced by hepatocyte growth factor. J Cell Sci 125:4853-4864.
47. Foster K W, Ren S, Louro I D, Lobo-Ruppert S M, McKie-Bell P, Grizzle W, Hayes M R, Broker T R, Chow L T, and Ruppert J M. 1999. Oncogene expression cloning by retroviral transduction of adenovirus E1A-immortalized rat kidney RK3E cells: transformation of a host with epithelial features by c-MYC and the zinc finger protein GKLF. Cell Growth Differ 10:423-434.

48. Foster K W, Liu Z, Nail C D, Li X, Fitzgerald T J, Bailey S K, Frost A R, Louro I D, Townes T M, Paterson A J, Kudlow J E, Lobo-Ruppert S M, and Ruppert J M. 2005. Induction of KLF4 in basal keratinocytes blocks the proliferation-differentiation switch and initiates squamous epithelial dysplasia. Oncogene 24:1491-1500.

49. Rowland B D, Bernards R, and Peeper D S. 2005. The KLF4 tumour suppressor is a transcriptional repressor of p53 that acts as a context-dependent oncogene. Nat Cell Biol 7:1074-1082.

50. Leng Z, Tao K, Xia Q, Tan J, Yue Z, Chen J, Xi H, Li J, and Zheng H. 2013. Kruppel-like factor 4 acts as an oncogene in colon cancer stem cell-enriched spheroid cells. PLoS One 8:e56082.

51. Pandya A Y, Talley L I, Frost A R, Fitzgerald T J, Trivedi V, Chakravarthy M, Chhieng D C, Grizzle W E, Engler J A, Krontiras H, Bland K I, Lobuglio A F, Lobo-Ruppert S M, and Ruppert J M. 2004. Nuclear localization of KLF4 is associated with an aggressive phenotype in early-stage breast cancer. Clin Cancer Res 10:2709-2719.

52. Chu P Y, Hsu N C, Liao A T, Yeh K T, Hou M F, and Liu C H. 2011. Elevated Kruppel-like factor 4 transcription factor in canine mammary carcinoma. BMC Vet Res 7:58.

53. Kamalakaran S, Varadan V, Giercksky Russnes H E, Levy D, Kendall J, Janevski A, Riggs M, Banerjee N, Synnestvedt M, Schlichting E, Karesen R, Shama P K, Rotti H, Rao R, Rao L, Eric Tang M H, Satyamoorthy K, Lucito R, Wigler M, Dimitrova N, Naume B, Borresen-Dale A L, and Hicks J B. 2011. DNA methylation patterns in luminal breast cancers differ from non-luminal subtypes and can identify relapse risk independent of other clinical variables. Mol Oncol 5:77-92.

54. Chen C J, Lin S E, Lin Y M, Lin S H, Chen D R, and Chen C L. 2012. Association of expression of Kruppel-like Factor 4 and Kruppel-like Factor 5 with the clinical manifestations of breast cancer. Pathol Oncol Res 18:161-168.

55. Lin C C, Liu L Z, Addison J B, Ivanov A V, and Ruppert J M. 2011. A KLF4-miRNA-206 autoregulatory feedback loop can promote or inhibit protein translation depending upon cell context. Mol Cell Biol 31:2513-2527.

56. Lee Y S and Dutta A. 2009. MicroRNAs in cancer. Annu Rev Pathol 4:199-227.

57. Kasinski A A and Slack F J. 2011. Epigenetics and genetics. MicroRNAs en route to the clinic: progress in validating and targeting microRNAs for cancer therapy. Nat Rev Cancer 11:849-864.

58. Iorio M V and Croce C M. 2012. MicroRNA dysregulation in cancer: diagnostics, monitoring and therapeutics. A comprehensive review. EMBO Mol Med 4:143-159.

59. Iorio M V, Ferracin M, Liu C G, Veronese A, Spizzo R, Sabbioni S, Magri E, Pedriali M, Fabbri M, Campiglio M, Menard S, Palazzo J P, Rosenberg A, Musiani P, Volinia S, Nenci I, Calin G A, Querzoli P, Negrini M, and Croce C M. 2005. MicroRNA gene expression deregulation in human breast cancer. Cancer Res 65:7065-7070.

60. Meng F, Henson R, Wehbe-Janek H, Ghoshal K, Jacob S T, and Patel T. 2007. MicroRNA-21 regulates expression of the PTEN tumor suppressor gene in human hepatocellular cancer. Gastroenterology 133:647-658.

61. Thum T, Gross C, Fiedler J, Fischer T, Kissler S, Bussen M, Galuppo P, Just S, Rottbauer W, Frantz S, Castoldi M, Soutschek J, Koteliansky V, Rosenwald A, Basson M A, Licht J D, Pena J T, Rouhanifard S H, Muckenthaler M U, Tuschl T, Martin G R, Bauersachs J, and Engelhardt S. 2008. MicroRNA-21 contributes to myocardial disease by stimulating MAP kinase signalling in fibroblasts. Nature 456:980-984.

62. Sayed D, Rane S, Lypowy J, He M, Chen I Y, Vashistha H, Yan L, Malhotra A, Vatner D, and Abdellatif M. 2008. MicroRNA-21 targets Sprouty2 and promotes cellular outgrowths. Mol Biol Cell 19:3272-3282.

63. Asangani I A, Rasheed S A, Nikolova D A, Leupold J H, Colburn N H, Post S, and Allgayer H. 2008. MicroRNA-21 (miR-21) post-transcriptionally downregulates tumor suppressor Pdcd4 and stimulates invasion, intravasation and metastasis in colorectal cancer. Oncogene 27:2128-2136.

64. Wickramasinghe N S, Manavalan T T, Dougherty S M, Riggs K A, Li Y, and Klinge C M. 2009. Estradiol downregulates miR-21 expression and increases miR-21 target gene expression in MCF-7 breast cancer cells. Nucleic Acids Res 37:2584-2595.

65. Hatley M E, Patrick D M, Garcia M R, Richardson J A, Bassel-Duby R, van Rooij E, and Olson E N. 2010. Modulation of K-Ras-dependent lung tumorigenesis by MicroRNA-21. Cancer Cell 18:282-293.

66. Zuker M. 2003. Mfold web server for nucleic acid folding and hybridization prediction. Nucleic Acids Res 31:3406-3415.

67. Mathelier A, Zhao X, Zhang A W, Parcy F, Worsley-Hunt R, Arenillas D J, Buchman S, Chen C Y, Chou A, Ienasescu H, Lim J, Shyr C, Tan G, Zhou M, Lenhard B, Sandelin A, and Wasserman W W. 2014. JASPAR 2014: an extensively expanded and updated open-access database of transcription factor binding profiles. Nucleic Acids Res 42:D142-D147.

68. Boyd K E and Farnham P J. 1999. Coexamination of site-specific transcription factor binding and promoter activity in living cells. Mol Cell Biol 19:8393-8399.

69. Littlewood T D, Hancock D C, Danielian P S, Parker M G, and Evan G I. 1995. A modified oestrogen receptor ligand-binding domain as an improved switch for the regulation of heterologous proteins. Nucleic Acids Res 23:1686-1690.

70. Zhang W, Geiman D E, Shields J M, Dang D T, Mahatan C S, Kaestner K H, Biggs J R, Kraft A S, and Yang V W. 2000. The gut-enriched Kruppel-like factor (Kruppel-like factor 4) mediates the transactivating effect of p53 on the p21WAF1/Cip1 promoter. J Biol Chem 275:18391-18398.

71. Geiman D E, Han T T, Johnson J M, and Yang V W. 2000. Transactivation and growth suppression by the gut-enriched Kruppel-like factor (Kruppel-like factor 4) are dependent on acidic amino acid residues and protein-protein interaction. Nucleic Acids Res 28:1106-1113.

72. Evans P M, Zhang W, Chen X, Yang J, Bhakat K K, and Liu C. 2007. Kruppel-like factor 4 is acetylated by p300 and regulates gene transcription via modulation of histone acetylation. J Biol Chem 282:33994-34002.

73. Yang X, Ferguson A T, Nass S J, Phillips D L, Butash K A, Wang S M, Herman J G, and Davidson N E. 2000. Transcriptional activation of estrogen receptor alpha in human breast cancer cells by histone deacetylase inhibition. Cancer Res 60:6890-6894.

74. Sharma D, Blum J, Yang X, Beaulieu N, Macleod A R, and Davidson N E. 2005. Release of methyl CpG binding proteins and histone deacetylase 1 from the Estrogen receptor alpha (ER) promoter upon reactivation in ER-negative human breast cancer cells. Mol Endocrinol 19:1740-1751.

75. Lewis B P, Burge C B, and Bartel D P. 2005. Conserved seed pairing, often flanked by adenosines, indicates that thousands of human genes are microRNA targets. Cell 120:15-20.
76. Fukazawa H, Noguchi K, Murakami Y, and Uehara Y. 2002. Mitogen-activated protein/extracellular signal-regulated kinase kinase (MEK) inhibitors restore anoikis sensitivity in human breast cancer cell lines with a constitutively activated extracellular-regulated kinase (ERK) pathway. Mol Cancer Ther 1:303-309.
77. Turner N, Lambros M B, Horlings H M, Pearson A, Sharpe R, Natrajan R, Geyer F C, van Kouwenhove M, Kreike B, Mackay A, Ashworth A, Van de Vijver M J, and Reis-Filho J S. 2010. Integrative molecular profiling of triple negative breast cancers identifies amplicon drivers and potential therapeutic targets. Oncogene 29:2013-2023.
78. Infante J R, Papadopoulos K P, Bendell J C, Patnaik A, Burris H A, III, Rasco D, Jones S F, Smith L, Cox D S, Durante M, Bellew K M, Park J J, Le N T, and Tolcher A W. 2013. A phase 1b study of trametinib, an oral Mitogen-activated protein kinase kinase (MEK) inhibitor, in combination with gemcitabine in advanced solid tumours. Eur J Cancer 49:2077-2085.
79. Britten C D. 2013. PI3K and MEK inhibitor combinations: examining the evidence in selected tumor types. Cancer Chemother Pharmacol 71:1395-1409.
80. Kondo N, Toyama T, Sugiura H, Fujii Y, and Yamashita H. 2008. miR-206 Expression is down-regulated in estrogen receptor α-positive human breast cancer. Cancer Res 68:5004-5008.
81. Williams A H, Valdez G, Moresi V, Qi X, McAnally J, Elliott J L, Bassel-Duby R, Sanes J R, and Olson E N. 2009. MicroRNA-206 delays ALS progression and promotes regeneration of neuromuscular synapses in mice. Science 326:1549-1554.
82. Dey B K, Gagan J, and Dutta A. 2011. miR-206 and -486 induce myoblast differentiation by downregulating Pax7. Mol Cell Biol 31:203-214.
83. Liu N, Williams A H, Maxeiner J M, Bezprozvannaya S, Shelton J M, Richardson J A, Bassel-Duby R, and Olson E N. 2012. microRNA-206 promotes skeletal muscle regeneration and delays progression of Duchenne muscular dystrophy in mice. J Clin Invest 122:2054-2065.
84. Guttilla I K and White B A. 2009. Coordinate regulation of FOXO1 by miR-27a, miR-96, and miR-182 in breast cancer cells. J Biol Chem 284:23204-23216.
85. Fujita S, Ito T, Mizutani T, Minoguchi S, Yamamichi N, Sakurai K, and Iba H. 2008. miR-21 Gene expression triggered by AP-1 is sustained through a double-negative feedback mechanism. J Mol Biol 378:492-504.
86. Armstrong J A, Bieker J J, and Emerson B M. 1998. A SWI/SNF-related chromatin remodeling complex, E-RC1, is required for tissue-specific transcriptional regulation by EKLF in vitro. Cell 95:93-104.
87. Kadam S and Emerson B M. 2003. Transcriptional specificity of human SWI/SNF BRG1 and BRM chromatin remodeling complexes. Mol Cell 11:377-389.
88. Wu J I, Lessard J, and Crabtree G R. 2009. Understanding the words of chromatin regulation. Cell 136:200-206.
89. Gaspar-Maia A, Alajem A, Meshorer E, and Ramalho-Santos M. 2011. Open chromatin in pluripotency and reprogramming. Nat Rev Mol Cell Biol 12:36-47.
90. Clark G J, Quilliam L A, Hisaka M M, and Der C J. 1993. Differential antagonism of Ras biological activity by catalytic and Src homology domains of Ras GTPase activation protein. Proc Natl Acad Sci USA 90:4887-4891.
91. Huang D C, Marshall C J, and Hancock J F. 1993. Plasma membrane-targeted ras GTPase-activating protein is a potent suppressor of p21ras function. Mol Cell Biol 13:2420-2431.
92. Wakioka T, Sasaki A, Kato R, Shouda T, Matsumoto A, Miyoshi K, Tsuneoka M, Komiya S, Baron R, and Yoshimura A. 2001. Spred is a Sprouty-related suppressor of Ras signalling. Nature 412:647-651.
93. Fotiadou P P, Takahashi C, Rajabi H N, and Ewen M E. 2007. Wild-type NRas and KRas perform distinct functions during transformation. Mol Cell Biol 27:6742-6755.
94. Jeng H H, Taylor L J, and Bar-Sagi D. 2012. Sos-mediated cross-activation of wild-type Ras by oncogenic Ras is essential for tumorigenesis. Nat Commun 3:1168.
95. Young A, Lou D, and McCormick F. 2013. Oncogenic and wild-type Ras play divergent roles in the regulation of mitogen-activated protein kinase signaling. Cancer Discov 3:112-123.
96. Grabocka E, Pylayeva-Gupta Y, Jones M J, Lubkov V, Yemanaberhan E, Taylor L, Jeng H H, and Bar-Sagi D. 2014. Wild-type H- and N-ras promote mutant K-ras-driven tumorigenesis by modulating the DNA damage response. Cancer Cell 25:243-256.
97. Vlachos I S, Kostoulas N, Vergoulis T, Georgakilas G, Reczko M, Maragkakis M, Paraskevopoulou M D, Prionidis K, Dalamagas T, and Hatzigeorgiou A G. 2012. DIANA miRPath v.2.0: investigating the combinatorial effect of microRNAs in pathways. Nucleic Acids Res 40:W498-W504.
98. Lu T P, Lee C Y, Tsai M H, Chiu Y C, Hsiao C K, Lai L C, and Chuang E Y. 2012. miRSystem: an integrated system for characterizing enriched functions and pathways of microRNA targets. PLoS One 7:e42390.

Whereas particular embodiments of this invention have been described above for purposes of illustration, it will be evident to those persons skilled in the art that numerous variations of the details of the present invention may be made without departing from the invention as defined herein and in the appended claims.

What is claimed is:

1. A method of treating a patient having triple negative breast cancer by administering to said patient a therapeutically effective amount of an anti-microRNA 206 and a therapeutically effective amount of an anti-microRNA 21.

* * * * *

UNITED STATES PATENT AND TRADEMARK OFFICE
CERTIFICATE OF CORRECTION

PATENT NO. : 10,221,415 B2
APPLICATION NO. : 15/252865
DATED : March 5, 2019
INVENTOR(S) : Sriganesh B. Sharma et al.

Page 1 of 1

It is certified that error appears in the above-identified patent and that said Letters Patent is hereby corrected as shown below:

In the Specification

Column 1, Lines 20-30: change "This invention was made with government support under Grant No. RO1 CA127405 awarded by the National Cancer Institute, under equipment Grant No. RR020866 awarded by the National Institute of Health, under Grant Nos. P30GM103488 (CoBRE) and P20GM103434 (INBRE) awarded by the Institutional Development Award (IDeA) from the National Institute of General Medical Sciences, and under Grant Nos. P20 RR016440, P30 RR032138/GM103488 and S10 RR026378 awarded by the National Institute of Health. The government has certain rights in this invention." to -- This invention was made with government support under Grant Nos. R01 CA 127405, RR020866, P30 GM103488, P20 GM103434, P20 RR016440, P30 RR032138/GM103488 and S10 RR026378 awarded by the National Institute of Health. The government has certain rights in this invention. --

Signed and Sealed this
Seventh Day of January, 2020

Andrei Iancu
*Director of the United States Patent and Trademark Office*

SEQUENCE LISTING

<160> NUMBER OF SEQ ID NOS: 49

<210> SEQ ID NO 1
<211> LENGTH: 22
<212> TYPE: RNA
<213> ORGANISM: Homo sapiens

<400> SEQUENCE: 1
uagcacacuu uuccacauuc ca                                              22

<210> SEQ ID NO 2
<211> LENGTH: 22
<212> TYPE: RNA
<213> ORGANISM: Pan troglodytes

<400> SEQUENCE: 2
uagcacacuu uuccacauuc ca            22

<210> SEQ ID NO 3
<211> LENGTH: 22
<212> TYPE: RNA
<213> ORGANISM: Mus musculus

<400> SEQUENCE: 3
uagcacacuu ucccacauuc ca            22

<210> SEQ ID NO 4
<211> LENGTH: 22
<212> TYPE: RNA
<213> ORGANISM: Bos taurus

<400> SEQUENCE: 4
uagcacaccu uuccacauuc ca            22

<210> SEQ ID NO 5
<211> LENGTH: 20
<212> TYPE: RNA
<213> ORGANISM: Homo sapiens

<400> SEQUENCE: 5
auaucuacug ucacauucca            20

<210> SEQ ID NO 6
<211> LENGTH: 20
<212> TYPE: RNA
<213> ORGANISM: Pan troglodytes

<400> SEQUENCE: 6
auaucuacug ucacauucca            20

<210> SEQ ID NO 7
<211> LENGTH: 20
<212> TYPE: RNA
<213> ORGANISM: Mus musculus

<400> SEQUENCE: 7
auaucugcca ccacauucca            20

<210> SEQ ID NO 8
<211> LENGTH: 20
<212> TYPE: RNA
<213> ORGANISM: Bos taurus

<400> SEQUENCE: 8
auaucuacug ucacauucca            20

<210> SEQ ID NO 9
<211> LENGTH: 22
<212> TYPE: RNA
<213> ORGANISM: Homo sapiens

<400> SEQUENCE: 9

```
uggaauguaa ggaagugugu gg                                              22

<210> SEQ ID NO 10
<211> LENGTH: 22
<212> TYPE: RNA
<213> ORGANISM: artificial sequence
<220> FEATURE:
<223> OTHER INFORMATION: Homo sapiens UTR mutant

<400> SEQUENCE: 10
uagcacacuu uuccaacucu ca                                              22

<210> SEQ ID NO 11
<211> LENGTH: 22
<212> TYPE: RNA
<213> ORGANISM: artificial sequence
<220> FEATURE:
<223> OTHER INFORMATION: Homo sapiens mutant strain

<400> SEQUENCE: 11
auauaucuac ugucaacucu ca                                              22

<210> SEQ ID NO 12
<211> LENGTH: 22
<212> TYPE: RNA
<213> ORGANISM: Homo sapiens

<400> SEQUENCE: 12
augccagcaa ccuuguaagc ua                                              22

<210> SEQ ID NO 13
<211> LENGTH: 22
<212> TYPE: RNA
<213> ORGANISM: Pan troglodytes

<400> SEQUENCE: 13
augccagcaa ccuuguaagc ua                                              22

<210> SEQ ID NO 14
<211> LENGTH: 22
<212> TYPE: RNA
<213> ORGANISM: Mus musculus

<400> SEQUENCE: 14
cugccagcac cuuuguaagc ua                                              22

<210> SEQ ID NO 15
<211> LENGTH: 22
<212> TYPE: RNA
<213> ORGANISM: Gallus gallus

<400> SEQUENCE: 15
guaccagcag cuuuuuaagc ua                                              22

<210> SEQ ID NO 16
<211> LENGTH: 21
<212> TYPE: RNA
<213> ORGANISM: Homo sapiens

<400> SEQUENCE: 16
uuuuuuuaag ucucuaagcu a                                               21

<210> SEQ ID NO 17
<211> LENGTH: 21
```

```
<212> TYPE: RNA
<213> ORGANISM: Pan troglodytes

<400> SEQUENCE: 17
auuuuuuaag ucucuaagcu a                                              21

<210> SEQ ID NO 18
<211> LENGTH: 21
<212> TYPE: RNA
<213> ORGANISM: Homo sapiens

<400> SEQUENCE: 18
uaacauguug cagcuaagcu a                                              21

<210> SEQ ID NO 19
<211> LENGTH: 21
<212> TYPE: RNA
<213> ORGANISM: Pan troglodytes

<400> SEQUENCE: 19
uaacauguug cagcuaagcu a                                              21

<210> SEQ ID NO 20
<211> LENGTH: 14
<212> TYPE: RNA
<213> ORGANISM: Homo sapiens

<400> SEQUENCE: 20
aaccuuguaa gcua                                                      14

<210> SEQ ID NO 21
<211> LENGTH: 14
<212> TYPE: RNA
<213> ORGANISM: Homo sapiens

<400> SEQUENCE: 21
uagcuuauca gacu                                                      14

<210> SEQ ID NO 22
<211> LENGTH: 19
<212> TYPE: RNA
<213> ORGANISM: Homo sapiens

<400> SEQUENCE: 22
acauguugca gcuaagcua                                                 19

<210> SEQ ID NO 23
<211> LENGTH: 21
<212> TYPE: RNA
<213> ORGANISM: Homo sapiens

<400> SEQUENCE: 23
uagcuuauca gacugauguu g                                              21

<210> SEQ ID NO 24
<211> LENGTH: 19
<212> TYPE: RNA
<213> ORGANISM: Homo sapiens

<400> SEQUENCE: 24
uagcuuauca gacugaugu                                                 19

<210> SEQ ID NO 25
```

```
<211> LENGTH: 21
<212> TYPE: RNA
<213> ORGANISM: artificial sequence
<220> FEATURE:
<223> OTHER INFORMATION: mutant of Homo sapiens

<400> SEQUENCE: 25
uuuuuuuaag ucucuagauc a                                              21

<210> SEQ ID NO 26
<211> LENGTH: 19
<212> TYPE: RNA
<213> ORGANISM: Homo sapiens

<400> SEQUENCE: 26
acauguugca gcuacccua                                                 19

<210> SEQ ID NO 27
<211> LENGTH: 31
<212> TYPE: DNA
<213> ORGANISM: artificial sequence
<220> FEATURE:
<223> OTHER INFORMATION: pcr amplifier

<400> SEQUENCE: 27
cccacgcgtt gaaaaactgt ttaactcatg t                                   31

<210> SEQ ID NO 28
<211> LENGTH: 31
<212> TYPE: DNA
<213> ORGANISM: artificial sequence
<220> FEATURE:
<223> OTHER INFORMATION: PCR amplifier

<400> SEQUENCE: 28
cccacgcgtt gaaaaacctg taaataagca c                                   31

<210> SEQ ID NO 29
<211> LENGTH: 45
<212> TYPE: DNA
<213> ORGANISM: artificial sequence
<220> FEATURE:
<223> OTHER INFORMATION: PCR primer

<400> SEQUENCE: 29
aaaaatagca cacttttcca actctcagtg atgtgtgagc tatgc                    45

<210> SEQ ID NO 30
<211> LENGTH: 45
<212> TYPE: DNA
<213> ORGANISM: artificial sequence
<220> FEATURE:
<223> OTHER INFORMATION: pcr primer

<400> SEQUENCE: 30
gcatagctca cacatcactg agagttggaa aagtgtgcta ttttt                    45

<210> SEQ ID NO 31
<211> LENGTH: 45
<212> TYPE: DNA
<213> ORGANISM: artificial sequence
<220> FEATURE:
<223> OTHER INFORMATION: pcr primer

<400> SEQUENCE: 31
atatatatat ctactgtcaa ctctcatata ttttgaatat ttaac                    45
```

<210> SEQ ID NO 32
<211> LENGTH: 45
<212> TYPE: DNA
<213> ORGANISM: artificial sequence
<220> FEATURE:
<223> OTHER INFORMATION: pcr primer

<400> SEQUENCE: 32
gttaaatatt caaatatat gagagttgac agtagatata tatat          45

<210> SEQ ID NO 33
<211> LENGTH: 50
<212> TYPE: DNA
<213> ORGANISM: artificial sequence
<220> FEATURE:
<223> OTHER INFORMATION: pcr primer

<400> SEQUENCE: 33
gtattcagat ttttttttaa gtctctagat caataatgtt atatttattg          50

<210> SEQ ID NO 34
<211> LENGTH: 50
<212> TYPE: DNA
<213> ORGANISM: artificial sequence
<220> FEATURE:
<223> OTHER INFORMATION: pcr primer

<400> SEQUENCE: 34
caataaatat aacattattg atctagagac ttaaaaaaaa atctgaatac          50

<210> SEQ ID NO 35
<211> LENGTH: 45
<212> TYPE: DNA
<213> ORGANISM: artificial sequence
<220> FEATURE:
<223> OTHER INFORMATION: pcr primer

<400> SEQUENCE: 35
ttggtaacat gttgcagcta ccctaatgac cttaagtggc aattg          45

<210> SEQ ID NO 36
<211> LENGTH: 45
<212> TYPE: DNA
<213> ORGANISM: artificial sequence
<220> FEATURE:
<223> OTHER INFORMATION: pcr primer

<400> SEQUENCE: 36
caattgccac ttaaggtcat tagggtagct gcaacatgtt accaa          45

<210> SEQ ID NO 37
<211> LENGTH: 20
<212> TYPE: DNA
<213> ORGANISM: artificial sequence
<220> FEATURE:
<223> OTHER INFORMATION: pcr primer

<400> SEQUENCE: 37
aggtggacct gatcatggag          20

<210> SEQ ID NO 38
<211> LENGTH: 20
<212> TYPE: DNA
<213> ORGANISM: artificial sequence
<220> FEATURE:

<223> OTHER INFORMATION: pcr primer

<400> SEQUENCE: 38
aagcttcgat gatgggctta                                           20

<210> SEQ ID NO 39
<211> LENGTH: 20
<212> TYPE: DNA
<213> ORGANISM: artificial sequence
<220> FEATURE:
<223> OTHER INFORMATION: pcr primer

<400> SEQUENCE: 39
tctctgctgg atgacgtgag                                           20

<210> SEQ ID NO 40
<211> LENGTH: 19
<212> TYPE: DNA
<213> ORGANISM: artificial sequence
<220> FEATURE:
<223> OTHER INFORMATION: pcr primer

<400> SEQUENCE: 40
tagctgtgct cgcgctact                                            19

<210> SEQ ID NO 41
<211> LENGTH: 20
<212> TYPE: DNA
<213> ORGANISM: Homo sapiens

<400> SEQUENCE: 41
cttagattga gaaagaccgc                                           20

<210> SEQ ID NO 42
<211> LENGTH: 20
<212> TYPE: DNA
<213> ORGANISM: Homo sapiens

<400> SEQUENCE: 42
acttatgctt gtgtcatccc                                           20

<210> SEQ ID NO 43
<211> LENGTH: 20
<212> TYPE: DNA
<213> ORGANISM: Homo sapiens

<400> SEQUENCE: 43
gcaacctcca cttcctgggt                                           20

<210> SEQ ID NO 44
<211> LENGTH: 20
<212> TYPE: DNA
<213> ORGANISM: Homo sapiens

<400> SEQUENCE: 44
ccaacacagt gaaaccctgt                                           20

<210> SEQ ID NO 45
<211> LENGTH: 20
<212> TYPE: DNA
<213> ORGANISM: Homo sapiens

<400> SEQUENCE: 45
catcaacaac accccaagcg                                           20

```
<210> SEQ ID NO 46
<211> LENGTH: 21
<212> TYPE: DNA
<213> ORGANISM: Homo sapiens

<400> SEQUENCE: 46
ggcacagttt tggatcaacc c                                      21

<210> SEQ ID NO 47
<211> LENGTH: 21
<212> TYPE: DNA
<213> ORGANISM: Homo sapiens

<400> SEQUENCE: 47
tgcaaagcac agagaaacgt g                                      21

<210> SEQ ID NO 48
<211> LENGTH: 23
<212> TYPE: DNA
<213> ORGANISM: Homo sapiens

<400> SEQUENCE: 48
accttcttcc cattttcctg gac                                    23

<210> SEQ ID NO 49
<211> LENGTH: 22
<212> TYPE: RNA
<213> ORGANISM: Homo sapiens

<400> SEQUENCE: 49
auauaucuac ugucacauuc ca                                     22
```